United States Patent
Payne et al.

(10) Patent No.: US 7,510,869 B2
(45) Date of Patent: Mar. 31, 2009

(54) PROMOTER AND PLASMID SYSTEM FOR GENETIC ENGINEERING

(75) Inventors: Mark S. Payne, Wilmington, DE (US); Stephen K. Picataggio, Landenberg, PA (US); Amy Kuang-Hsu, Redwood City, CA (US); Ramesh Velayudhan Nair, Cupertino, CA (US); Fernado Valle, Burlingame, CA (US); Philippe Soucaille, San Francisco, CA (US); Donald Eugene Trimbur, Redwood City, CA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 109 days.

(21) Appl. No.: 11/541,810

(22) Filed: Oct. 2, 2006

(65) Prior Publication Data

US 2007/0065867 A1    Mar. 22, 2007

Related U.S. Application Data

(60) Division of application No. 10/739,542, filed on Dec. 18, 2003, now Pat. No. 7,132,527, which is a continuation of application No. 10/420,587, filed on Apr. 22, 2003.

(60) Provisional application No. 60/374,931, filed on Apr. 22, 2002.

(51) Int. Cl.
  *C12N 15/00* (2006.01)
  *C12P 19/34* (2006.01)
(52) U.S. Cl. .................. 435/320.1; 435/91.1
(58) Field of Classification Search ......... None
  See application file for complete search history.

(56) References Cited

U.S. PATENT DOCUMENTS 5,547,862 A    8/1996    Meador et al.

FOREIGN PATENT DOCUMENTS

| CN | 1186856 | 7/1998 |
|---|---|---|
| WO | WO 96/35796 | 11/1996 |
| WO | WO 01/12833 A2 | 2/2001 |
| WO | WO 02/086135 A2 | 10/2002 |

OTHER PUBLICATIONS

Rene Amore et al., The fermentation of xylose—an analysis of the expression of Bacillus and Actinoplanes xylose isomerase genes in yeast, Appl. Microbiol. Biotechnol., vol. 30:351-357 (1989).
Martin Fussenegger et al., pTRIDENT, a Novel Vector Family for Tricistronic Gene Expression in Mammalian Cells, Biotechnology and Bioengineering, vol. 57(1):1-10, 1998.
A. Delafuente et al., Restriction end-converting vectors with tandem repeated multiple cloning sites, Gene, vol. 139:83-86, 1994.
Yoshikatsu Murooka and Isao Mitani, Efficient expression of a promoter-controlled gene: Tandem promoters of lambda P and P functional enteric bacteria, Journal of Biotechnology, vol. 2:303-316, 1985.
Glick, B. R. and J. J. Pasternak, "Molecular Biotechnology Principles and Applications of Recombinant DNA", 2$^{nd}$ Edition, American Society for Microbiology, Washington, D.C., 1998 (Entire book not attached—Book Cover page, Title Page & Table of Contents Only).
J. W. Meador, III et al., pTRIPLEscript(TM): A Novel Cloning Vector for Generating In Vitro Transcripts from Tandem Promoters for SP6, T7 and T3 RNA Polymerases, Biotechniques, vol. 18(1):152-154, 156-157, 1995.

*Primary Examiner*—Joanne Hama

(57) ABSTRACT

This invention provides a series of low-copy number plasmids comprising restriction endonuclease recognition sites useful for cloning at least three different genes or operons, each flanked by a terminator sequence, the plasmids containing variants of glucose isomerase promoters for varying levels of protein expression. The materials and methods are useful for genetic engineering in microorganisms, especially where multiple genetic insertions are sought.

1 Claim, No Drawings

SEQUENCE LISTING

<160> NUMBER OF SEQ ID NOS: 83

<210> SEQ ID NO 1
<211> LENGTH: 199
<212> TYPE: DNA
<213> ORGANISM: artificial sequence
<220> FEATURE:
<223> OTHER INFORMATION: promoter

<400> SEQUENCE: 1
gaattcacta gtcgatctgt gctgtttgcc acggtatgca gcaccagcgc gagattatgg      60
gctcgcacgc tcgactgtcg gacggggggca ctggaacgag aagtcaggcg agccgtcacg     120
cccttgacaa tgccacatcc tgagcaaata attcaaccac taaacaaatc aaccgcgttt     180
cccggaggta accaagctt                                                          199

<210> SEQ ID NO 2
<211> LENGTH: 36
<212> TYPE: DNA
<213> ORGANISM: artificial sequence
<220> FEATURE:
<223> OTHER INFORMATION: primer

<400> SEQUENCE: 2
cgggaattcc ctaggcgatc tgtgctgttt gccacg                                        36

<210> SEQ ID NO 3
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (74)..(74)
<223> OTHER INFORMATION: N = A, T, C, or G

<400> SEQUENCE: 3
cttaagcttg gttacctccg ggaaacgcgg ttgatttgtt tagtggttga attatttgct              60
caggatgtgg catngtcaag ggcg                                                     84

<210> SEQ ID NO 4
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (75)..(75)
<223> OTHER INFORMATION: N = A, T, C, or G

<400> SEQUENCE: 4
cttaagcttg gttacctccg ggaaacgcgg ttgatttgtt tagtggttga attatttgct              60
caggatgtgg cattntcaag ggcg                                                     84

<210> SEQ ID NO 5
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (76)..(76)
<223> OTHER INFORMATION: N = A, T, C, or G

<400> SEQUENCE: 5
cttaagcttg gttacctccg ggaaacgcgg ttgatttgtt tagtggttga attatttgct              60
caggatgtgg cattgncaag ggcg                                                     84

<210> SEQ ID NO 6
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (77)..(77)

<223> OTHER INFORMATION: N = A, T, C, or G

<400> SEQUENCE: 6
cttaagcttg gttacctccg ggaaacgcgg ttgatttgtt tagtggttga attatttgct    60
caggatgtgg cattgtnaag ggcg    84

<210> SEQ ID NO 7
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (78)..(78)
<223> OTHER INFORMATION: N = A, T, C, or G

<400> SEQUENCE: 7
cttaagcttg gttacctccg ggaaacgcgg ttgatttgtt tagtggttga attatttgct    60
caggatgtgg cattgtcnag ggcg    84

<210> SEQ ID NO 8
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (79)..(79)
<223> OTHER INFORMATION: N = A, T, C, or G

<400> SEQUENCE: 8
cttaagcttg gttacctccg ggaaacgcgg ttgatttgtt tagtggttga attatttgct    60
caggatgtgg cattgtcang ggcg    84

<210> SEQ ID NO 9
<211> LENGTH: 187
<212> TYPE: DNA
<213> ORGANISM: artificial sequence
<220> FEATURE:
<223> OTHER INFORMATION: promoter

<400> SEQUENCE: 9
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
acaatgccac atcctgagca aataattcaa ccactaaaca aatcaaccgc gtttcccgga   180
ggtaacc    187

<210> SEQ ID NO 10
<211> LENGTH: 187
<212> TYPE: DNA
<213> ORGANISM: artificial sequence
<220> FEATURE:
<223> OTHER INFORMATION: promoter

<400> SEQUENCE: 10
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
actatgccac atcctgagca aataattcaa ccactaaaca aatcaaccgc gtttcccgga   180
ggtaacc    187

<210> SEQ ID NO 11
<211> LENGTH: 187
<212> TYPE: DNA
<213> ORGANISM: artificial sequence
<220> FEATURE:
<223> OTHER INFORMATION: promoter

<400> SEQUENCE: 11
cctaggcgat ctgtgctgtt tgccacggta tgcagcacca gcgcgagatt atgggctcgc     60
acgctcgact gtcggacggg ggcactggaa cgagaagtca ggcgagccgt cacgcccttg    120
acgatgccac atcctgagca ataattcaa ccactaaaca aatcaaccgc gtttcccgga    180
ggtaacc                                                              187

<210> SEQ ID NO 12
<211> LENGTH: 187
<212> TYPE: DNA
<213> ORGANISM: artificial sequence
<220> FEATURE:
<223> OTHER INFORMATION: promoter

<400> SEQUENCE: 12
cctaggcgat ctgtgctgtt tgccacggta tgcagcacca gcgcgagatt atgggctcgc     60
acgctcgact gtcggacggg ggcactggaa cgagaagtca ggcgagccgt cacgcccttg    120
accatgccac atcctgagca ataattcaa ccactaaaca aatcaaccgc gtttcccgga    180
ggtaacc                                                              187

<210> SEQ ID NO 13
<211> LENGTH: 186
<212> TYPE: DNA
<213> ORGANISM: artificial sequence
<220> FEATURE:
<223> OTHER INFORMATION: promoter

<400> SEQUENCE: 13
ctaggcgatc tgtgctgttt gccacggtat gcagcaccag cgcgagatta tgggctcgca     60
cgctcgactg tcggacgggg gcactggaac gagaagtcag gcgagccgtc acgcccttga    120
aaatgccaca tcctgagcaa ataattcaac cactaaacaa atcaaccgcg tttcccggag    180
gtaacc                                                               186

<210> SEQ ID NO 14
<211> LENGTH: 162
<212> TYPE: DNA
<213> ORGANISM: artificial sequence
<220> FEATURE:
<223> OTHER INFORMATION: promoter

<400> SEQUENCE: 14
cctaggcgat ctgtgctgtt tgccacggta tgcagcacca gcgcgagatt atgggctcgc     60
acgctcgact gtcggacggg ggcactggaa cgagaagtca ggcgagccgt cacgcccttg    120
acaatgccac atcctgagca ataattttc ccggaggtaa cc                        162

<210> SEQ ID NO 15
<211> LENGTH: 187
<212> TYPE: DNA
<213> ORGANISM: artificial sequence
<220> FEATURE:
<223> OTHER INFORMATION: promoter

```
<400> SEQUENCE: 15
cctaggcgat ctgtgctgtt tgccacggta tgcagcacca gcgcgagatt atgggctcgc      60
acgctcgact gtcggacggg ggcactggaa cgagaagtca ggcgagccgt cacgcccttg     120
ccaatgccac atcctgagca aataattcaa ccactaaaca aatcaaccgc gtttcccgga     180
ggtaacc                                                               187

<210> SEQ ID NO 16
<211> LENGTH: 187
<212> TYPE: DNA
<213> ORGANISM: artificial sequence
<220> FEATURE:
<223> OTHER INFORMATION: promoter

<400> SEQUENCE: 16
cctaggcgat ctgtgctgtt tgccacggta tgcagcacca gcgcgagatt atgggctcgc      60
acgctcgact gtcggacggg ggcactggaa cgagaagtca ggcgagccgt cacgccctta     120
acaatgccac atcctgagca aataattcaa ccactaaaca aatcaaccgc gtttcccgga     180
ggtaacc                                                               187

<210> SEQ ID NO 17
<211> LENGTH: 187
<212> TYPE: DNA
<213> ORGANISM: artificial sequence
<220> FEATURE:
<223> OTHER INFORMATION: promoter

<400> SEQUENCE: 17
cctaggcgat ctgtgctgtt tgccacggta tgcagcacca gcgcgagatt atgggctcgc      60
acgctcgact gtcggacggg ggcactggaa cgagaagtca ggcgagccgt cacgcccttc     120
acaatgccac atcctgagca aataattcaa ccactaaaca aatcaaccgc gtttcccgga     180
ggtaacc                                                               187

<210> SEQ ID NO 18
<211> LENGTH: 187
<212> TYPE: DNA
<213> ORGANISM: artificial sequence
<220> FEATURE:
<223> OTHER INFORMATION: promoter

<400> SEQUENCE: 18
cctaggcgat ctgtgctgtt tgccacggta tgcagcacca gcgcgagatt atgggctcgc      60
acgctcgact gtcggacggg ggcactggaa cgagaagtca ggcgagccgt cacgccctcg     120
acaatgccac atcctgagca aataattcaa ccactaaaca aatcaaccgc gtttcccgga     180
ggtaacc                                                               187

<210> SEQ ID NO 19
<211> LENGTH: 187
<212> TYPE: DNA
<213> ORGANISM: artificial sequence
<220> FEATURE:
<223> OTHER INFORMATION: promoter

<400> SEQUENCE: 19
cctaggcgat ctgtgctgtt tgccacggta tgcagcacca gcgcgagatt atgggctcgc      60
acgctcgact gtcggacggg ggcactggaa cgagaagtca ggcgagccgt cacgccctag     120
acaatgccac atcctgagca aataattcaa ccactaaaca aatcaaccgc gtttcccgga     180
```

<210> SEQ ID NO 20
<211> LENGTH: 187
<212> TYPE: DNA
<213> ORGANISM: artificial sequence
<220> FEATURE:
<223> OTHER INFORMATION: promoter

<400> SEQUENCE: 20
cctaggcgat ctgtgctgtt tgccacggta tgcagcacca gcgcgagatt atgggctcgc     60
acgctcgact gtcggacggg ggcactggaa cgagaagtca ggcgagccgt cacgccctgg    120
acaatgccac atcctgagca aataattcaa ccactaaaca aatcaaccgc gtttcccgga    180
ggtaacc                                                              187

<210> SEQ ID NO 21
<211> LENGTH: 187
<212> TYPE: DNA
<213> ORGANISM: artificial sequence
<220> FEATURE:
<223> OTHER INFORMATION: promoter

<400> SEQUENCE: 21
cctaggcgat ctgtgctgtt tgccacggta tgcagcacca gcgcgagatt atgggctcgc     60
acgctcgact gtcggacggg ggcactggaa cgagaagtca ggcgagccgt cacgcccgtg    120
acaatgccac atcctgagca aataattcaa ccactaaaca aatcaaccgc gtttcccgga    180
ggtaacc                                                              187

<210> SEQ ID NO 22
<211> LENGTH: 187
<212> TYPE: DNA
<213> ORGANISM: artificial sequence
<220> FEATURE:
<223> OTHER INFORMATION: promoter

<400> SEQUENCE: 22
cctaggcgat ctgtgctgtt tgccacggta tgcagcacca gcgcgagatt atgggctcgc     60
acgctcgact gtcggacggg ggcactggaa cgagaagtca ggcgagccgt cacgcccatg    120
acaatgccac atcctgagca aataattcaa ccactaaaca aatcaaccgc gtttcccgga    180
ggtaacc                                                              187

<210> SEQ ID NO 23
<211> LENGTH: 187
<212> TYPE: DNA
<213> ORGANISM: artificial sequence
<220> FEATURE:
<223> OTHER INFORMATION: promoter

<400> SEQUENCE: 23
cctaggcgat ctgtgctgtt tgccacggta tgcagcacca gcgcgagatt atgggctcgc     60
acgctcgact gtcggacggg ggcactggaa cgagaagtca ggcgagccgt cacgccctg     120 acaatgccac atcctgagca aataattcaa ccactaaaca aatcaaccgc gtttcccgga    180
ggtaacc                                                              187

<210> SEQ ID NO 24
<211> LENGTH: 187
<212> TYPE: DNA

<213> ORGANISM: artificial sequence
<220> FEATURE:
<223> OTHER INFORMATION: promoter

<400> SEQUENCE: 24
cctaggcgat ctgtgctgtt tgccacggta tgcagcacca gcgcgagatt atgggctcgc     60
acgctcgact gtcggacggg ggcactgaa cgagaagtca ggcgagccgt cacgcccttg    120
agaatgccac atcctgagca aataattcaa ccactaaaca aatcaaccgc gtttcccgga   180
ggtaacc                                                             187

<210> SEQ ID NO 25
<211> LENGTH: 187
<212> TYPE: DNA
<213> ORGANISM: artificial sequence
<220> FEATURE:
<223> OTHER INFORMATION: promoter

<400> SEQUENCE: 25
cctaggcgat ctgtgctgtt tgccacggta tgcagcacca gcgcgagatt atgggctcgc     60
acgctcgact gtcggacggg ggcactgaa cgagaagtca ggcgagccgt cacgcccttg    120
ataatgccac atcctgagca aataattcaa ccactaaaca aatcaaccgc gtttcccgga   180
ggtaacc                                                             187

<210> SEQ ID NO 26
<211> LENGTH: 187
<212> TYPE: DNA
<213> ORGANISM: artificial sequence
<220> FEATURE:
<223> OTHER INFORMATION: promoter

<400> SEQUENCE: 26
cctaggcgat ctgtgctgtt tgccacggta tgcagcacca gcgcgagatt atgggctcgc     60
acgctcgact gtcggacggg ggcactggaa cgagaagtca ggcgagccgt cacgcccttg   120
gcaatgccac atcctgagca aataattcaa ccactaaaca aatcaaccgc gtttcccgga   180
ggtaacc                                                             187

<210> SEQ ID NO 27
<211> LENGTH: 187
<212> TYPE: DNA
<213> ORGANISM: artificial sequence
<220> FEATURE:
<223> OTHER INFORMATION: promoter

<400> SEQUENCE: 27
cctaggcgat ctgtgctgtt tgccacggta tgcagcacca gcgcgagatt atgggctcgc     60
acgctcgact gtcggacggg ggcactggaa cgagaagtca ggcgagccgt cacgcccttg   120
tcaatgccac atcctgagca aataattcaa ccactaaaca aatcaaccgc gtttcccgga   180
ggtaacc                                                             187

<210> SEQ ID NO 28
<211> LENGTH: 187
<212> TYPE: DNA
<213> ORGANISM: artificial sequence
<220> FEATURE:
<223> OTHER INFORMATION: promoter

<400> SEQUENCE: 28
cctaggcgat ctgtgctgtt tgccacggta tgcagcacca gcgcgagatt atgggctcgc     60

```
acgctcgact gtcggacggg ggcactggaa cgagaagtca ggcgagccgt cacgccctttt      120 acaatgccac atcctgagca aataattcaa ccactaaaca aatcaaccgc gtttcccgga      180
ggtaacc                                                                187

<210> SEQ ID NO 29
<211> LENGTH: 1164
<212> TYPE: DNA
<213> ORGANISM: Escherichia coli K-12

<400> SEQUENCE: 29
atgaacaact ttaatctgca cacccccaacc cgcattctgt ttggtaaagg cgcaatcgct       60
ggtttacgcg aacaaattcc tcacgatgct cgcgtattga ttacctacgg cggcggcagc      120
gtgaaaaaaa ccggcgttct cgatcaagtt ctggatgccc tgaaaggcat ggacgtgctg      180
gaatttggcg gtattgagcc aaacccggct tatgaaacgc tgatgaacgc cgtgaaactg      240
gttcgcgaac agaaagtgac tttcctgctg gcggttggcg gcggttctgt actggacggc      300
accaaattta tcgccgcagc ggctaactat ccggaaaata tcgatccgtg cacattctg      360 caaacgggcg gtaaagagat taaaagcgcc atcccgatgg gctgtgtgct gacgctgcca      420
gcaaccggtt cagaatccaa cgcaggcgcg gtgatctccc gtaaaaccac aggcgacaag      480
caggcgttcc attctgccca tgttcagccg gtatttgccg tgctcgatcc ggtttatacc      540 tacacccctgc cgccgcgtca ggtggctaac ggcgtagtgg acgcctttgt acacaccgtg      600
gaacagtatg ttaccaaacc ggttgatgcc aaaattcagg accgtttcgc agaaggcatt      660
ttgctgacgc taatcgaaga tggtccgaaa gccctgaaag agccagaaaa ctacgatgtg      720
cgcgccaacg tcatgtgggc ggcgactcag gcgctgaacg gtttgattgg cgctggcgta      780
ccgcaggact gggcaacgca tatgctgggc cacgaactga ctgcgatgca cggtctggat      840
cacgcgcaaa cactggctat cgtcctgcct gcactgtgga tgaaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa atcatgaca ttacgttgga tgtcagccgc     1140
cgtatatacg aagccgcccg ctaa                                            1164

<210> SEQ ID NO 30
<211> LENGTH: 13470
<212> TYPE: DNA
<213> ORGANISM: artificial sequence
<220> FEATURE:
<223> OTHER INFORMATION: plasmid

<400> SEQUENCE: 30
ccttaagtga gtcgtattac ggactggccg tcgttttaca acgtcgtgac tgggaaaacc       60
ctggcgttac ccaacttaat cgccttgcag cacatccccc tttcgccagc tggcgtaata      120
gcgaagaggc ccgcaccgat cgcccttccc aacagttgcg cagcctgaat ggcgaatggc      180
gcctgatgcg gtattttctc cttacgcatc tgtgcggtat ttcacaccgc atatggtgca      240
ctctcagtac aatctgctct gatgccgcat agttaagcca gccccgacac cgccaacac      300 ccgctgacga gcttagtaaa gccctcgcta gattttaatg cggatgttgc gattacttcg      360
ccaactattg cgataacaag aaaaagccag cctttcatga tatatctccc aatttgtgta      420
```

```
gggcttatta tgcacgctta aaaataataa aagcagactt gacctgatag tttggctgtg      480
agcaattatg tgcttagtgc atctaacgct tgagttaagc cgcgccgcga agcggcgtcg      540
gcttgaacga attgttagac attatttgcc gactaccttg gtgatctcgc ctttcacgta      600
gtggacaaat tcttccaact gatctgcgcg cgaggccaag cgatcttctt cttgtccaag      660
ataagcctgt ctagcttcaa gtatgacggg ctgatactgg gccggcaggc gctccattgc      720
ccagtcggca gcgacatcct tcggcgcgat tttgccggtt actgcgctgt accaaatgcg      780
ggacaacgta agcactacat ttcgctcatc gccagcccag tcgggcggcg agttccatag      840
cgttaaggtt tcatttagcg cctcaaatag atcctgttca ggaaccggat caaagagttc      900
ctccgccgct ggacctacca aggcaacgct atgttctctt gcttttgtca gcaagatagc      960
cagatcaatg tcgatcgtgg ctggctcgaa gatacctgca agaatgtcat tgcgctgcca     1020
ttctccaaat tgcagttcgc gcttagctgg ataacgccac ggaatgatgt cgtcgtgcac     1080
aacaatggtg acttctacag cgcggagaat ctcgctctct ccaggggaag ccgaagtttc     1140
caaaaggtcg ttgatcaaag ctcgccgcgt tgtttcatca agccttacgg tcaccgtaac     1200
cagcaaatca atatcactgt gtggcttcag gccgccatcc actgcggagc cgtacaaatg     1260
tacggccagc aacgtcggtt cgagatggcg ctcgatgacg ccaactacct ctgatagttg     1320
agtcgatact tcggcgatca ccgcttccct catgatgttt aactttgttt tagggcgact     1380
gccctgctgc gtaacatcgt tgctgctcca taacatcaaa catcgaccca cggcgtaacg     1440
cgcttgctgc ttggatgccc gaggcataga ctgtacccca aaaaaacagt cataacaagc     1500
catgaaaacc gccactgcgc cgttaccacc gctgcgttcg gtcaaggttc tggaccagtt     1560
gcgtgagcgc atacgctact tgcattacag cttacgaacc gaacaggctt atgtccactg     1620
ggttcgtgcc ttcatccgtt tccacggtgt gcgtcacccg gcaaccttgg gcagcagcga     1680
agtcgaggca tttctgtcct ggctggcgaa cgagcgcaag gtttcggtct ccacgcatcg     1740
tcaggcattg gcggccttgc tgttcttcta cggcaaggtg ctgtgcacgg atctgccctg     1800
gcttcaggag atcggaagac ctcggccgtc gcggcgcttg ccgtggtgc tgaccccgga     1860 tgaagtggtt cgcatcctcg gttttctgga aggcgagcat cgtttgttcg cccagcttct     1920
gtatggaacg ggcatgcgga tcagtgaggg tttgcaactg cgggtcaagg atctggattt     1980
cgatcacggc acgatcatcg tgcgggaggg caagggctcc aaggatcggg ccttgatgtt     2040
acccgagagc ttggcaccca gcctgcgcga gcagggggaat taattcccac gggttttgct     2100 gccccgcaaac gggctgttct ggtgttgcta gtttgttatc agaatcgcag atccggcttc     2160
agccggtttg ccggctgaaa gcgctatttc ttccagaatt gccatgattt tttccccacg     2220
ggaggcgtca ctggctcccg tgttgtcggc agctttgatt cgataagcag catcgcctgt     2280
ttcaggctgt ctatgtgtga ctgttgagct gtaacaagtt gtctcaggtg ttcaatttca     2340
tgttctagtt gctttgtttt actggtttca cctgttctat taggtgttac atgctgttca     2400
tctgttacat tgtcgatctg ttcatggtga acagctttga atgcaccaaa aactcgtaaa     2460
agctctgatg tatctatctt ttttacaccg ttttcatctg tgcatatgga cagttttccc     2520
tttgatatgt aacggtgaac agttgttcta cttttgtttg ttagtcttga tgcttcactg     2580
atagatacaa gagccataag aacctcgatc ccttccgtat ttagccagta tgttctctag     2640
tgtggttcgt tgttttttgcg tgagccatga gaacgaacca ttgagatcat acttactttg     2700
catgtcactc aaaaattttg cctcaaaact ggtgagctga attttgcag ttaaagcatc     2760 gtgtagtgtt tttcttagtc cgttatgtag gtaggaatct gatgtaatgg ttgttggtat     2820
```

-continued

```
tttgtcacca ttcattttta tctggttgtt ctcaagttcg gttacgagat ccatttgtct    2880
atctagttca acttggaaaa tcaacgtatc agtcgggcgg cctcgcttat caaccaccaa    2940
tttcatattg ctgtaagtgt ttaaatcttt acttattggt tcaaaaccc attggttaag     3000 cctttaaaac tcatggtagt tattttcaag cattaacatg aacttaaatt catcaaggct    3060
aatctctata tttgccttgt gagttttctt ttgtgttagt tcttttaata accactcata    3120
aatcctcata gagtatttgt tttcaaaaga cttaacatgt tccagattat attttatgaa    3180 ttttttaac tggaaaagat aaggcaatat ctcttcacta aaaactaatt ctaattttc      3240 gcttgagaac ttggcatagt ttgtccactg gaaaatctca aagcctttaa ccaaaggatt    3300
cctgatttcc acagttctcg tcatcagctc tctggttgct ttagctaata caccataagc    3360
attttcccta ctgatgttca tcatctgagc gtattggtta aagtgaacg ataccgtccg     3420 ttctttcctt gtagggtttt caatcgtggg gttgagtagt gccacacagc ataaaattag    3480
cttggtttca tgctccgtta agtcatagcg actaatcgct agttcatttg ctttgaaaac    3540
aactaattca gacatacatc tcaattggtc taggtgattt taatcactat accaattgag    3600
atgggctagt caatgataat tactagctag tccttttcct ttgagttgtg ggtatctgta    3660
aattctgcta gacctttgct ggaaaacttg taaattctgc tagaccctct gtaaattccg    3720
ctagaccttt gtgtgttttt tttgtttata ttcaagtggt tataatttat agaataaaga    3780
aagaataaaa aaagataaaa agaatagatc ccagccctgt gtataactca ctactttagt    3840
cagttccgca gtattacaaa aggatgtcgc aaacgctgtt tgctcctcta caaaacagac    3900
cttaaaaccc taaaggctta agtagcaccc tcgcaagctc gggcaaatcg ctgaatattc    3960
cttttgtctc cgaccatcag gcacctgagt cgctgtcttt ttcgtgacat tcagttcgct    4020
gcgctcacgg ctctggcagt gaatgggggt aaatggcact acaggcgcct tttatggatt    4080
catgcaagga aactacccat aatacaagaa aagcccgtca cgggcttctc agggcgtttt    4140
atggcgggtc tgctatgtgg tgctatctga cttttgctg ttcagcagtt cctgccctct     4200 gatttttccag tctgaccact tcggattatc ccgtgacagg tcattcagac tggctaatgc   4260
acccagtaag gcagcggtat catcaacagg cttacccgtc ttactgtcgg gaattcattt    4320
aaatagtcaa aagcctccga ccggaggctt ttgactgcta ggcgatctgt gctgtttgcc    4380
acggtatgca gcaccagcgc gagattatgg gctcgcacgc tcgactgtcg gacggggggca   4440 ctggaacgag aagtcaggcg agccgtcacg cccttgacaa tgccacatcc tgagcaaata    4500
attcaaccac taaacaaatc aaccgcgttt cccggaggta accaagcttg cgggagagaa    4560
tgatgaacaa gagccaacaa gttcagacaa tcaccctggc cgccgcccag caaatggcgg    4620
cggcggtgga aaaaaagcc actgagatca acgtggcggt ggtgttttcc gtagttgacc     4680
gcggaggcaa cacgctgctt atccagcgga tggacgaggc cttcgtctcc agctgcgata    4740
tttccctgaa taaagcctgg agcgcctgca gcctgaagca aggtacccat gaaattacgt    4800
cagcggtcca gccaggacaa tctctgtacg gtctgcagct aaccaaccaa cagcgaatta    4860
ttattttggg cggcggcctg ccagttattt ttaatgagca ggtaattggc gccgtcggcg    4920
ttagcggcgg tacggtcgag caggatcaat tattagccca gtgcgccctg gattgttttt    4980
ccgcattata acctgaagcg agaaggtata ttatgagcta tcgtatgttc cgccaggcat    5040
tctgagtgtt aacagaggga ccgtcatgtc gctttcaccg ccaggcgtac gcctgttta    5100 cgatccgcgc gggcaccatg ccggcgccat caatgagctg tgctgggggc tggaggagca    5160
```

-continued

```
gggggtcccc tgccagacca taacctatga cggaggcggt gacgccgctg cgctgggcgc    5220
cctggcggcc agaagctcgc ccctgcgggt gggtatcggg ctcagcgcgt ccggcgagat    5280
agccctcact catgcccagc tgccggcgga cgcgccgctg gctaccggac acgtcaccga    5340
tagcgacgat caactgcgta cgctcggcgc caacgccggg cagctggtta aagtcctgcc    5400
gttaagtgag agaaactgaa tgtatcgtat ctatacccgc accggggata aaggcaccac    5460
cgccctgtac ggcggcagcc gcatcgagaa agaccatatt cgcgtcgagg cctacggcac    5520
cgtcgatgaa ctgatatccc agctgggcgt ctgctacgcc acgacccgcg acgccgggct    5580
gcgggaaagc ctgcaccata ttcagcagac gctgttcgtg ctgggggctg aactggccag    5640
cgatgcgcgg ggcctgaccc gcctgagcca gacgatcggc gaagaggaga tcaccgccct    5700
ggagcggctt atcgaccgca atatggccga gagcggcccg ttaaaacagt tcgtgatccc    5760
ggggaggaat ctcgcctctg cccagctgca ccctgatgct tgcgcttgaa ctggcctagc    5820
aaacacagaa aaaagcccgc acctgacagt gcgggctttt tttttcctag gcgatctgtg    5880
ctgtttgcca cggtatgcag caccagcgcg agattatggg ctcgcacgct cgactgtcgg    5940
acggggcac tggaacgaga agtcaggcga gccgtcacgc ccttgacaat gccacatcct    6000
gagcaaataa ttcaaccact aaacaaatca accgcgtttc ccggaggtaa ccaagcttca    6060
ccttttgagc cgatgaacaa tgaaaagatc aaaacgattt gcagtactgg cccagcgccc    6120
cgtcaatcag gacgggctga ttggcgagtg gcctgaagag gggctgatcg ccatggacag    6180
cccctttgac ccggtctctt cagtaaaagt ggacaacggt ctgatcgtcg aactggacgg    6240
caaacgccgg gaccagtttg acatgatcga ccgatttatc gccgattacg cgatcaacgt    6300
tgagcgcaca gagcaggcaa tgcgcctgga ggcggtggaa atagcccgta tgctggtgga    6360
tattcacgtc agccgggagg agatcattgc catcactacc gccatcacgc cggccaaagc    6420
ggtcgaggtg atggcgcaga tgaacgtggt ggagatgatg atggcgctgc agaagatgcg    6480
tgcccgccgg acccccctcca accagtgcca cgtcaccaat ctcaaagata atccggtgca    6540
gattgccgct gacgccgccg aggccgggat ccgcggcttc tcagaacagg agaccacggt    6600
cggtatcgcg cgctacgcgc cgtttaacgc cctggcgctg ttggtcggtt cgcagtgcgg    6660
ccgcccggc gtgttgacgc agtgctcggt ggaagaggcc accgagctgg agctgggcat    6720
gcgtggctta accagctacg ccgagacggt gtcggtctac ggcaccgaag cggtatttac    6780
cgacggcgat gatacgccgt ggtcaaaggc gttcctcgcc tcggcctacg cctcccgcgg    6840
gttgaaaatg cgctacacct ccggcaccgg atccgaagcg ctgatgggct attcggagag    6900
caagtcgatg ctctacctcg aatcgcgctg catcttcatt actaaaggcg ccggggttca    6960
gggactgcaa aacggcgcgg tgagctgtat cggcatgacc ggcgctgtgc cgtcgggcat    7020
tcgggcggtg ctggcggaaa acctgatcgc ctctatgctc gacctcgaag tggcgtccgc    7080
caacgaccag actttctccc actcggatat tcgccgcacc cgcgcgcacc ctgatgcagat   7140
gctgccgggc accgacttta ttttctccgg ctacagcgcg gtgccgaact acgacaacat    7200
gttcgccggc tcgaacttcg atgcggaaga ttttgatgat tacaacatcc tgcagcgtga    7260
cctgatggtt gacggcggcc tgcgtccggt gaccgaggcg aaaccattgc cattcgcca    7320
gaaagcggcg cgggcgatcc aggcggtttt ccgcgagctg ggctgccgc caatcgccga    7380
cgaggaggtg gaggccgcca cctacgcgca cggcagcaac gagatgccgc gcgtaacgt    7440
ggtgaggat ctgagtgcgg tggaagagat gatgaagcgc aacatcaccg gcctcgatat    7500
tgtcggcgcg ctgagccgca gcggctttga ggatatcgcc agcaatattc tcaatatgct    7560
```

```
gcgccagcgg gtcaccggcg attacctgca gacctcggcc attctcgatc ggcagttcga    7620
ggtggtgagt gcggtcaacg acatcaatga ctatcagggg ccgggcaccg gctatcgcat    7680
ctctgccgaa cgctgggcgg agatcaaaaa tattccgggc gtggttcagc ccgacaccat    7740
tgaataaggc ggtattcctg tgcaacagac aacccaaatt cagccctctt ttaccctgaa    7800
aacccgcgag ggcggggtag cttctgccga tgaacgcgcc gatgaagtgg tgatcggcgt    7860
cggccctgcc ttcgataaac accagcatca cactctgatc gatatgcccc atggcgcgat    7920
cctcaaagag ctgattgccg gggtggaaga gaggggctt cacgcccggg tggtgcgcat    7980
tctgcgcacg tccgacgtct cctttatggc ctgggatgcg gccaacctga gcggctcggg    8040
gatcggcatc ggtatccagt cgaaggggac acggtcatc catcagcgcg atctgctgcc    8100
gctcagcaac ctggagctgt ctcccaggc gccgctgctg acgctggaga cctaccggca    8160
gattggcaaa aacgctgcgc gctatgcgcg caaagagtca ccttcgccgg tgccggtggt    8220
gaacgatcag atggtgcggc cgaaatttat ggccaaagcc gcgctatttc atatcaaaga    8280
gaccaaacat gtggtgcagg acgccgagcc cgtcaccctg cacatcgact tagtaaggga    8340
gtgaccatga gcgagaaaac catgcgcgtg caggattatc cgttagccac ccgctgcccg    8400
gagcatatcc tgacgcctac cggcaaaacca ttgaccgata ttaccctcga aaggtgctc    8460 tctggcgagg tgggcccgca ggatgtgcgg atctcccgcc agaccttga gtaccaggcg    8520 cagattgccg agcagatgca cgccatgcg gtggcgcgca atttccgccg cgcggcggag    8580
cttatcgcca ttcctgacga cgcattctg gctatctata acgcgctgcg cccgttccgc    8640
tcctcgcagg cggagctgct ggcgatcgcc gacgagctgg agcacacctg gcatgcgaca    8700
gtgaatgccg cctttgtccg gggagtcgcg gaagtgtatc agcagcggca taagctgcgt    8760
aaaggaagct aagcggaggt cagcatgccg ttaatagccg ggattgatat cggcaacgcc    8820
accaccgagt ggcgctggc gtccgactac ccgcaggcga gggcgtttgt tgccagcggg    8880
atcgtcgcga cgacgggcat gaaagggacg cgggacaata tcgccgggac cctcgccgcg    8940
ctggagcagg ccctggcgaa acaccgtgg tcgatgagcg atgtctctcg catctatctt    9000
aacgaagccg cgccggtgat tggcgatgtg gcgatggaga ccatcaccga gaccattatc    9060
accgaatcga ccatgatcgg tcataacccg cagacgccgg gcggggtggg cgttggcgtg    9120
gggacgacta tcgccctcgg gcggctggcg acgctgccgg cggcgcagta tgccgagggg    9180
tggatcgtac tgattgacga cgccgtcgat ttccttgacg ccgtgtggtg gctcaatgag    9240
gcgctcgacc gggggatcaa cgtggtggcg gcgatcctca aaaggacga cggcgtgctg    9300 gtgaacaacc gcctgcgtaa aaccctgccg gtggtggatg aagtgacgct gctggagcag    9360
gtccccgagg gggtaatggc ggcggtggaa gtggccgcgc cgggccaggt ggtgcggatc    9420
ctgtcgaatc cctacgggat cgccaccttc ttcgggctaa gcccggaaga gacccaggcc    9480
atcgtcccca tcgcccgcgc cctgattggc aaccgttccg cggtggtgct caagaccccg    9540 caggggatg tgcagtcgcg ggtgatcccg gcgggcaacc tctacattag cggcgaaaag    9600
cgccgcggag aggccgatgt cgccgagggc gcggaagcca tcatgcaggc gatgagcgcc    9660
tgcgctccgg tacgcgacat ccgcggcgaa ccggcacccc acgccggcgg catgcttgag    9720
cgggtgcgca aggtaatggc gtccctgacc ggccatgaga tgagcgcgat atacatccag    9780
gatctgctgg cggtggatac gtttattccg cgcaaggtgc agggcgggat ggccggcgag    9840
tgcgccatgg agaatgccgt cgggatggcg gcgatggtga aagcggatcg tctgcaaatg    9900
```

```
caggttatcg cccgcgaact gagcgcccga ctgcagaccg aggtggtggt gggcggcgtg    9960
gaggccaaca tggccatcgc cggggcgtta accactcccg gctgtgcggc gccgctggcg   10020
atcctcgacc tcggcgccgg ctcgacggat gcggcgatcg tcaacgcgga ggggcagata   10080
acggcggtcc atctcgccgg ggcggggaat atggtcagcc tgttgattaa aaccgagctg   10140
ggcctcgagg atctttcgct ggcggaagcg ataaaaaaat acccgctggc caaagtggaa   10200
agcctgttca gtattcgtca cgagaatggc gcggtggagt tctttcggga agccctcagc   10260
ccggcggtgt tcgccaaagt ggtgtacatc aaggagggcg aactggtgcc gatcgataac   10320
gccagcccgc tggaaaaaat tcgtctcgtg cgccggcagg cgaaagagaa agtgtttgtc   10380
accaactgcc tgcgcgcgct gcgccaggtc tcacccggcg gttccattcg cgatatcgcc   10440
tttgtggtgc tggtgggcgg ctcatcgctg gactttgaga tcccgcagct tatcacggaa   10500
gccttgtcgc actatggcgt ggtcgccggg cagggcaata ttcggggaac agaagggccg   10560
cgcaatgcgg tcgccaccgg gctgctactg gccggtcagg cgaattaaac gggcgctcgc   10620
gccagcctct aggtacaaat aaaaaaggca cgtcagatga cgtgcctttt ttcttgtcta   10680
gcgtgcacca atgcttctgg cgtcaggcag ccatcggaag ctgtggtatg gctgtgcagg   10740
tcgtaaatca ctgcataatt cgtgtcgctc aaggcgcact cccgttctgg ataatgtttt   10800
ttgcgccgac atcataacgg ttctggcaaa tattctgaaa tgagctgttg acaattaatc   10860
atccggctcg tataatgtgt ggaattgtga gcggataaca atttcacaca ggaaacagac   10920
catgactagt aaggaggaca attccatggc tgctgctgct gatagattaa acttaacttc   10980
cggccacttg aatgctggta gaaagagaag ttcctcttct gtttctttga aggctgccga   11040
aaagcctttc aaggttactg tgattggatc tggtaactgg ggtactacta ttgccaaggt   11100
ggttgccgaa aattgtaagg atacccaga agttttcgct ccaatagtac aaatgtgggt   11160
gttcgaagaa gagatcaatg tgaaaaatt gactgaaatc ataaatacta gacatcaaaa   11220
cgtgaaatac ttgcctggca tcactctacc cgacaatttg gttgctaatc cagacttgat   11280
tgattcagtc aaggatgtcg acatcatcgt ttttcaacatt ccacatcaat ttttgccccg   11340
tatctgtagc caattgaaag gtcatgttga ttcacacgtc agagctatct cctgtctaaa   11400
gggttttgaa gttggtgcta aaggtgtcca attgctatcc tcttacatca ctgaggaact   11460
aggtattcaa tgtggtgctc tatctggtgc taacattgcc accgaagtcg ctcaagaaca   11520
ctggtctgaa acaacagttg cttaccacat tccaaaggat ttcagaggcg agggcaagga   11580
cgtcgaccat aaggttctaa aggccttgtt ccacagacct tacttccacg ttagtgtcat   11640
cgaagatgtt gctggtatct ccatctgtgg tgctttgaag aacgttgttg ccttaggttg   11700
tggtttcgtc gaaggtctag gctggggtaa caacgcttct gctgccatcc aaagagtcgg   11760
tttgggtgag atcatcagat tcggtcaaat gttttttccca gaatctagag aagaaacata   11820
ctaccaagag tctgctggtg ttgctgattt gatcaccacc tgcgctggtg gtagaaacgt   11880
caaggttgct aggctaatgg ctacttctgg taaggacgcc tgggaatgtg aaaaggagtt   11940
gttgaatggc caatccgctc aaggtttaat tacctgcaaa gaagttcacg aatggttgga   12000
aacatgtggc tctgtcgaag acttcccatt atttgaagcc gtataccaaa tcgtttacaa   12060
caactaccca atgaagaacc tgccggacat gattgaagaa ttagatctac atgaagatta   12120
gatttattgg atccaggaaa cagactagaa ttatgggatt gactactaaa cctctatctt   12180
tgaaagttaa cgccgctttg ttcgacgtcg acggtaccat tatcatctct caaccagcca   12240
ttgctgcatt ctggagggat ttcggtaagg acaaaacctta tttcgatgct gaacacgtta   12300
```

```
tccaagtctc gcatggttgg agaacgtttg atgccattgc taagttcgct ccagactttg    12360
ccaatgaaga gtatgttaac aaattagaag ctgaaattcc ggtcaagtac ggtgaaaaat    12420
ccattgaagt cccaggtgca gttaagctgt gcaacgcttt gaacgctcta ccaaaagaga    12480
aatgggctgt ggcaacttcc ggtacccgtg atatggcaca aaaatggttc gagcatctgg    12540
gaatcaggag accaaagtac ttcattaccg ctaatgatgt caaacagggt aagcctcatc    12600
cagaaccata tctgaagggc aggaatggct taggatatcc gatcaatgag caagcccctt    12660
ccaaatctaa ggtagtagta tttgaagacg ctccagcagg tattgccgcc ggaaaagccg    12720
ccggttgtaa gatcattggt attgccacta ctttcgactt ggacttccta aaggaaaaag    12780
gctgtgacat cattgtcaaa aaccacgaat ccatcagagt tggcggctac aatgccgaaa    12840
cagacgaagt tgaattcatt tttgacgact acttatatgc taaggacgat ctgttgaaat    12900
ggtaacccgg gctgcaggca tgcaagcttg gctgttttgg cggatgagag aagattttca    12960
gcctgataca gattaaatca gaacgcagaa gcggtctgat aaaacagaat ttgcctggcg    13020
gcagtagcgc ggtggtccca cctgacccca tgccgaactc agaagtgaaa cgccgtagcg    13080
ccgatggtag tgtggggtct ccccatgcga gagtagggaa ctgccaggca tcaaataaaa    13140
cgaaaggctc agtcgaaaga ctgggccttt cgttttatct gttgtttgtc ggtgaacgct    13200
ctcctgagta ggacaaatcc gccgggagcg atttgaacg ttgcgaagca acggcccgga    13260
gggtggcggg caggacgccc gccataaact gccaggcatc aaattaagca gaaggccatc    13320
ctgacggatg ccttttttgc gtttctacaa actccagctg gatcgggcgc tagagtatac    13380
atttaaatgg taccggcgcg ccgctagctt aattaacgga ccgatgcatg agctcacgcg    13440
taccggtgct cttcgatcta cgtaagaagg                                     13470

<210> SEQ ID NO 31
<211> LENGTH: 42
<212> TYPE: DNA
<213> ORGANISM: artificial sequence
<220> FEATURE:
<223> OTHER INFORMATION: promoter

<400> SEQUENCE: 31
gcccttgact atgccacatc ctgagcaaat aattcaacca ct                        42

<210> SEQ ID NO 32
<211> LENGTH: 42
<212> TYPE: DNA
<213> ORGANISM: artificial sequence
<220> FEATURE:
<223> OTHER INFORMATION: promoter

<400> SEQUENCE: 32
gcccttgacg atgccacatc ctgagcaaat aattcaacca ct                        42

<210> SEQ ID NO 33
<211> LENGTH: 42
<212> TYPE: DNA
<213> ORGANISM: artificial sequence
<220> FEATURE:
<223> OTHER INFORMATION: promoter

<400> SEQUENCE: 33
gcccttgaca atgccacatc ctgagcaaat aattcaacca ct                        42

<210> SEQ ID NO 34
```

```
<211> LENGTH: 81
<212> TYPE: DNA
<213> ORGANISM: artificial sequence
<220> FEATURE:
<223> OTHER INFORMATION: primer

<400> SEQUENCE: 34
cattcggacc ggcccttgac tatgccacat cctgagcaaa taattcaacc actacagcaa     60
agggagcaag taatgaacaa c                                               81

<210> SEQ ID NO 35
<211> LENGTH: 81
<212> TYPE: DNA
<213> ORGANISM: artificial sequence
<220> FEATURE:
<223> OTHER INFORMATION: primer

<400> SEQUENCE: 35
cattcggacc ggcccttgac gatgccacat cctgagcaaa taattcaacc actacagcaa     60
agggagcaag taatgaacaa c                                               81

<210> SEQ ID NO 36
<211> LENGTH: 81
<212> TYPE: DNA
<213> ORGANISM: artificial sequence
<220> FEATURE:
<223> OTHER INFORMATION: primer

<400> SEQUENCE: 36
cattcggacc ggcccttgac aatgccacat cctgagcaaa taattcaacc actacagcaa     60
agggagcaag taatgaacaa c                                               81

<210> SEQ ID NO 37
<211> LENGTH: 82
<212> TYPE: DNA
<213> ORGANISM: artificial sequence
<220> FEATURE:
<223> OTHER INFORMATION: primer

<400> SEQUENCE: 37
cattgagctc aaaaaaaaag cccgcactgt caggtgcggg cttttttctg tgtttaagct     60
tagcgggcgg cttcgtatat ac                                              82

<210> SEQ ID NO 38
<211> LENGTH: 62
<212> TYPE: DNA
<213> ORGANISM: artificial sequence
<220> FEATURE:
<223> OTHER INFORMATION: primer

<400> SEQUENCE: 38
atgtgcgcgc caacgtcatg tgggcggcga ctcaggcgct gagtgtaggc tggagctgct     60
tc                                                                    62

<210> SEQ ID NO 39
<211> LENGTH: 67
<212> TYPE: DNA
<213> ORGANISM: artificial sequence
<220> FEATURE:
<223> OTHER INFORMATION: primer

<400> SEQUENCE: 39
cagacgcgtt cagcatattg cagcagctta gcgcgcttgg tatcgcgatt ccggggatcc     60
``` gtcgacc                                                              67

<210> SEQ ID NO 40
<211> LENGTH: 25
<212> TYPE: DNA
<213> ORGANISM: artificial sequence
<220> FEATURE:
<223> OTHER INFORMATION: primer

<400> SEQUENCE: 40
gccagcaagc ggcaaatctc ttcac                                          25

<210> SEQ ID NO 41
<211> LENGTH: 25
<212> TYPE: DNA
<213> ORGANISM: artificial sequence
<220> FEATURE:
<223> OTHER INFORMATION: primer

<400> SEQUENCE: 41
gaggcgtaaa aagcttagcg ggcgg                                          25

<210> SEQ ID NO 42
<211> LENGTH: 24
<212> TYPE: DNA
<213> ORGANISM: artificial sequence
<220> FEATURE:
<223> OTHER INFORMATION: primer

<400> SEQUENCE: 42
gcttcctcgt gctttacggt atcg                                           24

<210> SEQ ID NO 43
<211> LENGTH: 23
<212> TYPE: DNA
<213> ORGANISM: artificial sequence
<220> FEATURE:
<223> OTHER INFORMATION: primer

<400> SEQUENCE: 43
cctgcgtgca atccatcttg ttc                                            23

<210> SEQ ID NO 44
<211> LENGTH: 100
<212> TYPE: DNA
<213> ORGANISM: artificial sequence
<220> FEATURE:
<223> OTHER INFORMATION: primer

<400> SEQUENCE: 44 cgattttta acatttccat aagttacgct tatttaaagc gtcgtgaatt taatgacgta     60
aattcctgct atttattcgt gtgtaggctg gagctgcttc                         100

<210> SEQ ID NO 45
<211> LENGTH: 100
<212> TYPE: DNA
<213> ORGANISM: artificial sequence
<220> FEATURE:
<223> OTHER INFORMATION: primer

<400> SEQUENCE: 45
tcgcattggc gcgaatatgc tcgggctttg cttttcgtca gtggttgaat tatttgctca    60
ggatgtggca ttgtcaaggg catatgaata tcctccttag                         100

<210> SEQ ID NO 46
<211> LENGTH: 30
<212> TYPE: DNA
<213> ORGANISM: artificial sequence
<220> FEATURE:
<223> OTHER INFORMATION: primer

<400> SEQUENCE: 46
gcggaatatt gttcgttcat attaccccag					30

<210> SEQ ID NO 47
<211> LENGTH: 94
<212> TYPE: DNA
<213> ORGANISM: artificial sequence
<220> FEATURE:
<223> OTHER INFORMATION: terminator

<400> SEQUENCE: 47
agcttaggag tctagaatat tgagctcgaa ttcccgggca tgcggtaccg gatccagaaa			60 aaagcccgca cctgacagtg cgggcttttt tttt					94

<210> SEQ ID NO 48
<211> LENGTH: 12145
<212> TYPE: DNA
<213> ORGANISM: artificial sequence
<220> FEATURE:
<223> OTHER INFORMATION: plasmid

<400> SEQUENCE: 48
gtcgaccacc acgtggtga ctttaatgcc gctctcatgc agcagctcgg tggcggtctc			60 aaaattcagg atgtcgccgg tatagttttt gataatcagc aagacgcctt cgccgccgtc			120 aatttgcatc gcgcattcaa acattttgtc cggcgtcggc gaggtgaata tttcccccgg			180 acaggcgccg gagagcatgc cctggccgat atagccgcag tgcatcggtt catgtccgct			240 gccgccgccg gagagcaggg ccaccttgcc agccaccggc gcgtcggtgc gggtcacata			300 cagcgggtcc tgatgcaggg tcagctgcgg atgggcttta gccagcccct gtaattgttc			360 attcagtaca tcttcaacac ggttaatcag ctttttcatt attcagtgct ccgttggaga			420 aggttcgatg ccgcctctct gctggcgag gcggtcatcg cgtaggggta tcgtctgacg			480 gtggagcgtg cctggcgata tgatgattct ggctgagcgg acgaaaaaaa gaatgccccg			540 acgatcgggt tcattacga acattgctt cctgattttg tttctttatg aacgttttt			600 gctgaggata tggtgaaaat gcgagctggc gcgcttttt tcttctgcca taagcggcgg			660 tcaggatagc cggcgaagcg ggtgggaaaa aattttttgc tgattttctg ccgactgcgg			720 gagaaaaggc ggtcaaacac ggaggattgt aagggcatta tgcggcaaag gagcggatcg			780 ggatcgcaat cctgacagag actagggttt tttgttccaa tatggaacgt aaaaaattaa			840 cctgtgtttc atatcagaac aaaaaggcga agatttttt tgttccctgc ggccctaca			900 gtgatcgcac tgctccggta cgctccgttc aggccgcgct tcactggccg gcgcggataa			960 cgccagggct catcatgtct acatgcgcac ttatttgagg gtgaaaggaa tgctaaaagt			1020 tattcaatct ccagccaaat atcttcaggg tcctgatgct gctgttctgt cggtcaata			1080 tgccaaaaac ctggcggaga gcttcttcgt catcgctgac gatttcgtaa tgaagctggc			1140 gggagagaaa gtggtgaatg gcctgcagag ccacgatatt cgctgccatg cggaacggtt			1200 taacggcgaa tgcagccatg cggaaatcaa ccgtctgatg gcgattttgc aaaaacaggg			1260 ctgccgcggc gtggtcggga tcggcggtgg taaaaccctc gataccgcga aggcgatcgg			1320

```
ttactaccag aagctgccgg tggtggtgat cccgaccatc gcctcgaccg atgcgccaac   1380
cagcgcgctg tcggtgatct acaccgaagc gggcgagttt gaagagtatc tgatctatcc   1440
gaaaaacccg atatggtgg tgatggacac ggcgattatc gccaaagcgc cggtacgcct   1500
gctggtctcc ggcatgggcg atgcgctctc cacctggttc gaggccaaag cttgctacga   1560
tgcgcgcgcc accagcatgg ccggaggaca gtccaccgag gcggcgctga gcctcgcccg   1620
cctgtgctat gatacgctgc tggcggaggg cgaaaaggcc cgtctggcgg cgcaggccgg   1680
ggtagtgacc gaagcgctgg agcgcatcat cgaggcgaac acttacctca gcggcattgg   1740
ctttgaaagc agtggcctgg ccgctgccca tgcaatccac aacggtttca ccattcttga   1800
agagtgccat cacctgtatc acggtgagaa agtggccttc ggtaccctgg cgcagctggt   1860
gctgcagaac agcccgatgg acgagattga acggtgcag ggcttctgcc agcgcgtcgg   1920
cctgccggtg acgctcgcgc agatgggcgt caaagagggg atcgacgaga aaatcgccgc   1980
ggtggcgaaa gctacctgcg cggaagggga aaccatccat aatatgccgt tgcggtgac   2040
cccggagagc gtccatgccg ctatcctcac cgccgatctg ttaggccagc agtggctggc   2100
gcgttaattc gcggtggcta aaccgctggc ccaggtcagc ggttttttctt tctcccctcc   2160
ggcagtcgct gccggaggg ttctctatgg tacaacgcgg aaaaggatat gactgttcag   2220
actcaggata ccgggaaggc ggtctcttcc gtcattgccc agtcatggca ccgctgcagc   2280
aagtttatgc agcgcgaaac ctggcaaacg ccgcaccagg cccagggcct gaccttcgac   2340
tccatctgtc ggcgtaaaac cgcgctgctc accatcggcc aggcggcgct ggaagacgcc   2400
tgggagttta tggacggccg cccctgcgcg ctgtttattc ttgatgagtc cgcctgcatc   2460
ctgagccgtt gcgcgagcc gcaaaccctg gcccagctgg ctgccctggg atttcgcgac   2520
ggcagctatt gtgcggagag cattatcggc acctgcgcgc tgtcgctggc cgcgatgcag   2580
ggccagccga tcaacaccgc cggcgatcgg cattttaagc aggcgctaca gccatggagt   2640
ttttgctcga cgccggtgtt tgataaccac gggcggctgt tcggctctat ctcgctttgc   2700
tgtctggtcg agcaccagtc cagcgccgac ctctccctga cgctggccat cgcccgcgag   2760
gtgggtaact ccctgcttac cgacagcctg ctggcggaat ccaaccgtca cctcaatcag   2820
atgtacggcc tgctggagag catggacgat ggggtgatgg cgtggaacga cagggcgtg   2880
ctgcagtttc tcaatgttca ggcggcgaga ctgctgcatc ttgatgctca ggccagccag   2940
gggaaaaata tcgccgatct ggtgaccctc ccggcgctgc tgcgccgcgc catcaaacac   3000
gcccgcggcc tgaatcacgt cgaagtcacc tttgaaagtc agcatcagtt tgtcgatgcg   3060
gtgatcacct aaaaccgat tgtcgaggcg caaggcaaca gttttattct gctgctgcat   3120
ccggtggagc agatgcggca gctgatgacc agccagctcg gtaaagtcag ccacaccttt   3180
gagcagatgt ctgccgacga tccggaaacc cgacgcctga tccactttgg ccgcaggcg   3240
gcgcgcggcg gcttcccggt gctactgtgc ggcgaagagg gggtcgggaa agagctgctg   3300
agccaggcta ttcacaatga aagcgaacgg cgggcggcc cctacatctc cgtcaactgc   3360
cagctatatg ccgacagcgt gctgggccag gactttatgg gcagcgcccc taccgacgat   3420
gaaaatggtc gcctgagccg ccttgagctg gccaacggcg gcaccctgtt tctgaaaag   3480
atcgagtatc tggcgccgga gctgcagtcg gctctgctgc aggtgattaa gcagggcgtg   3540
ctcacccgcc tcgacgcccg cgcgcctgatc ccggtggatg tgaaggtgat tgccaccacc   3600
accgtcgatc tggccaatct ggtggaacag aaccgcttta gccgcagct gtactatgcg   3660
```

```
ctgcactcct tgagatcgt catcccgccg ctgcgcgccc gacgcaacag tattccgtcg    3720
ctggtgcata accggttgaa gagcctggag aagcgtttct cttcgcgact gaaagtggac    3780
gatgacgcgc tggcacagct ggtggcctac tcgtggccgg ggaatgattt tgagctcaac    3840
agcgtcattg agaatatcgc catcagcagc gacaacggcc acattcgcct gagtaatctg    3900
ccggaatatc tcttttccga gcggccgggc ggggatagcg cgtcatcgct gctgccggcc    3960
agcctgactt ttagcgccat cgaaaaggaa gctattattc acgccgcccg ggtgaccagc    4020
gggcgggtgc aggagatgtc gcagctgctc aatatcggcc gcaccaccct gtggcgcaaa    4080
atgaagcagt acgatattga cgccagccag ttcaagcgca agcatcaggc ctagtctctt    4140
cgattcgcgc catggagaac agggcatccg acaggcgatt gctgtagcgt ttgagcgcgt    4200
cgcgcagcgc atgcgcgcgg tccatggccg tcagcaggcg ttcgagccga cgggactggg    4260
tgcgcgccac gtgcagctgg gcagaggcga gattcctccc cgggatcacg aactgtttta    4320
acgggccgct ctcggccata ttgcggtcga taagccgctc cagggcggtg atctcctctt    4380
cgccgatcgt ctggctcagg cgggtcaggc cccgcgcatc gctggccagt tcagccccca    4440
gcacgaacag cgtctgctga atatggtgca ggctttcccg cagcccggcg tcgcgggtcg    4500
tggcgtagca gacgcccagc tgggatatca gttcatcgac ggtgccgtag gcctcgacgc    4560
gaatatggtc tttctcgatg cggctgccgc cgtacagggc ggtggtgcct ttatcccgg    4620 tgcgggtata gatacgatac attcagtttc tctcacttaa cggcaggact ttaaccagct    4680
gcccggcgtt ggcgccgagc gtacgcagtt gatcgtcgct atcggtgacg tgtccggtag    4740
ccagcggcgc gtccgccggc agctgggcat gagtgagggc tatctcgccg gacgcgctga    4800
gcccgatacc cacccgcagg ggcgagcttc tggccgccag ggcgcccagc gcagcggcgt    4860
caccgcctcc gtcataggtt atggtctggc aggggacccc ctgctcctcc agcccccagc    4920
acagctcatt gatggcgccg gcatggtgcc gcgcgcggatc gtaaaacagg cgtacgcctg    4980
gcggtgaaag cgacatgacg gtcccctcgt taacactcag aatgcctggc ggaaaatcgc    5040
ggcaatctcc tgctcgttgc ctttacgcgg gttcgagaac gcattgccgt cttttagagc    5100
catctccgcc atgtagggga gtcggcctc ttttaccccc agatcgcgca gatgctgcgg    5160
aataccgata tccatcgaca gacgcgtgat agcggcgatg gcttttccg ccgcgtcgag    5220 agtggacagt ccggtgatat tttcgcccat cagttcagcg atatcggcga atttctccgg    5280
gttggcgatc aggttgtagc gcgccacatg cggcagcagg acagcgttgg ccacgccgtg    5340
cggcatgtcg tacaggccgc ccagctgtg cgccatggcg tgcacgtagc cgaggttggc    5400
gttattgaaa gccatcccgg ccagcagaga agcataggcc atgttttccc gcgcctgcag    5460
attgctgccg agggccacgg cctggcgcag gttgcgggcg atgaggcgga tcgcctgcat    5520
ggcggcggcg tccgtcaccg ggttagcgtc tttggagata taggcctcta cggcgtgggt    5580
cagggcatcc atcccggtcg ccgcggtcag ggcggccggt ttaccgatca tcagcagtgg    5640
atcgttgata gagaccgacg gcagtttgcg ccagctgacg atcacaaact tcactttggt    5700
ttcggtgttg tcaggacgc agtggcgggt gacctcgctg gcggtgccgg cggtggtatt    5760
gaccgcgacg ataggcggca gcgggttggt cagggtctcg attccggcat actggtacag    5820
atcgccctca tgggtggcgg cgatgccgat gcctttgccg caatcgtgcg ggctgccgcc    5880
gcccacggtg acgatgatgt cgcactgttc gcggcgaaac acggcgaggc cgtcgcgcac    5940
gttggtgtct tcgggttcg gctcgacgcc gtcaaagatc gccacctcga tcccggcctc    6000
ccgcagataa tgcagggttt tgtccaccgc gccatcttta attgcccgca ggccttgtc    6060
```

```
ggtgaccagc agggcttttt tcccccccag cagctggcag cgttcgccga ctacggaaat   6120
ggcgttgggg ccaaaaaagt taacgtttgg caccagataa tcaaacatac gatagctcat   6180
aatataccttc ctcgcttcag gttataatgc ggaaaaacaa tccagggcgc actgggctaa   6240
taattgatcc tgctcgaccg taccgccgct aacgccgacg cgccaatta cctgctcatt    6300
aaaaataact ggcaggccgc cgccaaaaat aataattcgc tgttggttgg ttagctgcag   6360
accgtacaga gattgtcctg ctggaccgc tgacgtaatt tcatgggtac cttgcttcag    6420
gctgcaggcg ctccaggctt tattcaggga aatatcgcag ctggagacga aggcctcgtc   6480
catccgctgg ataagcagcg tgttgcctcc gcggtcaact acgaaaaaca ccaccgccac   6540
gttgatctca gtggcttttt tttccaccgc cgccgccatt tgctgggcgg cggcagggt    6600
gattgtctga acttgttggc tcttgttcat cattctctcc cgcaccagga taacgctggc   6660
gcgaatagtc agtaggggc gatagtaaaa aactattacc attcggttgg cttgctttat    6720
ttttgtcagc gttattttgt cgcccgccat gatttagtca ataggttaa aatagcgtcg    6780
gaaaaacgta attaagggcg ttttttatta attgatttat atcattgcgg gcgatcacat   6840
tttttatttt tgccgccgga gtaaagtttc atagtgaaac tgtcggtaga tttcgtgtgc   6900
caaattgaaa cgaaattaaa tttatttttt tcaccactgg ctcatttaaa gttccgctat   6960
tgccggtaat ggccgggcgg caacgacgct ggcccggcgt attcgctacc gtctgcggat   7020
ttcaccttt gagccgatga acaatgaaaa gatcaaaacg atttgcagta ctggcccagc    7080
gccccgtcaa tcaggacggg ctgattggcg agtggcctga agaggggctg atcgccatgg   7140
acagccccttt tgacccggtc tcttcagtaa aagtggacaa cggtctgatc gtcgaactgg  7200
acggcaaacg ccgggaccag tttgacatga tcgaccgatt tatcgccgat tacgcgatca   7260
acgttgagcg cacagagcag gcaatgcgcc tggaggcggt ggaaatagcc cgtatgctgg   7320
tggatattca cgtcagccgg gaggagatca ttgccatcac taccgccatc acgccggcca   7380
aagcggtcga ggtgatggcg cagatgaacg tggtggagat gatgatggcg ctgcagaaga   7440
tgcgtgcccg ccgacccccc tccaaccagt gccacgtcac caatctcaaa gataatccgg   7500
tgcagattgc cgctgacgcc gccgaggccg ggatccgcgg cttctcagaa caggagacca   7560
cggtcggtat cgcgcgctac gcgccgttta acgccctggc gctgttggtc ggttcgcagt   7620
gcggccgccc cggcgtgttg acgcagtgct cggtggaaga ggccaccgag ctggagctgg   7680
gcatgcgtgc cttaaccagc tacgccgaga cggtgtcggt ctacggcacc gaagcggtat   7740
ttaccgacgg cgatgatacg ccgtggtcaa aggcgttcct cgcctcggcc tacgcctccc   7800
gcgggttgaa aatgcgctac acctccggca ccggatccga agcgctgatg gctattcgg    7860
agagcaagtc gatgctctac ctcgaatcgc gctgcatctt cattactaaa ggcgccgggg   7920
ttcagggact gcaaaacggc gcggtgagct gtatcggcat gaccggcgct gtgccgtcgg   7980
gcattcgggc ggtgctggcg gaaaacctga tcgcctctat gctcgacctc gaagtggcgt   8040
ccgccaacga ccagactttc tcccactcgg atattcgccg caccgcgcgc accctgatgc   8100
agatgctgcc gggcaccgac tttatttttct ccggctacag cgcggtgccg aactacgaca   8160
acatgttcgc cggctcgaac ttcgatgcgg aagattttga tgattacaac atcctgcagc   8220
gtgacctgat ggttgacggc ggcctgcgtc cggtgaccga ggcggaaacc attgccattc   8280
gccagaaagc ggcgcgggcg atccaggcgg ttttccgcga gctggggctg ccgccaatcg   8340
ccgacgagga ggtggaggcc gccacctacg cgcacggcag caacgagatg ccgccgcgta   8400
```

```
acgtggtgga ggatctgagt gcggtggaag agatgatgaa gcgcaacatc accggcctcg   8460
atattgtcgg cgcgctgagc cgcagcggct ttgaggatat cgccagcaat attctcaata   8520
tgctgcgcca gcgggtcacc ggcgattacc tgcagacctc ggccattctc gatcggcagt   8580
tcgaggtggt gagtgcggtc aacgacatca atgactatca ggggccgggc accggctatc   8640
gcatctctgc cgaacgctgg gcggagatca aaaatattcc gggcgtggtt cagcccgaca   8700
ccattgaata aggcggtatt cctgtgcaac agacaaccca aattcagccc tcttttaccc   8760
tgaaaacccg cgagggcggg gtagcttctg ccgatgaacg cgccgatgaa gtggtgatcg   8820
gcgtcggccc tgccttcgat aaacaccagc atcacactct gatcgatatg ccccatggcg   8880
cgatcctcaa agagctgatt gccggggtgg aagaagaggg gcttcacgcc cgggtggtgc   8940
gcattctgcg cacgtccgac gtctccttta tggcctggga tgcggccaac ctgagcggct   9000
cggggatcgg catcggtatc cagtcgaagg ggaccacggt catccatcag cgcgatctgc   9060
tgccgctcag caacctggag ctgttctccc aggcgccgct gctgacgctg gagacctacc   9120
ggcagattgg caaaaacgct gcgcgctatg cgcgcaaaga gtcaccttcg ccggtgccgg   9180
tggtgaacga tcagatggtg cggccgaaat ttatggccaa agccgcgcta tttcatatca   9240
aagagaccaa acatgtggtg caggacgccg agcccgtcac cctgcacatc gacttagtaa   9300
gggagtgacc atgagcgaga aaaccatgcg cgtgcaggat tatccgttag ccacccgctg   9360
cccggagcat atcctgacgc ctaccggcaa accattgacc gatattaccc tcgagaaggt   9420
gctctctggc gaggtgggcc gcaggatgt gcggatctcc cgccagaccc ttgagtacca   9480
ggcgcagatt gccgagcaga tgcagcgcca tgcggtggcg cgcaatttcc gccgcgcggc   9540
ggagcttatc gccattcctg acgagcgcat tctggctatc tataacgcgc tgcgcccgtt   9600
ccgctcctcg caggcggagc tgctggcgat cgccgacgag ctggagcaca cctggcatgc   9660
gacagtgaat gccgcctttg tccgggagtc ggcggaagtg tatcagcagc ggcataagct   9720
gcgtaaagga agctaagcgg aggtcagcat gccgttaata gccggattg atatcggcaa   9780
cgccaccacc gaggtggcgc tggcgtccga ctacccgcag gcgagggcgt ttgttgccag   9840
cgggatcgtc gcgacgacgg gcatgaaagg gacgcgggac aatatcgccg ggaccctcgc   9900
cgcgctggag caggccctgg cgaaaacacc gtggtcgatg agcgatgtct ctcgcatcta   9960
tcttaacgaa gccgcgccgg tgattggcga tgtggcgatg gagaccatca ccgagaccat  10020
tatcaccgaa tcgaccatga tcggtcataa cccgcagacg ccgggcgggg tgggcgttgg  10080
cgtggggacg actatcgccc tcgggcggct ggcgacgctg ccggcggcgc agtatgccga  10140
ggggtggatc gtactgattg acgacgccgt cgatttcctt gacgccgtgt ggtggctcaa  10200
tgaggcgctc gaccgggga tcaacgtggt ggcggcgatc ctcaaaaagg acgacggcgt  10260
gctggtgaac aaccgcctgc gtaaaaccct gccggtggtg gatgaagtga cgctgctgga  10320
gcaggtcccc gagggggtaa tggcggcggt ggaagtggcc gcgccgggcc aggtggtgcg  10380
gatcctgtcg aatccctacg ggatcgccac cttcttcggg ctaagcccgg aagagaccca  10440
ggccatcgtc cccatcgccc gcgccctgat tggcaaccgt tccgcggtgg tgctcaagac  10500
cccgcagggg gatgtgcagt cgcgggtgat cccggcgggc aacctctaca ttagcggcga  10560
aaagcgccgc ggagaggccg atgtcgccga gggcgcggaa gccatcatgc aggcgatgag  10620
cgcctgcgct ccggtacgcg acatccgcgg cgaaccgggc acccacgccg cggcatgct  10680
tgagcgggtg cgcaaggtaa tggcgtccct gaccggccat gagatgagcg cgatatacat  10740
ccaggatctg ctggcggtgg atacgtttat tccgcgcaag gtgcagggcg ggatggccgg  10800
```

```
cgagtgcgcc atgagaatg ccgtcgggat ggcggcgatg gtgaaagcgg atcgtctgca   10860
aatgcaggtt atcgcccgcg aactgagcgc ccgactgcag accgaggtgg tggtgggcgg   10920
cgtggaggcc aacatggcca tcgccggggc gttaaccact ccgggctgtg cggcgccgct   10980
ggcgatcctc gacctcggcg ccggctcgac ggatgcggcg atcgtcaacg cggaggggca   11040
gataacggcg gtccatctcg ccggggcggg gaatatggtc agcctgttga ttaaaaccga   11100
gctgggcctc gaggatcttt cgctggcgga agcgataaaa aaatacccgc tggccaaagt   11160
ggaaagcctt ttcagtattc gtcacgagaa tggcgcggtg gagttctttc gggaagccct   11220
cagcccggcg gtgttcgcca agtggtgta catcaaggag ggcgaactgg tgccgatcga   11280
taacgccagc ccgctggaaa aaattcgtct cgtgcgccgg caggcgaaag agaaagtgtt   11340
tgtcaccaac tgcctgcgcg cgctgcgcca ggtctcaccc ggcggttcca ttcgcgatat   11400
cgcctttgtg gtgctggtgg gcggctcatc gctggacttt gagatcccgc agcttatcac   11460
ggaagccttg tcgcactatg gcgtggtcgc cgggcagggc aatattcggg aacagaagg    11520
gccgcgcaat gcggtcgcca ccgggctgct actggccggt caggcgaatt aaacgggcgc   11580
tcgcgccagc ctctctcttt aacgtgctat ttcaggatgc cgataatgaa ccagacttct   11640
accttaaccg ggcagtgcgt ggccgagttt cttggcaccg gattgctcat tttcttcggc   11700
gcgggctgcg tcgctgcgct gcgggtcgcc ggggccagct ttggtcagtg ggagatcagt   11760
attatctggg gccttggcgt cgccatggcc atctacctga cggccggtgt ctccggcgcg   11820
cacctaaatc cggcggtgac cattgccctg tggctgttcg cctgttttga acgccgcaag   11880
gtgctgccgt ttattgttgc ccagacggcc ggggccttct gcgccgccgc gctggtgtat   11940
gggctctatc gccagctgtt tctcgatctt gaacagagtc agcatatcgt gcgcggcact   12000
gccgccagtc ttaacctggc cggggtcttt tccacgtacc cgcatccaca tatcactttt   12060
atacaagcgt ttgccgtgga gaccaccatc acggcaatcc tgatggcgat gatcatggcc   12120
ctgaccgacg acggcaacgg aattc                                        12145
```

<210> SEQ ID NO 49
<211> LENGTH: 37
<212> TYPE: DNA
<213> ORGANISM: artificial sequence
<220> FEATURE:
<223> OTHER INFORMATION: primer

<400> SEQUENCE: 49
ggaattcaga tctcagcaat gagcgagaaa accatgc                          37

<210> SEQ ID NO 50
<211> LENGTH: 27
<212> TYPE: DNA
<213> ORGANISM: artificial sequence
<220> FEATURE:
<223> OTHER INFORMATION: primer

<400> SEQUENCE: 50
gctctagatt agcttccttt acgcagc                                     27

<210> SEQ ID NO 51
<211> LENGTH: 33
<212> TYPE: DNA
<213> ORGANISM: artificial sequence
<220> FEATURE:
<223> OTHER INFORMATION: primer

```
<400> SEQUENCE: 51
ggccaagctt aaggaggtta attaaatgaa aag                              33

<210> SEQ ID NO 52
<211> LENGTH: 26
<212> TYPE: DNA
<213> ORGANISM: artificial sequence
<220> FEATURE:
<223> OTHER INFORMATION: primer

<400> SEQUENCE: 52
gctctagatt attcaatggt gtcggg                                     26

<210> SEQ ID NO 53
<211> LENGTH: 26
<212> TYPE: DNA
<213> ORGANISM: artificial sequence
<220> FEATURE:
<223> OTHER INFORMATION: primer

<400> SEQUENCE: 53
gctctagatt attcaatggt gtcggg                                     26

<210> SEQ ID NO 54
<211> LENGTH: 42
<212> TYPE: DNA
<213> ORGANISM: artificial sequence
<220> FEATURE:
<223> OTHER INFORMATION: primer

<400> SEQUENCE: 54
gcgccgtcta gaattatgag ctatcgtatg tttgattatc tg                   42

<210> SEQ ID NO 55
<211> LENGTH: 18
<212> TYPE: DNA
<213> ORGANISM: artificial sequence
<220> FEATURE:
<223> OTHER INFORMATION: primer

<400> SEQUENCE: 55
tcgacgaatt caggagga                                              18

<210> SEQ ID NO 56
<211> LENGTH: 18
<212> TYPE: DNA
<213> ORGANISM: artificial sequence
<220> FEATURE:
<223> OTHER INFORMATION: primer

<400> SEQUENCE: 56
ctagtcctcc tgaattcg                                              18

<210> SEQ ID NO 57
<211> LENGTH: 133
<212> TYPE: DNA
<213> ORGANISM: artificial sequence
<220> FEATURE:
<223> OTHER INFORMATION: fragment

<400> SEQUENCE: 57
agtcaaaagc ctccgaccgg aggcttttga ctgctagcaa acacagaaaa aagcccgcac    60
ctgacagtgc gggcttttttt tttcctaggt acaaataaaa aaggcacgtc agatgacgtg   120 cctttttttct tgt                                                     133
```

<210> SEQ ID NO 58
<211> LENGTH: 100
<212> TYPE: DNA
<213> ORGANISM: artificial sequence
<220> FEATURE:
<223> OTHER INFORMATION: primer

<400> SEQUENCE: 58
ggaattcatt taaatagtca aaagcctccg accggaggct tttgactgct agcaaacaca     60
gaaaaaagcc cgcacctgac agtgcgggct tttttttcc                          100

<210> SEQ ID NO 59
<211> LENGTH: 100
<212> TYPE: DNA
<213> ORGANISM: artificial sequence
<220> FEATURE:
<223> OTHER INFORMATION: primer

<400> SEQUENCE: 59
ggggtaccat ttaaatgtat actctagaca agaaaaaagg cacgtcatct gacgtgcctt     60
ttttatttgt acctaggaaa aaaaaagccc gcactgtcag                          100

<210> SEQ ID NO 60
<211> LENGTH: 175
<212> TYPE: DNA
<213> ORGANISM: artificial sequence
<220> FEATURE:
<223> OTHER INFORMATION: fragment

<400> SEQUENCE: 60
ggaattcatt taaatagtca aaagcctccg accggaggct tttgactgct agcaaacaca     60
gaaaaaagcc cgcacctgac agtgcgggct tttttttcc taggtacaaa taaaaaaggc    120
acgtcagatg acgtgccttt tttcttgtct agagtataca tttaaatggt acccc        175

<210> SEQ ID NO 61
<211> LENGTH: 20
<212> TYPE: DNA
<213> ORGANISM: artificial sequence
<220> FEATURE:
<223> OTHER INFORMATION: primer

<400> SEQUENCE: 61
ggaattcatt taaatagtca                                                 20

<210> SEQ ID NO 62
<211> LENGTH: 20
<212> TYPE: DNA
<213> ORGANISM: artificial sequence
<220> FEATURE:
<223> OTHER INFORMATION: primer

<400> SEQUENCE: 62
ggggtaccat ttaaatgtat                                                 20

<210> SEQ ID NO 63
<211> LENGTH: 21
<212> TYPE: DNA
<213> ORGANISM: artificial sequence
<220> FEATURE:
<223> OTHER INFORMATION: primer

<400> SEQUENCE: 63

-continued

```
gacgcaacag tattccgtcg c                                        21
```

<210> SEQ ID NO 64
<211> LENGTH: 42
<212> TYPE: DNA
<213> ORGANISM: artificial sequence
<220> FEATURE:
<223> OTHER INFORMATION: primer

<400> SEQUENCE: 64

```
atgagctatc gtatgttccg ccaggcattc tgagtgttaa cg                 42
```

<210> SEQ ID NO 65
<211> LENGTH: 33
<212> TYPE: DNA
<213> ORGANISM: artificial sequence
<220> FEATURE:
<223> OTHER INFORMATION: primer

<400> SEQUENCE: 65

```
gcctggcgga acatacgata gctcataata tac                           33
```

<210> SEQ ID NO 66
<211> LENGTH: 21
<212> TYPE: DNA
<213> ORGANISM: artificial sequence
<220> FEATURE:
<223> OTHER INFORMATION: primer

<400> SEQUENCE: 66

```
cggggcgctg ggccagtact g                                        21
```

<210> SEQ ID NO 67
<211> LENGTH: 53
<212> TYPE: DNA
<213> ORGANISM: artificial sequence
<220> FEATURE:
<223> OTHER INFORMATION: linker

<400> SEQUENCE: 67

```
tctagaggat ccgctagcac tagtagcccg ggcgctagcg cggccgcccc ggg     53
```

<210> SEQ ID NO 68
<211> LENGTH: 37
<212> TYPE: DNA
<213> ORGANISM: artificial sequence
<220> FEATURE:
<223> OTHER INFORMATION: primer

<400> SEQUENCE: 68

```
tattcagctg gctagcgtgc accaatgctt ctggcgt                       37
```

<210> SEQ ID NO 69
<211> LENGTH: 35
<212> TYPE: DNA
<213> ORGANISM: artificial sequence
<220> FEATURE:
<223> OTHER INFORMATION: primer

<400> SEQUENCE: 69

```
gatccagctg gagtttgtag aaacgcaaaa aggcc                         35
```

<210> SEQ ID NO 70
<211> LENGTH: 7283
<212> TYPE: DNA
<213> ORGANISM: artificial sequence
<220> FEATURE:
<223> OTHER INFORMATION: plasmid

<400> SEQUENCE: 70

```
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct      300
tccaactgat ctgcgcgcga ggccaagcga tcttcttct gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caatcaata     900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga cccggatga agtggttcgc    1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
```

```
ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
atttttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagaccttt    3360
gctggaaaac ttgtaaattc tgctagaccc tctgtaaatt ccgctagacc tttgtgtgtt    3420 tttttgttt atattcaagt ggttataatt tatagaataa agaaagaata aaaaaagata    3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc    3720
agtgaatggg ggtaaatggc actacaggcg cctttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattcg cgttggccga ttcattaatg    4020
cagctggcac gacaggtttc ccgactggaa agcgggcagt gagcgcaacg caattaatgt    4080
gagttagctc actcattagg caccccaggc tttacacttt atgcttccgg ctcgtatgtt    4140
gtgtggaatt gtgagcggat aacaatttca cacaggaaac agctatgacc atgattacgc    4200
caagcttgca tgcctgcagg tcgactctag aggatccgct agcactagta gccctattca    4260
gctggctagc gtgcaccaat gcttctggcg tcaggcagcc atcggaagct gtggtatggc    4320
tgtgcaggtc gtaaatcact gcataattcg tgtcgctcaa ggcgcactcc cgttctggat    4380 aatgttttt gcgccgacat cataacggtt ctggcaaata ttctgaaatg agctgttgac    4440
aattaatcat ccggctcgta taatgtgtgg aattgtgagc ggataacaat tcacacagg    4500 aaacagacca tgactagtaa ggaggacaat tccatggctg ctgctgctga tagattaaac    4560
ttaacttccg gccacttgaa tgctggtaga aagagaagtt cctcttctgt ttctttgaag    4620
```

```
gctgccgaaa agcctttcaa ggttactgtg attggatctg gtaactgggg tactactatt    4680
gccaaggtgg ttgccgaaaa ttgtaaggga tacccagaag ttttcgctcc aatagtacaa    4740
atgtgggtgt tcgaagaaga gatcaatggt gaaaaattga ctgaaatcat aaatactaga    4800
catcaaaacg tgaaatactt gcctggcatc actctacccg acaatttggt tgctaatcca    4860
gacttgattg attcagtcaa ggatgtcgac atcatcgttt tcaacattcc acatcaattt    4920
ttgccccgta tctgtagcca attgaaaggt catgttgatt cacacgtcag agctatctcc    4980
tgtctaaagg gttttgaagt tggtgctaaa ggtgtccaat tgctatcctc ttacatcact    5040
gaggaactag gtattcaatg tggtgctcta tctggtgcta acattgccac cgaagtcgct    5100
caagaacact ggtctgaaac aacagttgct taccacattc caaggatttt cagaggcgag    5160
ggcaaggacg tcgaccataa ggttctaaag gccttgttcc acagacctta cttccacgtt    5220
agtgtcatcg aagatgttgc tggtatctcc atctgtggtg ctttgaagaa cgttgttgcc    5280
ttaggttgtg gtttcgtcga aggtctaggc tggggtaaca acgcttctgc tgccatccaa    5340
agagtcggtt tgggtgagat catcagattc ggtcaaatgt ttttcccaga atctagagaa    5400
gaaacatact accaagagtc tgctggtgtt gctgatttga tcaccacctg cgctggtggt    5460
agaaacgtca aggttgctag gctaatggct acttctggta aggacgcctg ggaatgtgaa    5520
aaggagttgt tgaatggcca atccgctcaa ggtttaatta cctgcaaaga agttcacgaa    5580
tggttggaaa catgtggctc tgtcgaagac ttcccattat ttgaagccgt ataccaaatc    5640
gtttacaaca actacccaat gaagaacctg ccggacatga ttgaagaatt agatctacat    5700
gaagattaga tttattggat ccaggaaaca gactagaatt atgggattga ctactaaacc    5760
tctatctttg aaagttaacg ccgctttgtt cgacgtcgac ggtaccatta tcatctctca    5820
accagccatt gctgcattct ggagggattt cggtaaggac aaaccttatt tcgatgctga    5880
acacgttatc caagtctcgc atggttggag aacgtttgat gccattgcta agttcgctcc    5940
agactttgcc aatgaagagt atgttaacaa attagaagct gaaattccgg tcaagtacgg    6000
tgaaaaatcc attgaagtcc caggtgcagt taagctgtgc aacgctttga acgctctacc    6060
aaaagagaaa tgggctgtgg caacttccgg tacccgtgat atggcacaaa atggttcga    6120 gcatctggga atcaggagac caagtactt cattaccgct aatgatgtca acagggtaa    6180 gcctcatcca gaaccatatc tgaagggcag gaatggctta ggatatccga tcaatgagca    6240
agacccttcc aaatctaagg tagtagtatt tgaagacgct ccagcaggta ttgccgccgg    6300
aaaagccgcc ggttgtaaga tcattggtat tgccactact ttcgacttgg acttcctaaa    6360 ggaaaaggc tgtgacatca ttgtcaaaaa ccacgaatcc atcagagttg gcggctacaa    6420
tgccgaaaca gacgaagttg aattcatttt tgacgactac ttatatgcta aggacgatct    6480
gttgaaatgt aacccgggc tgcaggcatg caagcttggc tgttttggcg gatgagagaa    6540
gattttcagc ctgatacaga ttaaatcaga acgcagaagc ggtctgataa aacagaattt    6600
gcctggcgga gtagcgcgg tggtcccacc tgaccccatg ccgaactcag aagtgaaacg    6660
ccgtagcgcc gatggtagtg tggggtctcc ccatgcgaga gtagggaact gccaggcatc    6720
aaataaaacg aaaggctcag tcgaaagact gggcctttcg ttttatctgt tgtttgtcgg    6780
tgaacgctct cctgagtagg acaaatccgc cgggagcgga tttgaacgtt gcgaagcaac    6840 ggcccgagg gtggcgggca ggacgcccgc cataaactgc caggcatcaa attaagcaga    6900
aggccatcct gacggatggc cttttgcgt ttctacaaac tccagctgga tcgggcgcta    6960
```

-continued

| | |
|---|---|
| gcgcggccgc cccgggtacc gagctcgaat tcactggccg tcgttttaca acgtcgtgac | 7020 |
| tgggaaaacc ctggcgttac ccaacttaat cgccttgcag cacatccccc tttcgccagc | 7080 |
| tggcgtaata gcgaagaggc ccgcaccgat cgcccttccc aacagttgcg cagcctgaat | 7140 |
| ggcgaatggc gcctgatgcg gtattttctc cttacgcatc tgtgcggtat ttcacaccgc | 7200 |
| atatggtgca ctctcagtac aatctgctct gatgccgcat agttaagcca gccccgacac | 7260 |
| ccgccaacac ccgctgacga gct | 7283 |

<210> SEQ ID NO 71
<211> LENGTH: 13669
<212> TYPE: DNA
<213> ORGANISM: artificial sequence
<220> FEATURE:
<223> OTHER INFORMATION: plasmid

<400> SEQUENCE: 71

| | |
|---|---|
| tagtaaagcc ctcgctagat tttaatgcgg atgttgcgat tacttcgcca actattgcga | 60 |
| taacaagaaa aagccagcct ttcatgatat atctcccaat tgtgtagggg cttattatgc | 120 |
| acgcttaaaa ataataaaag cagacttgac ctgatagttt ggctgtgagc aattatgtgc | 180 |
| ttagtgcatc taacgcttga gttaagccgc gccgcgaagc ggcgtcggct tgaacgaatt | 240 |
| gttagacatt atttgccgac taccttggtg atctcgcctt tcacgtagtg acaaattct | 300 |
| tccaactgat ctgcgcgcga ggccaagcga tcttcttctt gtccaagata agcctgtcta | 360 |
| gcttcaagta tgacgggctg atactgggcc ggcaggcgct ccattgccca gtcggcagcg | 420 |
| acatccttcg gcgcgatttt gccggttact gcgctgtacc aaatgcggga caacgtaagc | 480 |
| actacatttc gctcatcgcc agcccagtcg ggcggcgagt tccatagcgt taaggtttca | 540 |
| tttagcgcct caaatagatc ctgttcagga accggatcaa agagttcctc cgccgctgga | 600 |
| cctaccaagg caacgctatg ttctcttgct tttgtcagca agatagccag atcaatgtcg | 660 |
| atcgtggctg gctcgaagat acctgcaaga atgtcattgc gctgccattc tccaaattgc | 720 |
| agttcgcgct tagctggata cgccacggaa tgatgtcgt cgtgcacaac aatggtgact | 780 |
| tctacagcgc ggagaatctc gctctctcca ggggaagccg aagtttccaa aaggtcgttg | 840 |
| atcaaagctc gccgcgttgt ttcatcaagc cttacggtca ccgtaaccag caaatcaata | 900 |
| tcactgtgtg gcttcaggcc gccatccact gcggagccgt acaaatgtac ggccagcaac | 960 |
| gtcggttcga gatggcgctc gatgacgcca actacctctg atagttgagt cgatacttcg | 1020 |
| gcgatcaccg cttccctcat gatgtttaac tttgttttag ggcgactgcc ctgctgcgta | 1080 |
| acatcgttgc tgctccataa catcaaacat cgacccacgg cgtaacgcgc ttgctgcttg | 1140 |
| gatgcccgag gcatagactg taccccaaaa aaacagtcat aacaagccat gaaaaccgcc | 1200 |
| actgcgccgt taccaccgct gcgttcggtc aaggttctgg accagttgcg tgagcgcata | 1260 |
| cgctacttgc attacagctt acgaaccgaa caggcttatg tccactgggt tcgtgccttc | 1320 |
| atccgtttcc acggtgtgcg tcacccggca accttgggca gcagcgaagt cgaggcattt | 1380 |
| ctgtcctggc tggcgaacga gcgcaaggtt tcggtctcca cgcatcgtca ggcattggcg | 1440 |
| gccttgctgt tcttctacgg caaggtgctg tgcacggatc tgccctggct tcaggagatc | 1500 |
| ggaagacctc ggccgtcgcg gcgcttgccg gtggtgctga cccggatga agtggttcgc | 1560 |
| atcctcggtt ttctggaagg cgagcatcgt ttgttcgccc agcttctgta tggaacgggc | 1620 |
| atgcggatca gtgagggttt gcaactgcgg gtcaaggatc tggatttcga tcacggcacg | 1680 |
| atcatcgtgc gggagggcaa gggctccaag gatcgggcct tgatgttacc cgagagcttg | 1740 |

```
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgatttttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160 ctatctttt tacaccgttt tcatctgtgc atatggacag ttttcccttt gatatgtaac     2220
ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
atttttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta atctttact tattggtttc aaaacccatt ggttaagcct tttaaactca     2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttcgct tgagaacttg     2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagaccttt    3360 gctgaaaac ttgtaaattc tgctagaccc tctgtaaatt ccgctagacc tttgtgtgtt     3420
ttttttgttt atattcaagt ggttataatt tatagaataa agaagaata aaaaagata      3480 aaagaatag atcccagccc tgtgtataac tcactacttt agtcagttcc gcagtattac     3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc     3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
```

```
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcggagaa gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga   4860 ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatacaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc   5700 tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880 ttcaccttttt gagccgatga acaatgaaaa gatcaaaacg atttgcagta ctggcccagc   5940
gccccgtcaa tcaggacggg ctgattggcg agtggcctga agaggggctg atcgccatgg   6000
acagcccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggaccccc tccaaccagt gccacgtcac caatctcaaa gataatccgg   6360
tgcagattgc cgctgacgcc gccgaggcgg gatccgcgg cttctcagaa caggagacca   6420
cggtcggtat cgcgcgctac gcgccgtttaa acgccctggc gctgttggtc ggttcgcagt   6480
```

```
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttct  ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct tgaggatat  cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620 tgaaacccg  cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc    7800 gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220 cccgagcat  atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgccgtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgccttg  tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag    8700 cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
```

```
tcttaacgaa gccgcgccgg tgattggcga tgtggcgatg gagaccatca ccgagaccat  8880
tatcaccgaa tcgaccatga tcggtcataa cccgcagacg ccgggcgggg tgggcgttgg  8940
cgtggggacg actatcgccc tcgggcggct ggcgacgctg ccggcggcgc agtatgccga  9000
ggggtggatc gtactgattg acgacgccgt cgatttcctt gacgccgtgt ggtggctcaa  9060
tgaggcgctc gaccggggga tcaacgtggt ggcggcgatc ctcaaaaagg acgacggcgt  9120
gctggtgaac aaccgcctgc gtaaaaccct gccggtggtg gatgaagtga cgctgctgga  9180
gcaggtcccc gagggggtaa tggcggcggt ggaagtggcc gcgccgggcc aggtggtgcg  9240
gatcctgtcg aatccctacg ggatcgccac cttcttcggg ctaagcccgg aagagaccca  9300
ggccatcgtc cccatcgccc gcgccctgat tggcaaccgt tccgcggtgg tgctcaagac  9360
cccgcagggg gatgtgcagt cgcggtgat cccggcgggc aacctctaca ttagcggcga  9420
aaagcgccgc ggagaggccg atgtcgccga gggcgcggaa gccatcatgc aggcgatgag  9480
cgcctgcgct ccggtacgcg catccgcgg cgaaccgggc acccacgccg gcggcatgct  9540
tgagcgggtg cgcaaggtaa tggcgtccct gaccggccat gagatgagcg cgatatacat  9600
ccaggatctg ctggcggtgg atacgtttat tccgcgcaag gtgcagggcg ggatggccgg  9660
cgagtgcgcc atggagaatg ccgtcgggat ggcggcgatg gtgaaagcgg atcgtctgca  9720
aatgcaggtt atcgcccgcg aactgagcgc ccgactgcag accgaggtgg tggtgggcgg  9780
cgtggaggcc aacatggcca tcgccggggc gttaaccact cccggctgtg cggcgccgct  9840
ggcgatcctc gacctcggcg ccggctcgac ggatgcggcg atcgtcaacg cggaggggca  9900
gataacggcg gtccatctcg ccggggcggg gaatatggtc agcctgttga ttaaaaccga  9960
gctgggcctc gaggatcttt cgctggcgga agcgataaaa aaatacccgc tggccaaagt 10020
ggaaagcctg ttcagtattc gtcacgagaa tggcgcggtg gagttctttc gggaagccct 10080
cagcccggcg gtgttcgcca aagtggtgta catcaaggag ggcgaactgg tgccgatcga 10140
taacgccagc ccgctggaaa aaattcgtct cgtgcgccgg caggcgaaag agaaagtgtt 10200
tgtcaccaac tgcctgcgcg cgctgcgcca ggtctcaccc ggcggttcca ttcgcgatat 10260
cgcctttgtg gtgctggtgg gcggctcatc gctggacttt gagatcccgc agcttatcac 10320
ggaagccttg tcgcactatg gcgtggtcgc cgggcagggc aatattcggg aacagaagg 10380
gccgcgcaat gcggtcgcca ccgggctgct actggccggt caggcgaatt aaacgggcgc 10440
tcgcgccagc ctctaggtac aaataaaaaa ggcacgtcag atgacgtgcc ttttttcttg 10500
tctagagtac tggcgaaagg gggatgtgct gcaaggcgat taagttgggt aacgccaggg 10560
ttttcccagt cacgacgttg taaaacgacg gccagtgaat tcgagctcgg tacccggggc 10620
ggccgcgcta gcgcccgatc cagctggagt ttgtagaaac gcaaaaggc catccgtcag 10680
gatggccttc tgcttaattt gatgcctggc agtttatggc gggcgtcctg cccgccaccc 10740
tccgggccgt gcttcgcaa cgttcaaatc cgctcccggc ggatttgtcc tactcaggag 10800
agcgttcacc gacaaacaac agataaaacg aaaggcccag tctttcgact gagcctttcg 10860
ttttatttga tgcctggcag ttccctactc tcgcatgggg agaccccaca ctaccatcgg 10920
cgctacggcg tttcacttct gagttcggca tggggtcagg tgggaccacc gcgctactgc 10980
cgccaggcaa attctgtttt atcagaccgc ttctgcgttc tgatttaatc tgtatcaggc 11040
tgaaaatctt ctctcatccg ccaaaacagc caagcttgca tgcctgcagc ccgggttacc 11100
atttcaacag atcgtcctta gcatataagt agtcgtcaaa aatgaattca acttcgtctg 11160
tttcggcatt gtagccgcca actctgatgg attcgtggtt tttgacaatg atgtcacagc 11220
```

-continued

```
cttttteectt taggaagtcc aagtcgaaag tagtggcaat accaatgatc ttacaaccgg   11280
cggcttttcc ggcggcaata cctgctggag cgtcttcaaa tactactacc ttagatttgg   11340
aagggtcttg ctcattgatc ggatatccta agccattcct gcccttcaga tatggttctg   11400
gatgaggctt accctgtttg acatcattag cggtaatgaa gtactttggt ctcctgattc   11460
ccagatgctc gaaccatttt tgtgccatat cacgggtacc ggaagttgcc acagcccatt   11520
tctcttttgg tagagcgttc aaagcgttgc acagcttaac tgcacctggg acttcaatgg   11580 attttteacc gtacttgacc ggaatttcag cttctaattt gttaacatac tcttcattgg   11640
caaagtctgg agcgaactta gcaatggcat caaacgttct ccaaccatgc gagacttgga   11700
taacgtgttc agcatcgaaa taaggtttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttctagtctg tttcctggat ccaataaatc   11880
taatcttcat gtagatctaa ttcttcaatc atgtccggca ggttcttcat tgggtagttg   11940
ttgtaaacga tttggtatac ggcttcaaat aatgggaagt cttcgacaga gcccacatgtt  12000 tccaaccatt cgtgaacttc tttgcaggta attaaacctt gagcggattg gccattcaac   12060
aactcctttt cacattccca ggcgtcctta ccagaagtag ccattagcct agcaaccttg   12120
acgtttctac caccagcgca ggtggtgatc aaatcagcaa caccagcaga ctcttggtag   12180
tatgtttctt ctctagattc tgggaaaaac atttgaccga atctgatgat ctcacccaaa   12240
ccgactcttt ggatggcagc agaagcgttg ttaccccagc ctagaccttc gacgaaacca   12300
caacctaagg caacaacgtt cttcaaagca ccacagatgg agataccagc aacatcttcg   12360
atgacactaa cgtggaagta aggtctgtgg aacaaggcct ttagaacctt atggtcgacg   12420
tccttgccct cgcctctgaa atcctttgga atgtggtaag caactgttgt ttcagaccag   12480
tgttcttgag cgacttcggt ggcaatgtta gcaccagata gagcaccaca ttgaatacct   12540
agttcctcag tgatgtaaga ggatagcaat tggacacctt tagcaccaac ttcaaaaccc   12600
tttagacagg agatagctct gacgtgtgaa tcaacatgac ctttcaattg gctacagata   12660
cggggcaaaa attgatgtgg aatgttgaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttttcac cattgatctc ttcttcgaac   12840
acccacattt gtactattgg agcgaaaact tctgggtatc ccttacaatt ttcggcaacc   12900
accttggcaa tagtagtacc ccagttacca gatccaatca cagtaacctt gaaaggcttt   12960
tcggcagcct tcaaagaaac agaagaggaa cttctctttc taccagcatt caagtggccg   13020
gaagttaagt ttaatctatc agcagcagca gccatggaat tgtcctcctt actagtcatg   13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
aaaacattat ccagaacggg agtgcgcctt gagcgcacacg aattatgcag tgatttacga   13260
cctgcacagc cataccacag cttccgatgg ctgcctgacg ccagaagcat tggtgcacgc   13320
tagccagtac atttaaatgg taccctctag tcaaggcctt aagtgagtcg tattacggac   13380
tggccgtcgt tttacaacgt cgtgactggg aaaaccctgg cgttacccaa cttaatcgcc   13440
ttgcagcaca tccccctttc gccagctggc gtaatagcga gaggcccgc accgatcgcc   13500 cttcccaaca gttgcgcagc ctgaatggcg aatggcgcct gatgcggtat tttctcctta   13560
```

-continued

```
cgcatctgtg cggtatttca caccgcatat ggtgcactct cagtacaatc tgctctgatg    13620
ccgcatagtt aagccagccc cgacacccgc caacacccgc tgacgagct                13669

<210> SEQ ID NO 72
<211> LENGTH: 13543
<212> TYPE: DNA
<213> ORGANISM: artificial sequence
<220> FEATURE:
<223> OTHER INFORMATION: plasmid

<400> SEQUENCE: 72
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct     300 tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480 actcatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta    1980
```

```
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160 ctatctttt tacaccgttt tcatctgtgc atatggacag ttttcccttt gatatgtaac     2220
ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact     2580
tggaaaatca acgtatcagt cgggcggcct cgcttatcaa ccaccaattt catattgctg    2640
taagtgttta atctttact tattggtttc aaaacccatt ggttaagcct tttaaactca     2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtccttt cctttgagtt gtgggtatct gtaaattctg ctagacctt     3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata     3480 aaagaaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttttcgtga cattcagttc gctgcgctca cggctctggc   3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc     3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga ctatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
```

```
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga    4860 ccataaccta tgacggaggc ggtgacgccg ctgcgctggg cgccctggcg ccagaagct    4920 cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatacaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc tttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga ctatgccaca   5820
tcctgagcaa ataattcaac cactaaacaa atcaaccgcg tttcccggag gtaaccaagc   5880 ttcaccttt gagccgatga acaatgaaaa gatcaaaacg atttgcagta ctggcccagc    5940
gccccgtcaa tcaggacggg ctgattggcg agtggcctga agaggggctg atcgccatgg   6000 acagccccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggaccccc tccaaccagt gccacgtcac caatctcaaa gataatccgg   6360
tgcagattgc cgctgacgcc gccgaggccg gatccgcgg cttctcagaa caggagacca    6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
```

```
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttct ccggctacag cgcggtgccg aactacgaca     7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct tgaggatat cgccagcaat attctcaata     7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620 tgaaacccg cgagggcggg gtagcttctg ccgatgaacg cgccgatgaa gtggtgatcg     7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc      7800 gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220 cccgagcat atcctgacgc ctaccggcaa accattgacc gatattaccc tcgagaaggt     8280
gctctctggc gaggtgggcc cgcaggatgt gcggatctcc cgccagaccc ttgagtacca    8340
ggcgcagatt gccgagcaga tgcagcgcca tgccgtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag     8700 cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
```

-continued

```
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gaggggtaa tggcggcggt ggaagtggcc gcgccgggcc aggtggtgcg     9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg catccgcgg cgaaccgggc acccacgccg gcggcatgct     9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accaggtgg tggtgggcgg     9780 cgtggaggcc aacatggcca tcgccgggc gttaaccact cccggctgtg cggcgccgct     9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg gaacagaagg   10380
gccgcgcaat gcggtcgcca ccgggctgct actggccggt caggcgaatt aaacgggcgc   10440
tcgcgccagc ctctaggtac aaataaaaaa ggcacgtcag atgacgtgcc tttttttctg   10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620 tttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctgggtact actattgcca   10920 aggtggttgc cgaaaattgt aagggatacc agaagttttt cgctccaata gtacaaatgt   10980
gggtgttcga agaagagatc aatggtgaaa aattgactga atcataaat actagacatc   11040 aaaacgtgaa atacttgcct ggcatcactc tacccgacaa tttggttgct aatccagact   11100
tgattgattc agtcaaggat gtcgacatca tcgtttttcaa cattccacat caattttgc    11160 cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
```

```
tcatcgaaga tgttgctggt atctccatct gtggtgcttt gaagaacgtt gttgccttag    11520
gttgtggttt cgtcgaaggt ctaggctggg gtaacaacgc ttctgctgcc atccaaagag    11580
tcggtttggg tgagatcatc agattcggtc aaatgttttt cccagaatct agagaagaaa    11640
catactacca agagtctgct ggtgttgctg atttgatcac cacctgcgct ggtggtagaa    11700
acgtcaaggt tgctaggcta atggctactt ctggtaagga cgcctgggaa tgtgaaaagg    11760
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttgac gactacttat atgctaagga cgatctgttg    12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
aaaacgaaag gctcagtcga aagactgggc ctttcgtttt atctgttgtt tgtcggtgaa    13020
cgctctcctg agtaggacaa atccgccggg agcggatttg aacgttgcga gcaacggcc    13080 cggagggtgg cgggcaggac gcccgccata aactgccagg catcaaatta gcagaaggc    13140 catcctgacg gatggccttt ttgcgtttct acaaactcca gctggatcgg cgctagagt    13200 atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                      13543
```

<210> SEQ ID NO 73
<211> LENGTH: 13543
<212> TYPE: DNA
<213> ORGANISM: artificial sequence
<220> FEATURE:
<223> OTHER INFORMATION: plasmid

```
<400> SEQUENCE: 73
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
ttagtgcatc taacgcttga gttaagccgc gccgcgaagc ggcgtcggct tgaacgaatt   240
gttagacatt atttgccgac taccttggtg atctcgcctt tcacgtagtg dacaaattct   300
tccaactgat ctgcgcgcga ggccaagcga tcttcttctt gtccaagata agcctgtcta   360
gcttcaagta tgacgggctg atactgggcc ggcaggcgct ccattgccca gtcggcagcg   420
acatccttcg gcgcgatttt gccggttact gcgctgtacc aaatgcggga caacgtaagc   480
actacatttc gctcatcgcc agcccagtcg ggcggcgagt tccatagcgt taaggtttca   540
tttagcgcct caaatagatc ctgttcagga accggatcaa agagttcctc cgccgctgga   600
cctaccaagg caacgctatg ttctcttgct tttgtcagca agatagccag atcaatgtcg   660
atcgtggctg gctcgaagat acctgcaaga atgtcattgc gctgccattc tccaaattgc   720
agttcgcgct tagctggata acgccacgga atgatgtcgt cgtgcacaac aatggtgact   780
tctacagcgc ggagaatctc gctctctcca ggggaagccg aagtttccaa aaggtcgttg   840
atcaaagctc gccgcgttgt ttcatcaagc cttacggtca ccgtaaccag caatcaata   900
tcactgtgtg gcttcaggcc gccatccact gcggagccgt acaaatgtac ggccagcaac   960
gtcggttcga gatggcgctc gatgacgcca actacctctg atagttgagt cgatacttcg  1020
gcgatcaccg cttccctcat gatgtttaac tttgttttag ggcgactgcc ctgctgcgta  1080
acatcgttgc tgctccataa catcaaacat cgacccacgg cgtaacgcgc ttgctgcttg  1140
gatgcccgag gcatagactg taccccaaaa aaacagtcat aacaagccat gaaaaccgcc  1200
actgcgccgt taccaccgct gcgttcggtc aaggttctgg accagttgcg tgagcgcata  1260
cgctacttgc attacagctt acgaaccgaa caggcttatg tccactgggt tcgtgccttc  1320
atccgtttcc acggtgtgcg tcacccggca accttgggca gcagcgaagt cgaggcattt  1380
ctgtcctggc tggcgaacga gcgcaaggtt tcggtctcca cgcatcgtca ggcattggcg  1440
gccttgctgt tcttctacgg caaggtgctg tgcacggatc tgccctggct tcaggagatc  1500
ggaagacctc ggccgtcgcg gcgcttgccg gtggtgctga ccccggatga agtggttcgc  1560
atcctcggtt ttctggaagg cgagcatcgt ttgttcgccc agcttctgta tggaacgggc  1620
atgcggatca gtgagggttt gcaactgcgg gtcaaggatc tggatttcga tcacggcacg  1680
atcatcgtgc gggagggcaa gggctccaag gatcgggcct tgatgttacc cgagagcttg  1740
gcacccagcc tgcgcgagca ggggaattaa ttcccacggg ttttgctgcc cgcaaacggg  1800
ctgttctggt gttgctagtt tgttatcaga atcgcagatc cggcttcagc cggtttgccg  1860
gctgaaagcg ctatttcttc cagaattgcc atgattttt ccccacggga ggcgtcactg  1920
gctcccgtgt tgtcggcagc tttgattcga taagcagcat cgcctgtttc aggctgtcta  1980
tgtgtgactt tgagctgta acaagttgtc tcaggtgttc aatttcatgt tctagttgct  2040
ttgtttact ggtttcacct gttctattag gtgttacatg ctgttcatct gttacattgt  2100
cgatctgttc atggtgaaca gctttgaatg caccaaaaac tcgtaaaagc tctgatgtat  2160
ctatcttttt tacaccgttt tcatctgtgc atatggacag ttttcccttt gatatgtaac  2220
ggtgaacagt tgttctactt tgtttgtta gtccttgatgc ttcactgata gatacaagag  2280
ccataagaac ctcagatcct tccgtattta gccagtatgt tctctagtgt ggttcgttgt  2340
```

```
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct  ggttgttctc aagttcggtt acgagatcca tttgtctatc tagttcaact    2580
tggaaaatca acgtatcagt cgggcggcct cgcttatcaa ccaccaattt catattgctg    2640
taagtgttta atctttact  tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt tccctactg    3060 atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtccttt  cctttgagtt gtgggtatct gtaaattctg ctagacccttt   3360 gctggaaaac ttgtaaattc tgctagaccc tctgtaaatt ccgctagacc tttgtgtgtt    3420 tttttgttt  atattcaagt ggttataatt tatagaataa agaaagaata aaaaagata     3480 aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga  cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg  ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttaatga  gcaggtaatt ggcgccgtcg gcgttagcgg cggtacggtc    4620
gagcaggatc aattattagc ccagtgcgcc ctggattgtt tttccgcatt ataacctgaa    4680
```

```
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga     4860
ccataaccta tgacggaggc ggtgacgccg ctgcgctggg cgccctggcg gccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc cgttaaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc     5700
tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatggcg ctgcagaaga    6300
tgcgtgcccg ccggaccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttct ccggctacag cgcggtgccg aactacgaca    7020
acatgttcgc cggctcgaac ttcgatgcgg aagattttga tgattacaac atcctgcagc    7080
```

```
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct tgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaatattcc gggcgtggtt cagcccgaca    7560
ccattgaata aggcggtatt cctgtgcaac agacaaccca aattcagccc tcttttaccc    7620 tgaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctcccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220 cccgagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag    8700 cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gaggggtaa tggcggcggt ggaagtggcc gcgccgggcc aggtggtgcg    9240
gatcctgtcg aatccctacg ggatcgcac cttcttcggg ctaagccgg aagagaccca    9300 ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
```

```
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg gaacagaagg   10380
gccgcgcaat gcggtcgcca ccgggctgct actggccggt caggcgaatt aaacgggcgc   10440
tcgcgccagc ctctaggtac aaataaaaaa ggcacgtcag atgacgtgcc tttttcttg    10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620
tttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc cagaagtttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
tgattgattc agtcaaggat gtcgacatca tcgttttcaa cattccacat caattttttgc   11160
cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt taattacctg caaagaagtt cacgaatggt   11820
```

```
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttttgac gactacttat atgctaagga cgatctgttg    12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
aaaacgaaag gctcagtcga aagactgggc ctttcgtttt atctgttgtt tgtcggtgaa    13020
cgctctcctg agtaggacaa atccgccggg agcggatttg aacgttgcga agcaacggcc    13080
cggagggtgg cgggcaggac gcccgccata aactgccagg catcaaatta agcagaaggc    13140
catcctgacg gatggccttt ttgcgtttct acaaactcca gctggatcgg cgctagagt    13200 atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                      13543
```

<210> SEQ ID NO 74
<211> LENGTH: 13402
<212> TYPE: DNA
<213> ORGANISM: artificial sequence
<220> FEATURE:
<223> OTHER INFORMATION: plasmid

<400> SEQUENCE: 74

```
tagtaaagcc ctcgctagat tttaatgcgg atgttgcgat tacttcgcca actattgcga    60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
```

-continued

```
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata cgccacggaa tgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caatcaata    900 tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320 atccgttttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040 ttgtttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttccctttt gatatgtaac   2220 ggtgaacagt tgttctactt tgttttgtta gtcttgatgc ttcactgata gatacaagag   2280
ccataagaac ctcagatcct tccgtattta gccagtatgt tctctagtgt ggttcgttgt   2340 tttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact   2580
tggaaaatca acgtatcagt cgggcggcct cgcttatcaa ccaccaattt catattgctg   2640 taagtgtta aatctttact tattggtttc aaaacccatt ggttaagcct tttaaactca   2700
```

```
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagaccttt    3360
gctggaaaac ttgtaaattc tgctagaccc tctgtaaatt ccgctagacc tttgtgtgtt    3420
ttttttgttt atattcaagt ggttataatt tatagaataa agaaagaata aaaaagata    3480
aaagaatag atcccagccc tgtgtataac tcactacttt agtcagttcc gcagtattac    3540
aaaaggatgt cgcaaacgct gttttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg cctttatgg attcatgcaa ggaaactacc    3780
cataatacaa gaaaagcccg tcacgggctt ctcagggcgt tttatggcgg gtctgctatg    3840
tggtgctatc tgactttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860
ccataacccta tgacggaggc ggtgacgccg ctgcgctggg cgccctggcg gccagaagct    4920
cgccctgcg ggtgggtatc gggctcagcc cgtccggcga gatagccctc actcatgccc    4980
agctgccggc ggacgcgccg ctggctaccg gacacgtcac cgatagcgac gatcaactgc    5040
```

```
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagt aatctcgcct   5460
ctgcccagct gcaccctgat gcttgcgctt gaactggcct agcaaacaca gaaaaaagcc   5520
cgcacctgac agtgcgggct tttttttcc taggcgatct gtgctgtttg ccacggtatg    5580
cagcaccagc gcgagattat gggctcgcac gctcgactgt cggacggggg cactggaacg   5640
agaagtcagg cgagccgtca cgcccttgac aatgccacat cctgagcaaa taattcaacc   5700
actaaacaaa tcaaccgcgt ttcccggagg taaccaagct tcaccttttg agccgatgaa   5760
caatgaaaag atcaaaacga tttgcagtac tggcccagcg ccccgtcaat caggacgggc   5820
tgattggcga gtggcctgaa gaggggctga tcgccatgga cagccccttt gacccggtct   5880
cttcagtaaa agtggacaac ggtctgatcg tcgaactgga cggcaaacgc cgggaccagt   5940
ttgacatgat cgaccgattt atcgccgatt acgcgatcaa cgttgagcgc acagagcagg   6000
caatgcgcct ggaggcggtg gaaatagccc gtatgctggt ggatattcac gtcagccggg   6060
aggagatcat tgccatcact accgccatca cgccggccaa agcggtcgag gtgatggcgc   6120
agatgaacgt ggtggagatg atgatggcgc tgcagaagat gcgtgcccgc cggaccccct   6180
ccaaccagtg ccacgtcacc aatctcaaag ataatccggt gcagattgcc gctgacgccg   6240
ccgaggccgg gatccgcggc ttctcagaac aggagaccac ggtcggtatc gcgcgctacg   6300
cgccgtttaa cgccctggcg ctgttggtcg gttcgcagtg cggccgcccc ggcgtgttga   6360
cgcagtgctc ggtggaagag gccaccgagc tggagctggg catgcgtggc ttaaccagct   6420
acgccgagac ggtgtcggtc tacgcaccg aagcggtatt taccgacggc gatgatacgc    6480
cgtggtcaaa ggcgttcctc gcctcggcct acgcctcccg cgggttgaaa atgcgctaca   6540
cctccggcac cggatccgaa cgctgatgg gctattcgga gagcaagtcg atgctctacc    6600
tcgaatcgcg ctgcatcttc attactaaag gcgccggggt tcagggactg caaaacggcg   6660
cggtgagctg tatcggcatg accggcgctg tgccgtcggg cattcgggcg gtgctggcgg   6720
aaaacctgat cgcctctatg ctcgacctcg aagtggcgtc cgccaacgac cagactttct   6780
cccactcgga tattgccgc accgcgcgca cctgatgca gatgctgccg gcaccgact    6840 ttattttctc cggctacagc gcggtgccga actacgacaa catgttcgcc ggctcgaact   6900
tcgatgcgga agattttgat gattacaaca tcctgcagcg tgacctgatg gttgacggcg   6960
gcctgcgtcc ggtgaccgag gcggaaacca ttgccattcg ccagaaagcg cgcgggcga    7020 tccaggcggt tttccgcgag ctggggctgc cgccaatcgc cgacgaggag gtggaggccg   7080
ccacctacgc gcacggcagc aacgagatgc gccgcgtaa cgtggtggag atctgagtg    7140 cggtggaaga gatgatgaag cgcaacatca ccggcctcga tattgtcggc gcgctgagcc   7200
gcagcggctt tgaggatatc gccagcaata ttctcaatat gctgcgccag cgggtcaccg   7260
gcgattacct gcagacctcg gccattctcg atcggcagtt cgaggtggtg agtgcggtca   7320
acgacatcaa tgactatcag gggccgggca ccggctatcg catctctgcc gaacgctggg   7380
cggagatcaa aaatattccg ggcgtggttc agcccgacac cattgaataa ggcggtattc   7440
```

```
ctgtgcaaca gacaacccaa attcagccct cttttaccct gaaaaccegc gagggcgggg     7500
tagcttctgc cgatgaacgc gccgatgaag tggtgatcgg cgtcggccct gccttcgata     7560
aacaccagca tcacactctg atcgatatgc cccatggcgc gatcctcaaa gagctgattg     7620
ccggggtgga agaagagggg cttcacgccc gggtggtgcg cattctgcgc acgtccgacg     7680
tctcctttat ggcctgggat gcggccaacc tgagcggctc ggggatcggc atcggtatcc     7740
agtcgaaggg gaccacggtc atccatcagc gcgatctgct gccgctcagc aacctggagc     7800
tgttctccca ggcgccgctg ctgacgctgg agacctaccg gcagattggc aaaaacgctg     7860
cgcgctatgc gcgcaaagag tcaccttcgc cggtgccggt ggtgaacgat cagatggtgc     7920
ggccgaaatt tatggccaaa gccgcgctat ttcatatcaa agagaccaaa catgtggtgc     7980
aggacgccga gcccgtcacc ctgcacatcg acttagtaag ggagtgacca tgagcgagaa     8040
aaccatgcgc gtgcaggatt atccgttagc cacccgctgc ccggagcata tcctgacgcc     8100
taccggcaaa ccattgaccg atattaccct cgagaaggtg ctctctggcg aggtgggccc     8160
gcaggatgtg cggatctccc gccagaccct tgagtaccag gcgcagattg ccagcagat     8220
gcagcgccat gcggtggcgc gcaatttccg ccgcgcggcg gagcttatcg ccattcctga     8280
cgagcgcatt ctggctatct ataacgcgct gcgcccgttc cgctcctcgc aggcggagct     8340
gctggcgatc gccgacgagc tggagcacac ctggcatgcg acagtgaatg ccgcctttgt     8400
ccgggagtcg gcggaagtgt atcagcagcg gcataagctg cgtaaaggaa gctaagcgga     8460
ggtcagcatg ccgttaatag ccgggattga tatcggcaac gccaccaccg aggtggcgct     8520
ggcgtccgac tacccgcagg cgagggcgtt tgttgccagc gggatcgtcg cgacgacggg     8580
catgaaaggg acgcgggaca atatcgccgg gaccctcgcc gcgctggagc aggccctggc     8640
gaaaacaccg tggtcgatga gcgatgtctc tcgcatctat cttaacgaag ccgcgccggt     8700
gattggcgat gtggcgatgg agaccatcac cgagaccatt atcaccgaat cgaccatgat     8760
cggtcataac ccgcagacgc cggcgggggt gggcgttggc gtggggacga ctatcgccct     8820
cgggcggctg gcgacgctgc cggcggcgca gtatgccgag gggtggatcg tactgattga     8880
cgacgccgtc gatttccttg acgccgtgtg gtggctcaat gaggcgctcg accgggggat     8940
caacgtggtg gcggcgatcc tcaaaaagga cgacggcgtg ctggtgaaca accgcctgcg     9000
taaaaccctg ccggtggtgg atgaagtgac gctgctggag caggtccccg aggggtaat     9060
ggcggcggtg gaagtggccg cgccgggcca ggtggtgcgg atcctgtcga atccctacgg     9120
gatcgccacc ttcttcgggc taagcccgga agagacccag gccatcgtcc ccatcgcccg     9180
cgccctgatt ggcaaccgtt ccgcggtggt gctcaagacc ccgcaggggg atgtgcagtc     9240
gcgggtgatc ccggcgggca acctctacat tagcggcgaa aagcgccgcg gagaggccga     9300
tgtcgccgag ggcgcggaag ccatcatgca ggcgatgagc cctgcgctc cggtacgcga     9360
catccgcggc gaaccgggca cccacgccgg cggcatgctt gagcgggtgc gcaaggtaat     9420
ggcgtccctg accggccatg agatgagcgc gatatacatc caggatctgc tggcggtgga     9480
tacgttatt ccgcgcaagg tgcagggcgg gatggccggc gagtgcgcca tggagaatgc     9540
cgtcgggatg gcggcgatgg tgaaagcgga tcgtctgcaa atgcaggtta tcgcccgcga     9600
actgagcgcc cgactgcaga ccgaggtggt ggtgggcggc gtggaggcca acatggccat     9660
cgccgggggc ttaaccactc ccggctgtgc ggcgccgctg gcgatcctcg acctcggcgc     9720
cggctcgacg gatgcggcga tcgtcaacgc ggaggggcag ataacggcgg tccatctcgc     9780
```

```
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
agtggtgtac atcaaggagg gcgaactggt gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctggccggtc aggcgaatta acgggcgct cgcgccagcc tctaggtaca  10320
aataaaaaag gcacgtcaga tgacgtgcct tttttcttgt ctagcgtgca ccaatgcttc  10380
tggcgtcagg cagccatcgg aagctgtggt atggctgtgc aggtcgtaaa tcactgcata  10440
attcgtgtcg ctcaaggcgc actcccgttc tggataatgt tttttgcgcc gacatcataa  10500
cggttctggc aaatattctg aaatgagctg ttgacaatta atcatccggc tcgtataatg  10560
tgtggaattg tgagcggata acaatttcac acaggaaaca gaccatgact agtaaggagg  10620
acaattccat ggctgctgct gctgatagat aaaacttaac ttccggccac ttgaatgctg  10680
gtagaaagag aagttcctct tctgtttctt tgaaggctgc cgaaaagcct ttcaaggtta  10740
ctgtgattgg atctggtaac tggggtacta ctattgccaa ggtggttgcc gaaaattgta  10800
agggataccc agaagttttc gctccaatag tacaaatgtg ggtgttcgaa gaagagatca  10860
atggtgaaaa attgactgaa atcataaata ctagacatca aaacgtgaaa tacttgcctg  10920
gcatcactct acccgacaat ttggttgcta atccagactt gattgattca gtcaaggatg  10980
tcgacatcat cgttttcaac attccacatc aattttttgcc ccgtatctgt agccaattga  11040
aaggtcatgt tgattcacac gtcagagcta tctcctgtct aaagggtttt gaagttggtg  11100
ctaaaggtgt ccaattgcta tcctcttaca tcactgagga actaggtatt caatgtggtg  11160
ctctatctgg tgctaacatt gccaccgaag tcgctcaaga acactggtct gaaacaacag  11220
ttgcttacca cattccaaag gatttcagag gcgagggcaa ggacgtcgac cataaggttc  11280
taaaggcctt gttccacaga ccttacttcc acgttagtgt catcgaagat gttgctggta  11340
tctccatctg tggtgctttg aagaacgttg ttgccttagg ttgtggtttc gtcgaaggtc  11400
taggctgggg taacaacgct tctgctgcca tccaaagagt cggtttgggt gagatcatca  11460
gattcggtca aatgttttc ccagaatcta gagaagaaac atactaccaa gagtctgctg  11520
gtgttgctga tttgatcacc acctgcgctg tggtagaaaa cgtcaaggtt gctaggctaa  11580
tggctacttc tggtaaggac gcctgggaat gtgaaaagga gttgttgaat ggccaatccg  11640
ctcaaggttt aattacctgc aaagaagttc acgaatggtt ggaaacatgt ggctctgtcg  11700
aagacttccc attatttgaa gccgtatacc aaatcgttta caacaactac ccaatgaaga  11760
acctgccgga catgattgaa gaattagatc tacatgaaga ttagatttat tggatccagg  11820
aaacagacta gaattatggg attgactact aaacctctat ctttgaaagt taacgccgct  11880
ttgttcgacg tcgacggtac cattatcatc tctcaaccag ccattgctgc attctggagg  11940
gatttcggta aggacaaacc ttatttcgat gctgaacacg ttatccaagt ctcgcatggt  12000
tggagaacgt tgatgccat tgctaagttc gctccagact tgccaatga agagtatgtt  12060
aacaaattag aagctgaaat tccggtcaag tacggtgaaa aatccattga agtcccaggt  12120
gcagttaagc tgtgcaacgc tttgaacgct ctaccaaaag agaaatgggc tgtggcaact  12180
```

```
tccggtaccc gtgatatggc acaaaaatgg ttcgagcatc tgggaatcag gagaccaaag    12240
tacttcatta ccgctaatga tgtcaaacag ggtaagcctc atccagaacc atatctgaag    12300
ggcaggaatg gcttaggata tccgatcaat gagcaagacc cttccaaatc taaggtagta    12360
gtatttgaag acgctccagc aggtattgcc gccggaaaag ccgccggttg taagatcatt    12420
ggtattgcca ctactttcga cttggacttc ctaaaggaaa aaggctgtga catcattgtc    12480
aaaaaccacg aatccatcag agttggcggc tacaatgccg aaacagacga agttgaattc    12540 attttttgacg actacttata tgctaaggac gatctgttga aatggtaacc cgggctgcag    12600
gcatgcaagc ttggctgttt tggcggatga gagaagattt tcagcctgat acagattaaa    12660
tcagaacgca gaagcggtct gataaaacag aatttgcctg gcggcagtag cgcggtggtc    12720
ccacctgacc ccatgccgaa ctcagaagtg aaacgccgta gcgccgatgg tagtgtgggg    12780
tctccccatg cgagagtagg gaactgccag gcatcaaata aaacgaaagg ctcagtcgaa    12840
agactgggcc tttcgtttta tctgttgttt gtcggtgaac gctctcctga gtaggacaaa    12900
tccgccggga gcggatttga acgttgcgaa gcaacggccc ggagggtggc gggcaggacg    12960
cccgccataa actgccaggc atcaaattaa gcagaaggcc atcctgacgg atggcctttt    13020
tgcgtttcta caaactccag ctggatcggg cgctagagta tacatttaaa tggtaccctc    13080
tagtcaaggc cttaagtgag tcgtattacg gactggccgt cgttttacaa cgtcgtgact    13140
gggaaaaccc tggcgttacc caacttaatc gccttgcagc acatccccct ttcgccagct    13200
ggcgtaatag cgaagaggcc cgcaccgatc gcccttccca acagttgcgc agcctgaatg    13260
gcgaatggcg cctgatgcgg tattttctcc ttacgcatct gtgcggtatt tcacaccgca    13320
tatggtgcac tctcagtaca atctgctctg atgccgcata gttaagccag ccccgacacc    13380
cgccaacacc cgctgacgag ct                                             13402
```

<210> SEQ ID NO 75
<211> LENGTH: 110
<212> TYPE: DNA
<213> ORGANISM: artificial sequence
<220> FEATURE:
<223> OTHER INFORMATION: primer

<400> SEQUENCE: 75

```
gcagtacaaa tgttacgggg taccggcgcg ccgctagctt aattaacgga ccgatgcatg     60
agctcacgcg taccggtgct cttcgatcta cgtaagaagg ccttcctatc                110
```

<210> SEQ ID NO 76
<211> LENGTH: 110
<212> TYPE: DNA
<213> ORGANISM: artificial sequence
<220> FEATURE:
<223> OTHER INFORMATION: primer

<400> SEQUENCE: 76

```
gataggaagg ccttcttacg tagatcgaag agcaccggta cgcgtgagct catgcatcgg     60
tccgttaatt aagctagcgg cgcgccggta ccccgtaaca tttgtactgc                110
```

<210> SEQ ID NO 77
<211> LENGTH: 77
<212> TYPE: DNA
<213> ORGANISM: artificial sequence
<220> FEATURE:
<223> OTHER INFORMATION: fragment

```
<400> SEQUENCE: 77
cggcgcgccg ctagcttaat taacggaccg atgcatgagc tcacgcgtac cggtgctctt    60
cgatctacgt aagaagg                                                    77

<210> SEQ ID NO 78
<211> LENGTH: 13611
<212> TYPE: DNA
<213> ORGANISM: artificial sequence
<220> FEATURE:
<223> OTHER INFORMATION: plasmid

<400> SEQUENCE: 78
aagtgagtcg tattacggac tggccgtcgt tttacaacgt cgtgactggg aaaaccctgg    60
cgttacccaa cttaatcgcc ttgcagcaca tccccctttc gccagctggc gtaatagcga   120
agaggcccgc accgatcgcc cttcccaaca gttgcgcagc ctgaatggcg aatggcgcct   180
gatgcggtat tttctcctta cgcatctgtg cggtatttca caccgcatat ggtgcactct   240
cagtacaatc tgctctgatg ccgcatagtt aagccagccc cgacacccgc caacacccgc   300
tgacgagctt agtaaagccc tcgctagatt ttaatgcgga tgttgcgatt acttcgccaa   360
ctattgcgat aacaagaaaa agccagcctt tcatgatata tctcccaatt tgtgtagggc   420
ttattatgca cgcttaaaaa taataaaagc agacttgacc tgatagtttg gctgtgagca   480
attatgtgct tagtgcatct aacgcttgag ttaagccgcg ccgcgaagcg cgtcggctt    540 gaacgaattg ttagacatta tttgccgact accttggtga tctcgccttt cacgtagtgg   600
acaaattctt ccaactgatc tgcgcgcgag gccaagcgat cttcttcttg tccaagataa   660
gcctgtctag cttcaagtat gacgggctga tactgggccg gcaggcgctc cattgcccag   720
tcggcagcga catccttcgg cgcgattttg ccggttactg cgctgtacca aatgcgggac   780
aacgtaagca ctacatttcg ctcatcgcca gcccagtcgg gcggcgagtt ccatagcgtt   840
aaggtttcat ttagcgcctc aaatagatcc tgttcaggaa ccggatcaaa gagttcctcc   900
gccgctggac ctaccaaggc aacgctatgt tctcttgctt ttgtcagcaa gatagccaga   960
tcaatgtcga tcgtggctgg ctcgaagata cctgcaagaa tgtcattgcg ctgccattct  1020
ccaaattgca gttcgcgctt agctggataa cgccacggaa tgatgtcgtc gtgcacaaca  1080
atggtgactt ctacagcgcg gagaatctcg ctctctccag gggaagccga agtttccaaa  1140
aggtcgttga tcaaagctcg ccgcgttgtt tcatcaagcc ttacggtcac cgtaaccagc  1200
aaatcaatat cactgtgtgg cttcaggccg ccatccactg cggagccgta caaatgtacg  1260
gccagcaacg tcggttcgag atggcgctcg atgacgccaa ctacctctga tagttgagtc  1320
gatacttcgg cgatcaccgc ttccctcatg atgtttaact ttgttttagg cgactgcccc  1380
tgctgcgtaa catcgttgct gctccataac atcaaacatc gacccacggc gtaacgcgct  1440
tgctgcttgg atgcccgagg catagactgt accccaaaaa aacagtcata acaagccatg  1500
aaaaccgcca ctgcgccgtt accaccgctg cgttcggtca aggttctgga ccagttgcgt  1560
gagcgcatac gctacttgca ttacagctta cgaaccgaac aggcttatgt ccactgggtt  1620
cgtgccttca tccgtttcca cggtgtgcgt cacccggcaa ccttgggcag cagcgaagtc  1680
gaggcatttc tgtcctggct ggcgaacgag cgcaaggttt cggtctccac gcatcgtcag  1740
gcattggcgg ccttgctgtt cttctacggc aaggtgctgt gcacggatct gccctggctt  1800
caggagatcg gaagacctcg gccgtcgcgg cgcttgccgg tggtgctgac cccggatgaa  1860
gtggttcgca tcctcggttt tctggaaggc gagcatcgtt tgttcgccca gcttctgtat  1920
```

```
ggaacgggca tgcggatcag tgagggtttg caactgcggg tcaaggatct ggatttcgat    1980
cacggcacga tcatcgtgcg ggagggcaag ggctccaagg atcgggcctt gatgttaccc    2040
gagagcttgg cacccagcct gcgcgagcag gggaattaat tcccacgggt tttgctgccc    2100
gcaaacgggc tgttctggtg ttgctagttt gttatcagaa tcgcagatcc ggcttcagcc    2160
ggtttgccgt ctgaaagcgc tatttcttcc agaattgcca tgattttttc cccacgggag    2220
gcgtcactgg ctcccgtgtt gtcggcagct ttgattcgat aagcagcatc gcctgtttca    2280
ggctgtctat gtgtgactgt tgagctgtaa caagttgtct caggtgttca atttcatgtt    2340
ctagttgctt tgttttactg gtttcacctg ttctattagg tgttacatgc tgttcatctg    2400
ttacattgtc gatctgttca tggtgaacag ctttgaatgc accaaaaact cgtaaaagct    2460
ctgatgtatc tatctttttt acaccgtttt catctgtgca tatggacagt tttccctttg    2520
atatgtaacg gtgaacagtt gttctacttt tgtttgttag tcttgatgct tcactgatag    2580
atacaagagc cataagaacc tcagatcctt ccgtatttag ccagtatgtt ctctagtgtg    2640
gttcgttgtt tttgcgtgag ccatgagaac gaaccattga gatcatactt actttgcatg    2700
tcactcaaaa attttgcctc aaaactggtg agctgaattt ttgcagttaa agcatcgtgt    2760 agtgttttc ttagtccgtt atgtaggtag gaatctgatg taatggttgt tggtattttg    2820
tcaccattca tttttatctg gttgttctca agttcggtta cgagatccat ttgtctatct    2880
agttcaactt ggaaaatcaa cgtatcagtc gggcggcctc gcttatcaac caccaatttc    2940
atattgctgt aagtgtttaa atctttactt attggtttca aaaccattg gttaagcctt    3000 ttaaactcat ggtagttatt ttcaagcatt aacatgaact taaattcatc aaggctaatc    3060
tctatatttg cctgtgagt tttcttttgt gttagttctt ttaataacca ctcataaatc    3120
ctcatagagt atttgttttc aaaagactta acatgttcca gattatattt tatgaatttt    3180
tttaactgga aaagataagg caatatctct tcactaaaaa ctaattctaa tttttcgctt    3240
gagaacttgg catagtttgt ccactggaaa atctcaaagc ctttaaccaa aggattcctg    3300
atttccacag ttctcgtcat cagctctctg gttgctttag ctaatacacc ataagcattt    3360
tccctactga tgttcatcat ctgagcgtat tggttataag tgaacgatac cgtccgttct    3420
ttccttgtag ggttttcaat cgtggggttg agtagtgcca cacagcataa aattagcttg    3480
gtttcatgct ccgttaagtc atagcgacta atcgctagtt catttgcttt gaaaacaact    3540
aattcagaca tacatctcaa ttggtctagg tgattttaat cactatacca attgagatgg    3600
gctagtcaat gataattact agctagtcct tttcctttga gttgtgggta tctgtaaatt    3660
ctgctagacc tttgctggaa aacttgtaaa ttctgctaga ccctctgtaa attccgctag    3720
acctttgtgt gttttttttg tttatattca agtggttata atttatagaa taagaaaga    3780 ataaaaaaag ataaaaagaa tagatcccag ccctgtgtat aactcactac tttagtcagt    3840
tccgcagtat tacaaaagga tgtcgcaaac gctgtttgct cctctacaaa acagaccta    3900 aaaccctaaa ggcttaagta gcaccctcgc aagctcgggc aaatcgctga atattccttt    3960
tgtctccgac catcaggcac ctgagtcgct gtcttttcg tgacattcag ttcgctgcgc    4020
tcacggctct ggcagtgaat gggggtaaat ggcactacag gcgccttta tggattcatg    4080 caaggaaact acccataata caagaaaagc ccgtcacggg cttctcaggg cgttttatgg    4140
cgggtctgct atgtggtgct atctgacttt ttgctgttca gcagttcctg ccctctgatt    4200
ttccagtctg accacttcgg attatcccgt gacaggtcat tcagactggc taatgcaccc    4260
```

```
agtaaggcag cggtatcatc aacaggctta cccgtcttac tgtcgggaat tcatttaaat    4320
agtcaaaagc ctccgaccgg aggcttttga ctgctaggcg atctgtgctg tttgccacgg    4380
tatgcagcac cagcgcgaga ttatgggctc gcacgctcga ctgtcggacg ggggcactgg    4440
aacgagaagt caggcgagcc gtcacgccct tgacaatgcc acatcctgag caaataattc    4500
aaccactaaa caaatcaacc gcgtttcccg gaggtaacca agcttgcggg agagaatgat    4560
gaacaagagc caacaagttc agacaatcac cctggccgcc gcccagcaaa tggcggcggc    4620
ggtggaaaaa aaagccactg agatcaacgt ggcggtggtg ttttccgtag ttgaccgcgg    4680
aggcaacacg ctgcttatcc agcggatgga cgaggccttc gtctccagct gcgatatttc    4740
cctgaataaa gcctggagcg cctgcagcct gaagcaaggt acccatgaaa ttacgtcagc    4800
ggtccagcca ggacaatctc tgtacggtct gcagctaacc aaccaacagc gaattattat    4860
ttttggcggc ggcctgccag ttattttttaa tgagcaggta attggcgccg tcggcgttag    4920
cggcggtacg gtcgagcagg atcaattatt agcccagtgc gccctggatt gtttttccgc    4980
attataacct gaagcgagaa ggtatattat gagctatcgt atgttccgcc aggcattctg    5040
agtgttaacg aggggaccgt catgtcgctt tcaccgccag gcgtacgcct gttttacgat    5100
ccgcgcgggc accatgccgg cgccatcaat gagctgtgct gggggctgga ggagcagggg    5160
gtcccctgcc agaccataac ctatgacgga ggcggtgacg ccgctgcgct gggcgccctg    5220
gcggccagaa gctcgcccct gcgggtgggt atcgggctca gcgcgtccgg cgagatagcc    5280
ctcactcatg cccagctgcc ggcggacgcg ccgctggcta ccggacacgt caccgatagc    5340
gacgatcaac tgcgtacgct cggcgccaac gccgggcagc tggttaaagt cctgccgtta    5400
agtgagagaa actgaatgta tcgtatctat acccgcaccg gggataaagg caccaccgcc    5460
ctgtacggcg gcagccgcat cgagaaagac catattcgcg tcgaggccta cggcaccgtc    5520
gatgaactga tatcccagct gggcgtctgc tacgccacga cccgcgacgc cgggctgcgg    5580
gaaagcctgc accatattca gcagacgctg ttcgtgctgg gggctgaact ggccagcgat    5640
gcgcggggcc tgacccgcct gagccagacg atcggcgaag aggagatcac cgccctggag    5700
cggcttatcg accgcaatat ggccgagagc ggcccgttaa acagttcgt gatcccgggg    5760 aggaatctcg cctctgccca gctgcacgtg gcgcgcaccc agtcccgtcg gctcgaacgc    5820
ctgctgacgg ccatggaccg cgcgcatccg ctgcgcgacg cgctcaaacg ctacagcaat    5880
cgcctgtcgg atgccctgtt ctccatggcg cgaatcgaag agactaggcc tgatgcttgc    5940
gcttgaactg gcctagcaaa cacagaaaaa agcccgcacc tgacagtgcg gcttttttt    6000 ttcctaggcg atctgtgctg tttgccacgg tatgcagcac cagcgcgaga ttatgggctc    6060
gcacgctcga ctgtcggacg ggggcactgg aacgagaagt caggcgagcc gtcacgccct    6120
tgacaatgcc acatcctgag caaataattc aaccactaaa caaatcaacc gcgtttcccg    6180
gaggtaacca agcttcacct tttgagccga tgaacaatga aaagatcaaa acgatttgca    6240
gtactggccc agcgccccgt caatcaggac gggctgattg gcgagtggcc tgaagagggg    6300
ctgatcgcca tggacagccc ctttgacccg gtctcttcag taaaagtgga caacggtctg    6360
atcgtcgaac tggacggcaa acgccgggac cagtttgaca tgatcgaccg atttatcgcc    6420
gattacgcga tcaacgttga gcgcacagag caggcaatgc gcctggaggc ggtggaaata    6480
gcccgtatgc tggtggatat tcacgtcagc cgggaggaga tcattgccat cactaccgcc    6540
atcacgccgg ccaaagcggt cgaggtgatg gcgcagatga acgtggtgga gatgatgatg    6600
gcgctgcaga agatgcgtgc ccgccggacc ccctccaacc agtgccacgt caccaatctc    6660
```

```
aaagataatc cggtgcagat tgccgctgac gccgccgagg ccgggatccg cggcttctca    6720
gaacaggaga ccacggtcgg tatcgcgcgc tacgcgccgt ttaacgccct ggcgctgttg    6780
gtcggttcgc agtgcggccg ccccggcgtg ttgacgcagt gctcggtgga agaggccacc    6840
gagctggagc tgggcatgcg tggcttaacc agctacgccg agacggtgtc ggtctacggc    6900
accgaagcgg tatttaccga cggcgatgat acgccgtggt caaaggcgtt cctcgcctcg    6960
gcctacgcct cccgcgggtt gaaaatgcgc tacacctccg gcaccggatc cgaagcgctg    7020
atgggctatt cggagagcaa gtcgatgctc tacctcgaat cgcgctgcat cttcattact    7080
aaaggcgccg gggttcaggg actgcaaaac ggcgcggtga gctgtatcgg catgaccggc    7140
gctgtgccgt cgggcattcg ggcggtgctg gcggaaaacc tgatcgcctc tatgctcgac    7200
ctcgaagtgg cgtccgccaa cgaccagact ttctcccact cggatattcg ccgcaccgcg    7260
cgcaccctga tgcagatgct gccgggcacc gactttattt tctccggcta cagcgcggtg    7320
ccgaactacg acaacatgtt cgccggctcg aacttcgatg cggaagattt tgatgattac    7380
aacatcctgc agcgtgacct gatggttgac ggcggcctgc gtccggtgac cgaggcggaa    7440
accattgcca ttcgccagaa agcggcgcgg gcgatccagg cggttttccg cgagctgggg    7500
ctgccgccaa tcgccgacga ggaggtggag gccgccacct acgcgcacgg cagcaacgag    7560
atgccgccgc gtaacgtggt ggaggatctg agtgcggtgg aagagatgat gaagcgcaac    7620
atcaccggcc tcgatattgt cggcgcgctg agccgcagcg gctttgagga tatcgccagc    7680
aatattctca atatgctgcg ccagcgggtc accggcgatt acctgcagac ctcggccatt    7740
ctcgatcggc agttcgaggt ggtgagtgcg gtcaacgaca tcaatgacta tcaggggccg    7800
ggcaccggct atcgcatctc tgccgaacgc tgggcggaga tcaaaaatat tccgggcgtg    7860
gttcagcccg acaccattga ataaggcggt attcctgtgc aacagacaac ccaaattcag    7920
ccctctttta ccctgaaaac ccgcgagggc ggggtagctt ctgccgatga acgcgccgat    7980
gaagtggtga tcggcgtcgg ccctgccttc gataaacacc agcatcacac tctgatcgat    8040
atgccccatg gcgcgatcct caaagagctg attgccgggg tggaagaaga ggggcttcac    8100
gcccgggtgg tgcgcattct gcgcacgtcc gacgtctcct ttatggcctg ggatgcggcc    8160
aacctgagcg gctcggggat cggcatcggt atccagtcga aggggaccac ggtcatccat    8220
cagcgcgatc tgctgccgct cagcaacctg gagctgttct cccaggcgcc gctgctgacg    8280
ctggagacct accggcagat tggcaaaaac gctgcgcgct atgcgcgcaa agagtcacct    8340
tcgccggtgc cggtggtgaa cgatcagatg gtgcggccga aatttatggc caaagccgcg    8400
ctatttcata tcaaagagac caaacatgtg gtgcaggacg ccgagcccgt cacccctgcac    8460
atcgacttag taagggagtg accatgagcg agaaaaccat gcgcgtgcag gattatccgt    8520
tagccacccg ctgcccggag catatcctga cgcctaccgg caaaccattg accgatatta    8580
ccctcgagaa ggtgctctct ggcgaggtgg gcccgcagga tgtgcggatc tcccgccaga    8640
cccttgagta ccaggcgcag attgccgagc agatgcagcg ccatgcggtg gcgcgcaatt    8700
tccgccgcgc ggcggagctt atcgccattc ctgacgagcg cattctggct atctataacg    8760
cgctgcgccc gttccgctcc tcgcaggcgg agctgctggc gatcgccgac gagctggagc    8820
acacctggca tgcgacagtg aatgccgcct ttgtccggga gtcggcggaa gtgtatcagc    8880
agcggcataa gctgcgtaaa ggaagctaag cggaggtcag catgccgtta atagccggaa    8940
ttgatatcgg caacgccacc accgaggtgg cgctggcgtc cgactacccg caggcgaggg    9000
```

```
cgtttgttgc cagcgggatc gtcgcgacga cgggcatgaa agggacgcgg gacaatatcg    9060
ccgggaccct cgccgcgctg gagcaggccc tggcgaaaac accgtggtcg atgagcgatg    9120
tctctcgcat ctatcttaac gaagccgcgc cggtgattgg cgatgtggcg atggagacca    9180
tcaccgagac cattatcacc gaatcgacca tgatcggtca taacccgcag acgccgggcg    9240
gggtgggcgt tggcgtgggg acgactatcg ccctcgggcg gctggcgacg ctgccggcgg    9300
cgcagtatgc cgaggggtgg atcgtactga ttgacgacgc cgtcgatttc cttgacgcca    9360
tgtggtggct caatgaggcg ctcgaccggg ggatcaacgt ggtggcggcg atcctcaaaa    9420
aggacgacgg cgtgctggtg aacaaccgcc tgcgtaaaac cctgccggtg gtggatgaag    9480
tgacgctgct ggagcaggtc cccgaggggg taatggcggc ggtggaagtg gccgcgccgg    9540
gccaggtggt gcggatcctg tcgaatccct acgggatcgc caccttcttc gggctaagcc    9600
cggaagagac ccaggccatc gtccccatcg cccgcgccct gattggcaac cgttccgcgg    9660
tggtgctcaa gaccccgcag ggggatgtgc agtcgcgggt gatcccggcg ggcaacctct    9720
acattagcgg cgaaaagcgc cgcggagagg ccgatgtcgc cgagggcgcg gaagccatca    9780
tgcaggcgat gagcgcctgc gctccggtac gcgacatccg cggcgaaccg ggcacccacg    9840
ccggcggcat gcttgagcgg gtgcgcaagg taatggcgtc cctgaccggc catgagatga    9900
gcgcgatata catccaggat ctgctggcgg tggatacgtt tattccgcgc aaggtgcagg   9960
gcgggatggc cggcgagtgc gccatggaga atgccgtcgg gatggcggcg atggtgaaag   10020
cggatcgtct gcaaatgcag gttatcgccc gcgaactgag cgcccgactg cagaccgagg   10080
tggtggtggg cggcgtggag gccaacatgg ccatcgccgg ggcgttaacc actcccggct   10140
gtgcggcgcc gctggcgatc ctcgacctcg gcgccggctc gacggatgcg gcgatcgtca   10200
acgcggaggg gcagataacg gcggtccatc tcgccggggc ggggaatatg gtcagcctgt   10260
tgattaaaac cgagctgggc ctcgaggatc tttcgctggc ggaagcgata aaaaaatacc   10320
cgctggccaa agtggaaagc ctgttcagta ttcgtcacga gaatggcgcg gtggagttct   10380
ttcgggaagc cctcagcccg gcggtgttcg ccaaagtggt gtacatcaag gagggcgaac   10440
tggtgccgat cgataacgcc agcccgctgg aaaaaattcg tctcgtgcgc cggcaggcga   10500
aagagaaagt gtttgtcacc aactgcctgc gcgcgctgcg ccaggtctca cccgcggtt   10560
ccattcgcga tatcgccttt gtggtgctgg tgggcggctc atcgctggac tttgagatcc   10620
cgcagcttat cacggaagcc ttgtcgcact atggcgtggt cgccgggcag ggcaatattc   10680
ggggaacaga agggccgcgc aatgcggtcg ccaccgggct gctactggcc ggtcaggcga   10740
attaaacggg cgctcgcgcc agcctctagg tacaaataaa aaaggcacgt cagatgacgt   10800
gccttttttc ttgtctagcg tgcaccaatg cttctggcgt caggcagcca tcggaagctg   10860
tggtatggct gtgcaggtcg taaatcactg cataattcgt gtcgctcaag gcgcactccc   10920
gttctggata atgttttttg cgccgacatc ataacggttc tggcaaatat ctgaaatga    10980
gctgttgaca attaatcatc cggctcgtat aatgtgtgga attgtgagcg ataacaatt    11040
tcacacagga aacagaccat gactagtaag gaggacaatt ccatggctgc tgctgctgat   11100
agattaaact taacttccgg ccacttgaat gctggtagaa agagaagttc ctcttctgtt   11160
tctttgaagg ctgccgaaaa gcctttcaag gttactgtga ttggatctgg taactggggt   11220
actactattg ccaaggtggt tgccgaaaat tgtaagggat acccagaagt tttcgctcca   11280
atagtacaaa tgtgggtgtt cgaagaagag atcaatggtg aaaaattgac tgaaatcata   11340
aatactagac atcaaaacgt gaaatacttg cctggcatca ctctacccga caatttggtt   11400
```

```
gctaatccag acttgattga ttcagtcaag gatgtcgaca tcatcgtttt caacattcca   11460
catcaatttt tgccccgtat ctgtagccaa ttgaaaggtc atgttgattc acacgtcaga   11520
gctatctcct gtctaaaggg ttttgaagtt ggtgctaaag gtgtccaatt gctatcctct   11580
tacatcactg aggaactagg tattcaatgt ggtgctctat ctggtgctaa cattgccacc   11640
gaagtcgctc aagaacactg gtctgaaaca acagttgctt accacattcc aaaggatttc   11700
agaggcgagg gcaaggacgt cgaccataag gttctaaagg ccttgttcca cagaccttac   11760
ttccacgtta gtgtcatcga agatgttgct ggtatctcca tctgtggtgc tttgaagaac   11820
gttgttgcct taggttgtgg tttcgtcgaa ggtctaggct ggggtaacaa cgcttctgct   11880
gccatccaaa gagtcggttt gggtgagatc atcagattcg gtcaaatgtt tttcccagaa   11940
tctagagaag aaacatacta ccaagagtct gctggtgttg ctgatttgat caccacctgc   12000
gctggtggta gaaacgtcaa ggttgctagg ctaatggcta cttctggtaa ggacgcctgg   12060
gaatgtgaaa aggagttgtt gaatggccaa tccgctcaag gtttaattac ctgcaaagaa   12120
gttcacgaat ggttggaaac atgtggctct gtcgaagact cccattatt tgaagccgta   12180 taccaaatcg tttacaacaa ctacccaatg aagaacctgc cggacatgat tgaagaatta   12240
gatctacatg aagattagat ttattggatc caggaaacag actagaatta tgggattgac   12300
tactaaacct ctatctttga aagttaacgc cgctttgttc gacgtcgacg gtaccattat   12360
catctctcaa ccagccattg ctgcattctg gagggatttc ggtaaggaca aaccttattt   12420
cgatgctgaa cacgttatcc aagtctcgca tggttggaga acgtttgatg ccattgctaa   12480
gttcgctcca gactttgcca atgaagagta tgttaacaaa ttagaagctg aaattccggt   12540
caagtacggt gaaaaatcca ttgaagtccc aggtgcagtt aagctgtgca acgctttgaa   12600
cgctctacca aaagagaaat gggctgtggc aacttccggt acccgtgata tggcacaaaa   12660
atggttcgag catctgggaa tcaggagacc aaagtacttc attaccgcta atgatgtcaa   12720
acagggtaag cctcatccag aaccatatct gaagggcagg aatggcttag gatatccgat   12780
caatgagcaa gaccctttcca aatctaaggt agtagtattt gaagacgctc cagcaggtat   12840
tgccgccgga aaagccgccg gttgtaagat cattggtatt gccactactt tcgacttgga   12900
cttcctaaag gaaaaaggct gtgacatcat tgtcaaaaac cacgaatcca tcagagttgg   12960
cggctacaat gccgaaacag acgaagttga attcatttt gacgactact tatatgctaa   13020
ggacgatctg ttgaaatggt aacccgggct gcaggcatgc aagcttggct gttttggcgg   13080
atgagagaag attttcagcc tgatacagat taaatcagaa cgcagaagcg gtctgataaa   13140
acagaatttg cctggcggca gtagcgcggt ggtcccacct gaccccatgc cgaactcaga   13200
agtgaaacgc cgtagcgccg atggtagtgt ggggtctccc catgcgagag tagggaactg   13260
ccaggcatca aataaaacga aaggctcagt cgaaagactg ggcctttcgt tttatctgtt   13320
gtttgtcggt gaacgctctc ctgagtagga caaatccgcc gggagcggat ttgaacgttg   13380
cgaagcaacg gcccggaggg tggcgggcag gacgcccgcc ataaactgcc aggcatcaaa   13440
ttaagcagaa ggccatcctg acggatggcc tttttgcgtt tctacaaact ccagctggat   13500
cgggcgctag agtatacatt taaatggtac cggcgcgccg ctagcttaat taacggaccg   13560
atgcatgagc tcacgcgtac cggtgctctt cgatctacgt aagaaggcct t           13611
```

<210> SEQ ID NO 79
<211> LENGTH: 4490
<212> TYPE: DNA

<213> ORGANISM: artificial sequence
<220> FEATURE:
<223> OTHER INFORMATION: plasmid

<400> SEQUENCE: 79

```
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg gacaaattct     300
tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt ccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagct gcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta    1980
tgtgtgactt tgagctgta acaagttgtc tcagtgttc aatttcatgt tctagttgct    2040
ttgtttact ggtttcacct gttctattag gtgttacatg ctgttcatct gttacattgt    2100
cgatctgttc atggtgaaca gctttgaatg caccaaaaac tcgtaaaagc tctgatgtat    2160
ctatcttttt tacaccgttt tcatctgtgc atatggacag ttttcccttt gatatgtaac    2220
```

```
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag ccttttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtccttt cctttgagtt gtgggtatct gtaaattctg ctagaccttt   3360 gctgaaaac ttgtaaattc tgctagaccc tctgtaaatt ccgctagacc tttgtgtgtt   3420 tttttgttt atattcaagt ggttataatt tatagaataa agaaagaata aaaaagata   3480 aaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgatttc cagtctgacc   3900 acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctagcaaaca cagaaaaaag cccgcacctg acagtgcggg   4080 ctttttttt cctaggtaca aataaaaaag gcacgtcaga tgacgtgcct tttttcttgt   4140
ctagagtata catttaaatg gtaccctcta gtcaaggcct taagtgagtc gtattacgga   4200
ctggccgtcg ttttacaacg tcgtgactgg gaaaaccctg gcgttaccca acttaatcgc   4260
cttgcagcac atccccttt cgccagctgg cgtaatagcg aagaggcccg caccgatcgc   4320
ccttcccaac agttgcgcag cctgaatggc gaatggcgcc tgatgcggta ttttctcctt   4380
acgcatctgt gcggtatttc acaccgcata tggtgcactc tcagtacaat ctgctctgat   4440
gccgcatagt taagccagcc ccgacacccg ccaacacccg ctgacgagct           4490
```

<210> SEQ ID NO 80

-continued

```
<211> LENGTH: 33
<212> TYPE: DNA
<213> ORGANISM: artificial sequence
<220> FEATURE:
<223> OTHER INFORMATION: primer

<400> SEQUENCE: 80
cataagcttg cgggagagaa tgatgaacaa gag                                    33

<210> SEQ ID NO 81
<211> LENGTH: 31
<212> TYPE: DNA
<213> ORGANISM: artificial sequence
<220> FEATURE:
<223> OTHER INFORMATION: primer

<400> SEQUENCE: 81
acgcctaggc cagttcaagc gcaagcatca g                                      31

<210> SEQ ID NO 82
<211> LENGTH: 25
<212> TYPE: DNA
<213> ORGANISM: artificial sequence
<220> FEATURE:
<223> OTHER INFORMATION: primer

<400> SEQUENCE: 82
ctttaatctg cacaccccaa cccgc                                             25

<210> SEQ ID NO 83
<211> LENGTH: 25
<212> TYPE: DNA
<213> ORGANISM: artificial sequence
<220> FEATURE:
<223> OTHER INFORMATION: primer

<400> SEQUENCE: 83
ggcggtatca atcgagcgat aaccc                                             25
```

PROMOTER AND PLASMID SYSTEM FOR GENETIC ENGINEERING

This application claims the benefit of U.S. Provisional Application No. 60/374,931, filed Apr. 22, 2002.

FIELD OF THE INVENTION

This invention is in the field of molecular biology. More specifically, this invention pertains to a series of low-copy-number plasmids comprising restriction endonuclease recognition sites useful for cloning at least three different genes or operons, each site flanked by a terminator sequence and a set of promoters for varying levels of protein expression. The invention is useful for genetic engineering in microorganisms, especially where multiple genetic insertions are sought.

BACKGROUND OF THE INVENTION

Molecular biotechnology is a discipline that is based on the ability of researchers to transfer specific units of genetic information from one organism to another. This process, known as cloning, relies on the techniques of recombinant DNA technology to produce a useful product or a commercial process (Glick, B. R.; Pasternak, J. J., *Molecular Biotechnology Principles and Applications of Recombinant* DNA, 2$^{nd}$ ed. American Society for Microbiology, Washington, D.C. (1998)).

Commercial processes often require that proteins encoded by the cloned gene are produced at high rates of expression. There is no single strategy for achieving maximal expression of every cloned gene. Most cloned genes have distinctive molecular properties that require the investment of considerable time and effort before a specific set of conditions that result in an acceptable level of expression is found.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: (1) the nature of the relevant transcriptional promoter and terminator sequences, (2) the strength of the ribosome binding site, (3) the number of copies of the cloned gene and whether the gene is plasmid-borne or integrated into the genome of the host cell, (4) the final cellular location of the synthesized foreign protein, (5) the efficiency of translation in the host organism, and (6) the intrinsic stability of the cloned gene protein within the host cell.

Additionally, the introduction and expression of foreign DNA in a host organism often changes the metabolism of the organism in ways that may impair normal cellular functioning. This phenomenon is due to a metabolic load or burden imposed upon the host by the foreign DNA. The metabolic load may result from a variety of conditions including 1) increasing plasmid copy number, 2) overproduction of proteins, 3) saturation of export sites, and/or 4) interference of cellular function by the foreign protein itself.

Techniques to address some of the obstacles presented above are known. Several groups have used multiple promoters in tandem to express genes at different phases of cell growth (CN 1186856), from different RNA polymerases or in different phage species (U.S. Pat. No. 5,547,862; *J. Biotechnol.* 2(5):303-316 (1985); *Biotechniques*, 18(1):152-154, 156-157(1995)). Another group has used tandem repeated multiple cloning sites (MCS) (*Gene*, 139 (1):83-86 (1994)) to facilitate moving DNA in and out of the plasmid vector. One group has reported the use of a high-copy-number vector with three multiple cloning sites each behind a different promoter for expression of different genes in mammalian cells (*Biotech. Bioeng.*, 57(1):1-10 (1998)).

Despite these techniques, the problem to be solved remains how to easily and quickly clone multiple genes or operons while minimizing the impact of metabolic load, controlling the yield of the recombinant protein to meet production needs, and enhancing the stability of the transformed host cell.

SUMMARY OF THE INVENTION

Applicants have created novel glucose isomerase promoter sequences that allow varying levels of gene expression in production organisms. Applicants incorporated expression cassettes containing the variant GI promoters into a low-copy-number plasmid derived from pCL1920 to construct a series of plasmids for genetic engineering. Transcription terminators isolate the associated promoter from transcription from other promoters located outside this construct.

Applicants also have constructed a unique nucleotide sequence containing cloning sites for multiple rare restriction enzymes, further facilitating cloning in this construct or transfer of this construct to alternate plasmid or vector backbones. The unique cloning sites allow introduction of genes or operons to be expressed under the control of suitable promoters of varying strengths.

The invention encompasses:

1. an isolated or recombinant nucleic acid molecule encoding a *Streptomyces lividins* glucose isomerase variant, the nucleic acid molecule selected from the group consisting of SEQ ID NOS:9-28;

2. an isolated or recombinant nucleic acid molecule encoding a *Streptomyces lividins* glucose isomerase variant, the nucleic acid molecule comprising a nucleotide sequence of any of SEQ ID NOs:9-28;

3. a library of isolated or recombinant nucleic acid molecules encoding a *Streptomyces lividins* glucose isomerase variant, the library comprising the nucleotide sequences of SEQ ID NOS:9-28;

4. an expression cassette comprising the nucleic acid molecule of the various GI variants set out above, and;

5. a kit comprising the nucleic acid molecules encoding the various *Streptomyes lividins* glucose isomerase variants set out above.

A further embodiment of the invention is a DNA construct comprising at least three transcriptional terminators and at least one cloning site situated between any two transcriptional terminators. A preferred embodiment of this DNA construct comprises the transcriptional terminators tonB, thrA, or aspA, and the cloning sites are selected from the group consisting of AvrIl, NheI, BfaI, Cac8I, BsaJI, and StyI. Preferred cloning sites are NheI or AvrIl. A library of these constructs is also encompassed in the invention.

The invention includes the following DNA constructs:
the pSYCO109mcs plasmid consisting of SEQ ID NO:30,
the short 1.5 GI promoter consisting of SEQ ID NO:31,
the short 1.20 GI promoter consisting of SEQ ID NO:32,
the pAH105 plasmid consisting of SEQ ID NO:70,
the pSYCO101 plasmid consisting of SEQ ID NO:71,
the pSYCO103 plasmid consisting of SEQ ID NO:72,
the pSYCO106 plasmid consisting of SEQ ID NO:73,
the pSYCO109 plasmid consisting of SEQ ID NO:74, the pSCYO106mcs plasmid consisting of SEQ ID NO:78, and the pRJ50 plasmid consisting of SEQ ID NO:79.

A further embodiment of the invention is a vector having a multiple cloning site containing restriction recognition site sequences specific for the restriction endonucleases AscI, NheI, PacI, RsrII, NsiI, SacII, MluI, AgeI, SapI, and SnaBI. A particular embodiment of this vector is the nucleotide sequence of SEQ ID NO:77.

The genetic materials of this invention include transformed host cells containing the nucleic acid molecules described above and the polypeptides encoded by the polynucleotides.

BRIEF DESCRIPTION OF THE SEQUENCE LISTING AND BIOLOGICAL DEPOSIT

Applicants have provided 83 sequences in conformity with Rules for the Standard Representation of Nucleotide and Amino Acid Sequences in Patent Applications (Annexes I and II to the Decision of the President of the EPO, published in Supplement No. 2 to OJ EPO, Dec. 1992), with 37 C.F.R. 1.821-1.825and Appendices A and B (Requirements for Application Disclosures Containing Nucleotides and/or Amino Acid Sequences) with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference.

SEQ ID NO:1 is the nucleotide sequence for the wildtype *Streptomyces lividans* glucose isomerase (GI) promoter.

SEQ ID NOs:2-8 are oligonucleotide primers used for saturation mutagenesis of the GI promoter. In SEQ ID NOs: 3-8, "N" represents either A, T, C, or G.

SEQ ID NOs:9-28 are nucleotide sequences for the GI promoter variants.

SEQ ID NO:29 is the nucleotide sequence for the yqhD gene from *E. coli*.

SEQ ID NO:30 is the nucleotide sequence for the pSYCO109mcs plasmid.

SEQ ID NO:31 is the nucleotide sequence for the short 1.5 GI promoter.

SEQ ID NO:32 is the nucleotide sequence for the short 1.20 GI promoter.

SEQ ID NO:33 is the nucleotide sequence for the short wild-type GI promoter.

SEQ ID NOs:34-37 are the oligonucleotide primers used for amplification of yqhD with incorporation of the short GI promoters.

SEQ ID NOs:38-39 are oligonucleotide primers used to construct the yqhD disruption.

SEQ ID NOs:40-43 are oligonucleotide primers used to confirm disruption of yqhD.

SEQ ID NOs:44-46 are oligonucleotide primers used for replacement of the chromosomal ppc promoter with the short wild-type GI promoter.

SEQ ID NO:47 is the nucleotide sequence for a multiple cloning site and terminator.

SEQ ID NO:48 is the nucleotide sequence for the pHK28-26 plasmid.

SEQ ID NOs:49-50 are oligonucleotide primers used to amplify dhaB3.

SEQ ID NOs:51-52 are oligonucleotide primers used to amplify dhaB1.

SEQ ID NOs:53-54 are oligonucleotide primers used to create the dhaT deletion.

SEQ ID NOs:55-56 are oligonucleotides used to create a linker.

SEQ ID NO:57 is a nucleotide sequence encoding three transcriptional terminators separated by restriction sites.

SEQ ID NOs:58-59 are oligonucleotides used to create SEQ ID NO:60.

SEQ ID NO:60 is the nucleotide sequence encoding three transcriptional terminators flanked by EcoRI and KpnI sites.

SEQ ID NOs:61-62 are oligonucleotide primers used to amplify SEQ ID NO:60.

SEQ ID NOs:63-66 are oligonucleotide primers used to amplify an expression cassette.

SEQ ID NO:67 is the nucleotide sequence of a double-stranded linker used to generate pCR-pCL1920.

SEQ ID NOs:68-69 are oligonucleotide primers used to amplify the rrnBT1 T2 terminator from pTrc99A.

SEQ ID NO:70 is the nucleotide sequence for the pAH105 plasmid.

SEQ ID NO:71 is the nucleotide sequence for the pSYCO101 plasmid.

SEQ ID NO:72 is the nucleotide sequence for the pSYCO103 plasmid.

SEQ ID NO:73 is the nucleotide sequence for the pSYCO106 plasmid.

SEQ ID NO:74 is the nucleotide sequence for the pSYCO109 plasmid.

SEQ ID NOs:75-76 are oligonucleotide primers used to form SEQ ID NO:77.

SEQ ID NO:77 is the nucleotide sequence of a multiple cloning fragment containing restriction recognition sites for the following enzymes: NheI, RsrII, SacI, AgeI, SnaBI, AscI, PacI, NsiI, MluI, and SapI.

SEQ ID NO:78 is the nucleotide sequence for the pSCYO106mcs plasmid.

SEQ ID NO:79 is the nucleotide sequence for the pRJ50 plasmid.

SEQ ID NOs:80-81 are oligonucleotide primers used to amplify the orf operon.

SEQ ID NOs:82-83 are oligonucleotide primers to check transformants in Example 4.

Applicants have made the following biological deposit under the terms of the Budapest Treaty on the International Recognition of the Deposit of Microorganisms for the Purposes of Patent Procedure:

| Depositor Identification Reference | Int'l. Depository Designation | Date of Deposit |
|---|---|---|
| *Escherichia coli* RJ8n | ATCC PTA-4216 | 9 Apr. 2002 |

As used herein, "ATCC" refers to the American Type Culture Collection International Depository located 10801 University Blvd., Manassas, Va. 20110-1109, U.S.A. The "ATCC No." is the accession number to cultures on deposit with the ATCC.

The listed deposits will be maintained in the indicated international depository for at least thirty (30) years and will be made available to the public upon grant of a patent disclosing it. The availability of a deposit does not constitute a license to practice the subject invention in derogation of patent rights granted by government action.

DETAILED DESCRIPTION OF THE INVENTION

The Applicants have solved the stated problem by creating a series of constructs containing at least three unique cloning sites, each cloning site operably separated from each other by transcription terminators and promoters of different strengths. The promoters of different strengths are variants of the *Streptomyces lividans* glucose isomerase (GI) promoter (SEQ ID NO:1). Combining the variant GI promoters in expression cassettes with a SYCO plasmid as the production platform provides a system useful for biocatalyst development in a wide variety of bioprocess projects.

The invention allows the facile and stable incorporation of endogenous or exogenous genes or operons in a vector controlling the levels of gene expression. The use of the single plasmid to express multiple genes or operons reduces the number of antibiotic markers needed to maintain the multiple plamids in the *E. coli* host that previous methods required to produce a gene product. Use of the invention can minimize the impact of metabolic load, optimize the yield of the recombinant protein, and enhance the stability of the transformed host cell. The invention is especially useful for genetic engineering in bioprocesses where expressing two or more genes or operons may be required for product formation.

Applicants have created novel GI promoter sequences that allow varying levels of gene expression. Applicants incorporated expression cassettes containing the variant GI promoters into a low-copy-number plasmid derived from pCL1920 to construct a series of plasmids for genetic engineering. The transcription terminators isolate the associated promoter from transcription from other promoters located outside this construct.

Applicants also have constructed a unique nucleotide sequence containing cloning sites for at least ten rare restriction enzymes, further facilitating cloning in this construct or transfer of this construct to alternate plasmid or vector backbones. The unique cloning sites allow introduction of genes or operons to be expressed under the control of suitable promoters of varying strengths. Further, a given construct may be flanked by unique cloning sites for facile integration into any number of plasmid backbones including pUC, pBR322, pACYC, pSC101, or others known and contemplated by those skilled in the art.

Applicants have demonstrated a specific utility of the invention in the biosynthesis of 1,3-propanediol (3G) from glucose in *E. coli* transformed with the claimed materials. Expression cassettes were constructed in a low-copy-number plasmid as described herein and genes for production of 1,3-propanediol were cloned into this vector. The invention may be used to vary gene expression in other expression systems.

Definitions

The following definitions and abbreviations are to be used to interpret the claims and specification.

"Open reading frame" is abbreviated ORF.

"Polymerase chain reaction" is abbreviated PCR.

The terms "host cell" or "host organism" refer to a microorganism capable of receiving foreign or heterologous genes or multiple copies of endogenous genes and of expressing those genes to produce an active gene product.

The terms "DNA construct" or "construct" refer to an artificially constructed fragment of DNA "Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign", "exogenous", or "heterologous" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure. A "gene construct" refers to a nucleic acid fragment that encodes for expression of one or more specific proteins. In the gene construct the gene may be native, chimeric, or foreign in nature.

The term "isolated nucleic acid" refers to a nucleic acid (e.g., an RNA, DNA, or a mixed polymer) which is substantially separated from other components that naturally accompany a native sequence (e.g., ribosomes, polymerases, and/or flanking genomic sequences from the originating species). The term includes recombinant or cloned DNA isolates and chemically synthesized analogs or analogs biologically synthesized by heterologous systems.

The terms "encoding" and "coding" refer to the process by which a gene, through the mechanisms of transcription and translation, produces an amino acid sequence. The process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue (such as glycine), or a more hydrophobic residue (such as valine, leucine, or isoleucine). Similarly, changes that result in substitution of one negatively charged residue for another (such as aspartic acid for glutamic acid), or one positively charged residue for another (such as lysine for arginine) can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The term "promoter" refers to a region of DNA to which RNA polymerase binds and initiates the transcription of a gene.

The terms "transcription terminator" or "terminator" refer to the genetic element that ends protein synthesis.

The term "operon" refers to a cluster of genes that are coordinately regulated.

The terms "polypeptide" and "protein" are used interchangeably to refer to the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences (linear or circular) of a single- or double-stranded DNA or RNA, derived from any source. Such elements contain a number of nucleotide sequences that have been joined or recombined into a unique construction capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in its host.

The term "restriction endonucleases" refers to a class of enzymes that cut a given length of DNA at a specific and unique internal location. By creating the cut in the DNA, restriction endonucleases enable the subsequent splicing or insertion of segments of DNA into the internal location. The terms "restriction site" or "restriction recognition site" refer to a nucleotide sequence (of base pairs) in a DNA molecule that is "recognized" and cut by a given restriction enzyme.

The term "rare", as applied to restriction enzyme sites, refers to the low frequency of occurrence of a given sequence in a gene. A preferred group of rare restriction enzymes sites for purposes of this specification are AscI, NheI, PacI, RsrII, NsiI, SacII, MluI, AgeI, SapI, and SnaBI.

The term "cloning site" refers to a location on a vector into which DNA can be inserted. The term "multiple cloning site" or "mcs" refers to a synthetic DNA sequence that contains any one or a number of different restriction enzyme sites to permit insertion at a defined locus (the restriction site) on a vector. The term "unique cloning site" refers to a cloning site that appears one time with a given DNA sequence.

In describing the relative locations of the elements of a vector, a given site or locus of interest is "between" two others if it is situated in the intermediate length of DNA that separates the two others. In the case of a circular vector, the given site or locus of interest is "between" two others if it is situated within the shortest length of DNA that separates the two other sites on the vector. The given site or locus is said to be "flanked" by another situated either preceding or following the site or locus of interest.

The term "genetically altered" refers to the process of changing hereditary material by transformation or mutation. The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The terms "glycerol dehydratase" or "dehydratase enzyme" refer to the polypeptide(s) responsible for a coenzyme $B_{12}$-dependent enzyme activity that is capable of isomerizing or converting a glycerol molecule to the product 3-hydroxypropionaldehyde. For the purposes of the present invention, the dehydratase enzymes include a glycerol dehydratase (GenBank U09771, U30903) and a diol dehydratase (GenBank D45071) having preferred substrates of glycerol and 1,2-propanediol, respectively. Glycerol dehydratase of K. pneumoniae ATCC 25955 is encoded by the genes dhaB1, dhaB2, and dhaB3 (GenBank U30903). The dhaB1, dhaB2 and dhaB3 genes code for the $\alpha$, $\beta$, and $\gamma$ subunits of the glycerol dehydratase enzyme, respectively. Glycerol dehydratase and diol dehydratase are complexes (with an $\alpha_2\beta_2\gamma_2$ subunit composition) that utilize coenzyme B12.

Glycerol and diol hydratases are subject to mechanism-based suicide inactivation by glycerol and some other substrates (Daniel et al., FEMS Microbiol. Rev. 22:553 (1999)). The term "dehydratase reactivation factor" refers to those proteins responsible for reactivating the dehydratase activity. The terms "dehydratase reactivating activity", "reactivating the dehydratase activity", or "regenerating the dehydratase activity" refer to the phenomenon of converting a dehydratase not capable of catalysis of a substrate to one capable of catalysis of a substrate or to the phenomenon of inhibiting the inactivation of a dehydratase or the phenomenon of extending the useful half-life of the dehydratase enzyme in vivo. Two proteins have been identified as being involved as the dehydratase reactiviation factor (see WO 9821341 (U.S. Pat. No. 6,013,494 herein incorporated by reference) and references therein; Daniel et al., supra; Toraya and Mori, J. Biol. Chem. 274:3372 (1999); and Tobimatsu et al., J. Bacteriol. 181:4110 (1999)).

The terms "oxidoreductase" or "1,3-propanediol oxidoreductase" refer to the polypeptide(s) responsible for an enzyme activity that is capable of catalyszing the reduction of 3-hydroxypropionaldehyde to 1,3-propanediol. 1,3-Propanediol oxidoreductase includes, for example, the polypeptide encoded by the dhat gene (GeneBank U09771, U30903). Alternatively, yqhD, an E. coli open reading frame with 40% identity to the gene adhB in Clostridium (a probable NADH-dependent butanol dehydratase 2), encodes a polypeptide that functions as a 1,3-propanediol oxidoreductase (WO 0112833).

The enzymes expressed by the pSYCO plasmids (pSYCO101, pSYCO103, pSYCO106, pSYCO109, pSYCO106mcs, and pSYCO109mcs) can all be said to comprise genes required to express glycerol dehydratase, dehydratase reactiviation factor, glycerol-3-phosphate dehydrogenase, and glycerol-3-phosphatase.

The terms "fermentable carbon substrate" and "fermentable carbon source" refer to a carbon source capable of being metabolized by host organisms of the present invention and particularly carbon sources selected from the group consisting of monosaccharides, oligosaccharides, polysaccharides, glycerol, dihydroxyacetone and one-carbon substrates or mixtures thereof.

Gene Expression System with GI Promoter Variants of Differing Strengths

The minimal requirement for an effective gene expression system is the presence of a promoter (a site on DNA where the RNA polymerase binds and begins transcription) upstream from a cloned gene. Often a strong promoter, one that has a high affinity for RNA polymerase, is used with the result that the adjacent downstream region is highly or frequently transcribed.

In the promoter, the main sequence determinant of promoter strength (the level at which the downstream gene is transcribed) is the most highly conserved base pairs. Promoters that have deviations from the conserved sequences have decreased transcription initiation frequency (Hawley, D. K.; McClure, W. R., *Nucleic Acids Res.*, 11:2237-2255 (1983)).

Promoters for *E. coli* RNA polymerase have been shown to contain two regions of conserved DNA sequences, located about 10 and 35 base pairs upstream of the transcription start site. Twelve base pairs were determined to be the most highly conserved among promoters. These bases are TTGACA around 35 base pairs upstream, the so called −35 region, and TATMT around 10 base pairs upstream, the so called −10 region. Optimum spacing between the −10 and −35 regions is 17 base pairs. The promoter is stronger if the spacing is closer to 17 base pairs; however, promoters with interspacings of 15 and 20 base pairs retain partial function.

Applicants have created a series of constructs incorporating variants of the *Streptomyces lividans* glucose isomerase (GI) promoter. The constructs form a library or kit of promoter variants with a range of different strengths conferring the ability to tailor varying levels of gene expression as needed. The *Streptomyces* glucose isomerase (EC 5.3.1.9) catalyzes the conversion of glucose-6-phosphate to fructose-6-phosphate. Transcription of the gene encoding phosphoglucose isomerase (pgi) is controlled by a promoter that contains a characteristic −10 signature sequence (AATMT) and a characteristic −35 signature sequence (TTGACA). Although saturation mutagenesis was carried out in the −35 region of the promoter, changes to a SpeI restriction site approximately 122 bp upstream from the −35 region also had effects on expressed gene activity. Further, a 25 bp deletion between the −10 and the end of this promoter allowed retention of 86% of the enzyme's activity even with the changes to the SpeI restriction site. These particular results had not been previously reported.

Transcription termination of RNA synthesis occurs at specific base sequences on the DNA and regulates termination of transcription. A common termination sequence on the DNA is one containing an inverted repeat with a central non-repeating segment. When such a DNA sequence is transcribed, the RNA can form a stem-loop structure by intrastrand base pairing. When such stem-loop structures in the RNA are followed by runs of uridines, they are effective transcription terminators. Other termination sites are regions where a GC-rich sequence is followed by an AT-rich sequence. Such kinds of structures lead to termination of transcription without adding any extra factors and are sometimes termed intrinsic terminators or rho-independent terminators.

Other types of terminator sequences have been discovered that require protein factors like Rho from *E. coli* in addition to RNA polymerase to function. Rho does not bind to RNA polymerase or to DNA but binds tightly to RNA and moves down the chain towards the RNA polymerase-DNA complex. Once RNA polymerase has paused at a Rho-dependent termination site, Rho can then cause the RNA and polymerase to leave the DNA, thus terminating transcription. Other proteins involved in transcription termination are, like Rho, RNA-binding proteins. In all cases the sequences involved in termination operate at the level of RNA. However, RNA is transcribed from DNA, and so transcription termination is ultimately determined by specific nucleotide sequences on the DNA. (Madigan, M. T.; Martinko, J. M.; Parker, J.; *Brock Biology of Microorganisms*, 8$^{th}$ ed., Prentice Hall; Upper Saddle River, N.J. (1997)).

Applicants have constructed a termination region in which three different terminator sequences have been placed in tandem. These three terminators are flanked by unique restriction enzyme sites useful for the cloning of genes or operons. The tonB terminator is a bidirectional rho-independent transcriptional terminator found between the *E. coli* tonB gene and an opposing gene (Postle, K.; Good, R. F., *Cell*, 41, 577-585 (1985)). The thr attenuator, similar in structure to other rho-independent terminators facilitates transcriptional termination of the *E. coli* threonine operon (Yanget et al., *J. BioL Chem.*, 270:23330-23336 (1995)). The aspA terminator with a structure characteristic of rho-independent terminators, facilitates transcriptional termination of the *E. coli* aspartase operon (Takagi et al., *Nucleic Acid Res.*, 13:2063-2074 (1985)).

As autonomous, self-replicating genetic elements, plasmids have the basic attributes to make them potential vectors for carrying cloned DNA. Naturally-occurring plasmids often lack several important features required in a high-quality cloning vector. These features include (1) a small size (necessary for efficient transfer of exogenous DNA into a host), (2) unique restriction endonuclease recognition sites into which the insert DNA can be cloned, and (3) one or more selectable genetic markers for identifying recipient cells that carry the cloning vector-insert DNA construct. Consequently, plasmid cloning vectors have to be genetically engineered (Glick, B. R., Pasternak, J. J., *Molecular Biotechnologqy Principles and Applications of Recombinant DNA*, 2$^{nd}$ ed., American Society for Microbiology, Washington, D.C. (1998)).

pCL1920/21 vectors are a pair of low-copy-number plasmids that contain a 580 bp BstUI fragment carrying the lac promoter/operator, a multiple cloning site and lacZ fragment of pUC19 cloned in place of the polylinker region in pGB2, a pSC101-derived plasmid which confers spectinomycin and streptomycin resistance in *E. coli*. pCL1920/21 vectors (five copies per cell) have a 40-fold difference in plasmid copy number between pCL1920/21 vectors and pUC vectors (200 copies per cell). Thus, the pCL1920/21 vectors allow regulated low-level expression of genes inserted downstream of the promoter-operator when transformed into strains. They should also be useful for cloning genes that may be deleterious at high copy number. Since the pCL1920/21 vectors are compatible with ColE1-derived plasmids they can be used to form stable co-transformants together with pBR322 or pUC derived plasmids (Lerner et al., *Nucleic Acids Res.*, 18:4631 (1990)).

The plamids of the inventions may be used in a variety of hosts for the controlled bioproduction of materials.

Replacing Chromosomally-Located Native Promoters of any Endogenous Gene or Operon to Alter Transcriptional Level.

Claimed promoter variants (constructs comprising SEQ ID NOs:31 and 32) may be used in a method to replace chromosomally-located native promoters associated with any endogenous gene or operon in order to alter the transcription level of the gene or operon. The result is changed protein production levels. The promoter to be replaced can be any gene in any microorganism where the Llambda red method of Datsenko and Wanner [(2000) PNAS 97:6640-6645] or an equivalent method is operable.

In the method, a chimeric DNA molecule comprising a selectable marker operably linked to a divergently-arranged non-native promoter operably linked to the 5' coding region of a target gene is synthesized by polymerase chain reaction (PCR). The synthesis is accomplished using: (1) a pair of chemically synthesized primers, (a) the first primer comprising: (i) a DNA region distal to the target natural promoter to be replaced, (ii) a non-native promoter, and (iii) a DNA region from either the 3' or 5' end of the selectable marker; and (b) the second primer comprising: (i) a DNA region proximal to the targeted insertion site, and (ii) a DNA region from the opposite end of the selectable marker than was used in the first primer; and (2) a DNA template encoding a selectable marker. This product is integrated in the DNA product synthesized above at the chromosomal target site of any host cell using the method of Datsenko and Wanner (supra). The result of this protocol is that the target native promoter(s) are replaced with the PCR-synthesized chimeric molecule that carries the non-native promoter.

An extension of the method may be used to assess the effect of the varying gene expression level on biocatalyst performance.

Biosynthesis of 1,3-propanediol (3G) from Glucose in *E. coli*

The plasmids of the invention may be used in *E. coli* for the biosynthesis of 1,3-propanediol (3G) from glucose. The examples herein include the construction of a production organism that incorporates the claimed invention and the genetic machinery necessary to convert a fermentable carbon substrate to 1,3-propanediol.

The genes involved in 1,3-propanediol production include a dehydratase gene (typically a glycerol or diol dehydratase) and an oxidoreductase as well as other proteins expected to aid in the assembly or in maintaining the stability of the dehydratase enzyme. These genes may be transgenes introduced into the host cell, or may be endogenous. At least one of these genes will be a transgene and introduced into the production cell. Recombinant organisms containing the necessary genes that encode the enzymatic pathway to convert a carbon substrate to 1,3-propanediol may be constructed using techniques well known in the art. The transformed production cell is then grown under appropriate conditions for the production of 1,3-propanediol.

Production of 1,3-propanediol in *E. coli* has been previously described (U.S. Pat. No. 5,633,362; U.S. Pat. No. 5,821,092; U.S. Pat. No. 5,686,276; U.S. Pat. No. 6,025,184; U.S. Pat. No. 6,013,494; U.S. Pat. No. 5,599,689; U.S. Pat. No. 6,136,576). Expression of many different genes are involved in the production from glucose of 1,3-propanediol by a recombinant *E.coli*. Genes encoding glycerol dehydratase (dhaB) and 1,3-propanediol oxidoreductase (dhaT) were isolated from a native host such as *Klebsiella* and used to transform host strains such as *E.coli* strain DH5α or FM5; *K. pneumoniae* strain ATCC 25955; *K. oxytoca* strain ATCC 8724 or M5a1, *S. cerevisiae* strain YPH499, *P. pastoris* strain GTS115, and *A. niger* strain FS1.

In *Klebsiella pneumonia, Citrobacter freundii*, and *Clostridium pasteurianum*, the genes encoding the three structural subunits of glycerol dehydratase (dhaB1-3 or dhaB, C, and E) are located adjacent to a gene encoding a specific 1,3-propanediol oxidoreductase (dhaT). Although the genetic organization differs somewhat among these microorganisms, these genes are clustered in a group that also includes orfX and orfZ (genes encoding a dehydratase reactivation factor for glycerol dehydratase), as well as orfY and orfW (genes of unknown function). The specific 1,3-propanediol oxidoreductases (dhaT's) of these microorganisms are known to belong to the family of type III alcohol dehydrogenases; each exhibits a conserved iron-binding motif and has a preference for the $NAD^+$/NADH linked interconversion of 1,3-propanediol and 3-HPA. However, the $NAD^+$/NADH linked interconversion of 1,3-propanediol and 3-HPA is also catalyzed by alcohol dehydrogenases which are not specifically linked to dehydratase enzymes (for example, horse liver and baker's yeast alcohol dehydrogenases (E.C. 1.1.1.1)), albeit with less efficient kinetic parameters. Glycerol dehydratase (E.C. 4.2.1.30) and diol [1,2-propanediol] dehydratase (E.C. 4.2.1.28) are related but distinct enzymes that are encoded by distinct genes. Diol dehydratase genes from *Klebsiella oxytoca* and *Salmonella typhimurium* are similar to glycerol dehydratase genes and are clustered in a group which comprises genes analogous to orfX and orfZ (Daniel et al., FEMS *Microbiol. Rev.* 22:553 (1999); Toraya and Mori, *J. Biol. Chem.* 274:3372 (1999); GenBank AF026270).

The gene encoding glycerol-3-phosphate dehydrogenase (DAR1, GPD1) has been cloned and sequenced from *S. diastaticus* (Wang et al., *J. Bact.* 176:7091-7095 (1994)). The DAR1 gene was cloned into a shuttle vector and used to transform *E. coli* where expression produced active enzyme. Wang et al. (supra) recognize that DAR1 is regulated by the cellular osmotic environment but do not suggest how the gene might be used to enhance 1,3-propanediol production in a recombinant microorganism.

Other glycerol-3-phosphate dehydrogenase enzymes have been isolated. For example, sn-glycerol-3-phosphate dehydrogenase has been cloned and sequenced from *Saccharomyces cerevisiae* (Larason et al., *Mol. Microbiol.* 10: 1101 (1993)). Albertyn et al. (*Mol. Cell. Biol.* 14:4135 (1994)) teach the cloning of GPD1 encoding a glycerol-3-phosphate dehydrogenase from *Saccharomyces cerevisiae*. Like Wang et al. (supra), both Albertyn et al. and Larason et al. recognize the osmo-sensitivity of the regulation of this gene but do not suggest how the gene might be used in the production of 1,3-propanediol in a recombinant microorganism.

As with G3PDH, glycerol-3-phosphatase has been isolated from *Saccharomyces cerevisiae* and the protein identified as being encoded by the GPP1 and GPP2 genes (Norbeck et al., *J. Biol. Chem.* 271:13875 (1996)). Like the genes encoding G3PDH, it appears that GPP2 is osmosensitive.

EXAMPLES

The present invention is further defined in the following Examples that indicate preferred embodiments of the invention. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et a., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg, and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis., DIFCO Laboratories (Detroit, Mich.), GIBCO/BRL (Gaithersburg, Md.), New England Biolabs (Beverly, Mass.) or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters, "mm" means millimeters, "nm" means nanometers, "mM" means millimolar, "M" means molar, "mmol" means millimole(s), "µmole" mean micromole", "g" means gram, "µg" means microgram.

Example 1

Construction of Glucose Isomarase Promoter Variants

The *Streptomyces lividans* glucose isomerase (GI) promoter (SEQ ID NO:1) contains a characteristic −10 signature sequence (AATAAT) and a characteristic −35 signature sequence (−35 T, −34 T, −33 G, −32 A, −31 C, −30 A). Using mixed base oligonucleotides, saturation mutagenesis of the −35 region of the GI promoter in pMP38 (as described in Example 6 following) was performed by standard PCR. In six individual PCR reactions, an upstream primer (SEQ ID NO:2) was paired with one of six downstream primers (SEQ ID NOs:3-8), each of which contains an equal mixture of all four possible bases at a single position in the −35 region, designated as N. The upstream primer also incorporates two single base pair changes that change a SpeI restriction site (ACTAGT) immediately following the EcoRI site to an AvrII restriction site (CCTAGG). The six PCR products were digested with EcoRI and HindIII, and individually ligated to EcoRI/HindIII digested pMP38. Ligations were transformed into *E. coli*, and recombinant plasmids were identified through restriction analysis by the SpeI to AvrII conversion, and subjected to nucleotide sequencing. Only recombinant plasmids would be expected to harbor possible −35 region changes. Of the twenty-four possible recombinant outcomes (4 bases in 6 positions), 18 were obtained, of which 13 represent changes in the −35 region (Table 1).

TABLE 1

GI promoter variants obtained by saturation mutagenesis PCR

| Position | Base | Name | Comments | SEQ ID NO. |
|---|---|---|---|---|
| −30A | A | P1.6 | No change in −35 region | 9 |
|  | T | P1.5 |  | 10 |
|  | G | P1.20 |  | 11 |
|  | C | P1.10 |  | 12 |
| −31C | C | P2.8 | No change in −35 region | 9 |
|  | A | P2.39 |  | 13 |
| −32A | A | P3.4 | No change in −35 region; 25 bp deletion between −10 and -HindIII site | 14 |
|  | C | P3.5 |  | 15 |
| −33G | G | P4.49 | No change in −35 region | 9 |
|  | A | P4.15 |  | 16 |
|  | C | P4.1 |  | 17 |

TABLE 1-continued

GI promoter variants obtained by saturation mutagenesis PCR

| Position | Base | Name | Comments | SEQ ID NO. |
|---|---|---|---|---|
| −34T | T | P5.10 | No change in −35 region | 9 |
|  | C | P5.12 |  | 18 |
|  | A | P5.17 |  | 19 |
|  | G | P5.19 |  | 20 |
| −35T | T | NA | No change in −35 region | 9 |
|  | G | P6.5 |  | 21 |
|  | A | P6.14 |  | 22 |
|  | C | P6.20 |  | 23 |

*NA = Not Applicable

Although five of the possible 18 changes in the −35 region were not isolated, these may also be useful for varying expression levels of cloned or chromosomally-encoded native and non-native genes or operons. These five additional GI promoter variants are described in Table 2.

TABLE 2

Other Potential GI Promoter Variants

| Position | Base | SEQ ID NO. |
|---|---|---|
| −31C | G | 24 |
|  | T | 25 |
| −32A | G | 26 |
|  | T | 27 |
| −33G | T | 28 |

Example 2

Analysis of Glucose Isomerase Promoter Variants by Measuring Glycerol Dehydratase Activity Glycerol dehydratase (GDH; encoded by dhaB1-3) activity was used as a reporter to measure the effect of the GI promoter mutations (Table 3). It was observed that even in the absence of a change in the −35 region, GDH activity dropped significantly due to the two base pair changes which converted SpeI to AvrII (for example, P1.6). It was also determined that P3.4 did not have a −35 mutation, but did have a 25 base pair deletion immediately following the −10 region, and had nearly wild-type (86%) promoter strength.

Dehydratase activity in cell-free extracts was determined using either glycerol or 1,2-propanediol as substrate. Cell-free extracts were prepared by cell disruption using a French press followed by centrifugation of the cellular debris. The assay, based on the reaction of aldehydes with methylbenzo-2-thiazolone hydrazone, has been described by Forage and Foster (*Biochim. Biophys. Acta* 569:249 (1979)).

TABLE 3

Measure of Relative GDH Activity In GI Promoter Variants

| Plasmid | relative GDH activity |
|---|---|
| pMP38 | 100 |
| pMP38/1.6 | 13 |
| pMP38/1.5 | 3 |
| pMP38/1.20 | 1 |
| pMP38/1.10 | 1 |

TABLE 3-continued

Measure of Relative GDH Activity In GI Promoter Variants

| Plasmid | relative GDH activity |
| --- | --- |
| pMP38/2.39 | 0 |
| pMP38/3.4 | 86 |
| pMP38/3.5 | 1 |
| pMP38/4.1 | 0 |
| pMP38/4.15 | 0 |
| pMP38/5.12 | 0 |
| pMP38/5.17 | 0 |
| pMP38/5.19 | 0 |
| pMP38/6.5 | 0 |
| pMP38/6.14 | 1 |
| pMP38/6.20 | 2 |

Example 3

Analysis of GI Promoter Variants Using LUX Assays

A second type of reporter was used to measure levels of expression driven from the GI promoter variants. Bacterial bioluminescence is a phenomenon in which the products of 5 structural genes (luxA, luxB, luxC, luxD, and luxE) work in concert to produce light. The luxD product generates a C14 fatty acid from a precursor. The C14 fatty acid is activated in an ATP dependent reaction to an acyl-enzyme conjugate through the action of the luxE product, which couples bacterial bioluminescence to the cellular energetic state. The acyl-enzyme (luxE product) serves as a transfer agent, donating the acyl group to the luxC product. The acyl-LuxC binary complex is then reduced in a reaction in which NADPH serves as an electron pair and proton donor reducing the acyl conjugate to the C14 aldehyde. This reaction couples the reducing power of the cell to bacterial light emission. The light production reaction, catalyzed by luciferase (the product of luxA and luxB), generates light. The energy for light emission is provided by the aldehyde to fatty acid conversion and $FMNH_2$ oxidation, providing another couple between light production and the cellular energy state.

The *Photorabdus luminenscens* luxAB genes were used as reporters for GI promoter variant strength (Van Dyk et al., *Appl. Environ. Microbiol.*, 180:785-792 (1995)). A PCR fragment carrying the *P. luminenscens* luxAB genes and containing SpeI sites at the 3' and 5' ends and an NcoI site engineered at the initiation codon of luxA was subcloned into the SpeI site in pMCS5 (MobiTec, Göttingen, Germany) yielding pJT13. Then a gene SOEing PCR-based kanamycin cassette with SwaI/NcoI ends was cloned into SwaI/NcoI-digested pJT13 to make pJT14.HIGHCOPY, the high copy luxAB promoter probe. pJT14.HIGHCOPY was then digested with SpeI producing the luxAB::kanamycin cassette, which was subcloned into the unique NheI site (compatible with SpeI), in pRJ50 (SEQ ID NO:79) to make pJT14.LOWCOPY.1, the low copy luxAB promoter probe. The GI promoters 1.6, 1.5, 1.20, and native were cloned into pJT14.HIGHCOPY and pJT14.LOWCOPY as NotI/NcoI fragments to make the high-copy constructs pJT18, pJT19, pJT20, and pJT25, respectively, and low-copy constructs pJT21.1, pJT22.1, pJT23.1, and pJT26.1, respectively. The plasmids were then transformed into select *E. coli* strains for in vivo bioluminescence measurements.

Promoter strengths were measured by luminometry using broth cultures of *E. coli* reporter strains, n-decanal as the aldehyde substrate, and a luminometer, as described by Van Dyk and Rosson (*Methods in Molecular Biology, Vol.* 102: *Bioluminescence Methods and Protocols,* 85 (1998)). *E. coli* clones were inoculated from a fresh agar plate into test tubes containing standard Luria-Bertani liquid growth medium with the appropriate antibiotic and grown aerobically (with shaking) at 37° C. for approximately 16 h. Cells were then subcultured into 100-mL flasks containing 25 mL of fresh medium and grown under the same conditions for approximately 8-10 h. Aliquots (200 µL) were then taken from each culture and placed into 96-well clear and white plates for optical density measurements at 600 nm (SpectraMax 190 Plater Reader, Molecular Devices Corporation, Sunnyvale, Calif.) and luminometer measurements (Luminoscan Ascent TAype 392, LabSystems, Helsinki, Finland), respectively. For the luminometry readings, 2 µL of exogenous aldehyde (n-decanal) was added to each well and measurements made. Results from these assays are listed in Table 4. These luminometry measurements indicated a level of promoter strength similar to that indicated by glycerol dehydratase assays.

TABLE 4

| | Bioluminescence Measurements | |
| --- | --- | --- |
| GI Promoter | Plasmid construct | Relative Bioluminescence |
| GI wildtype | pJT26.1 | 100% |
| GI 1.6 | pJT21.1 | 12.9% |
| GI 1.5 | pJT22.1 | 3.0% |
| GI 1.20 | pJT23.1 | 1.3% |

Example 4

Use of Shortened GI Promoter Sequences to Achieve Different Levels of Gene Expression A subset of the GI promoter sequences described and used in Examples 1-3 were used to vary levels of expression of *E. coli* yqhD (SEQ ID NO:29) from the pSYCO109mcs plasmid (as described in Example 8 and SEQ ID NO:30) in strain RJ8n in which the yqhD gene was disrupted on the chromosome to create strain RJ8n (yqhD–).

Three expression cassettes for yqhD were constructed. These cassettes contain (i) one of the shortened GI promoters designated short 1.5 GI (SEQ ID NO:31), short 1.20 GI (SEQ ID NO:32), or short wild-type GI (SEQ ID NO:33); (ii) yqhD from *E. coli* KLP23 (WO9928480); and (iii) the threonine terminator (Lynn et al., *J. Mol. Biol.,* 183:529-541 (1985)). The yqhD gene was isolated by PCR amplification from genomic KLP23 DNA using forward synthetic primers for short 1.5 GI (SEQ ID NO:34), short 1.20 GI (SEQ ID NO:35), or short wild-type GI (SEQ ID NO:36) which contain one of the shortened GI promoters and also incorporate a RsrII restriction site, and the reverse primer for yqhD (SEQ ID NO:37) that contained the threonine terminator and included a SacI site. Plasmid pSYCO109mcs was digested with RsrII/SacI and the RsrII/SacI digested PCR products were ligated into the plasmid. The ligation mixture was transformed into the RJ8n (yqhD–) strain by electroporation and the enzyme activity levels in each of the strains were compared (Table 5.)

The enzyme activity expressed by yqhD will reduce the aldehydes 3-hydroxypropionaldehyde (3-HPA) and butanal with similar rates using NADPH as the source of reducing equivalents. Since 3-HPA is not commercially available, butanal is generally used. The assay mixture contained in 1 mL total volume: 200 mM potassium phosphate buffer (pH 7.5), 10 mM butanal, 0.2 mM NADPH, and approximately 0.01 mg protein from cell-free extracts to be assayed. The initial rate of oxidation of NADPH after addition of protein sample was followed by measuring the change in absorbance at 340 nm ($\Delta\epsilon=6.22$ mM$^{-1}$). A unit of activity is defined as that required to oxidize 1 micromole of NADPH in 1 minute in the presence of 10 mM butanal at 35° C. The activities of various strains are given in Table 5 below and were consistent with levels of expression allowed by the longer GI promoter variants.

TABLE 5

YqhD Activity

| Strain and construct | Activity (U/mg) | % Activity |
|---|---|---|
| RJ8n(yqhD-) | 0.015 | 0.8 |
| RJ8n(yqhD-)/pSYCO109mcs | 0.010 | 0.5 |
| RJ8n(yqhD-)/pSYCO109mcs-short 1.20 GI yqhD | 0.14 | 7.3 |
| RJ8n(yqhD-)/pSYCO109mcs-short 1.5 GI yqhD | 0.29 | 15 |
| RJ8n(yqhD-)/pSYCO109mcs-short wild-type GI yqhD | 1.92 | 100 |

To create RJ8n (yqhD-) the yqhD gene was disrupted in *E. coli* MG1655 using the procedure as described by Wanner and Datsenko (*PNAS*, 97(12):6640-6645 (2000)) for Red-mediated homologous recombination. The forward PCR primer H1::6574 (SEQ ID NO:38) (containing 42 bp of sequence homologous to yqhD and the primer binding site P1 to pKD13) and the reverse PCR primer H2::6706 (SEQ ID NO:39) (containing 47 bp of homologous yqhD sequence and the primer binding site P4 to pKD13) were prepared. PCR amplification with pKD13 as the template produced a PCR product that had yqhD sequence on each end followed by FRT (FLP recognition target) sites that flank a kanamycin resistance (kanR) marker. The PCR product was electrotransformed into *E. coli* MG1655 cells and kanamycin-resistant transformants were selected. Correct insertion in the transformants was confirmed by PCR using primers yqhDUP (SEQ ID NO:82) and yqhDDN (SEQ ID NO:83) flanking the yqhD gene. The temperature-sensitive plasmid containing the Lambda Red system was cured by growth of the strains at 42° C.

The yqhD::kan disruption was moved into RJ8n by P1 transduction and confirmed by PCR using the yqhDUP2 (SEQ ID NO:40) and yqhDDN2 (SEQ ID NO:41) primers paired with primers internal to the kanR gene (Vec 61; SEQ ID NO:42 and Vec 60; SEQ ID NO:43). To remove the kanamycin marker, integrants were transformed with the temperature-sensitive replicon, pCP20, which contains the gene for the FLP recombinase. FLP recombinase excises the kanamycin marker at the flanking FRT (FLP recognition target) sites.

Kanamycin-sensitive cells were then grown at 42° C. to cure pCP20. The resultant strain was RJ8n (yqhD-).

Example 5

Replacement of the *E. Coli* Phosphoenolpyruvate Carboxylase Chromosomal Promoter with a GI Promoter Example 5 describes the replacement in the *Escherichia coli* genome of the natural ppc (encoding the phosphoenolpyruvate carboxylase or PEP carboxylase) promoter by the short wild-type GI promoter (SEQ ID NO:33).

Design of the Oligonucleotides for the ppc Promoter Replacement

Two oligonucleotides (ppcF, SEQ ID NO:44 and ppcR, SEQ ID NO:45) were designed to amplify by PCR a cassette containing an 80-bp sequence homologous to the upstream region of the natural ppc promoter, a chloramphenicol-resistance encoding gene (cat) flanked by baker yeast FRT sites, the short wild-type GI promoter sequence (SEQ ID NO:33), and a 40-bp sequence homologous to the downstream region of the +1 transcription start site of the natural ppc promoter.

The ppcR primer (SEQ ID NO:45) is 100 nucleotides long and includes: the entire sequence from the +1 of P1 (natural ppc promoter) transcription start to 41 bp upstream the ATG of ppc, the short wild-type GI promoter sequence (SEQ ID NO. 33) from 4 bp upstream of the −35 to 9 bp downstream of the −10, and the priming site for pKD3 (Wanner and Datsenko, supra), an R6K plasmid containing the cat gene flanked by two FRT sites. The ppcF primer (SEQ ID NO:44) is 100 nucleotides long and includes 80 bp of sequence upstream of the natural ppc promoter and the priming site for pKD3.

Primers ppcF and ppcR (SEQ ID NOs:44 and 45) were used to amplify the promoter replacement cassette using plasmid pKD3 as a template. The 1.15-kb PCR product was purified by agarose gel electrophoresis followed by QIAquick gel extraction Kit (Qiagen, Inc., Valencia, Calif.).

Replacement of the Natural ppc Promoter into *Escherichia coli* Genome by Homologous Recombination Using Linear DNA Competent *Escherichia coli* MG1655 cells containing pKD46 (Datsenko and Wanner, supra), a Red-recombinase plasmid expressing γ, β, and exo under the control of the arabinose promoter, were electrotransformed with 0.5 µg of the above 1.15-kb linear DNA and the resulting transformants were screened for chloramphenicol resistance (15 µg/mL). The recombinant strains were checked by PCR using primers ppcF and seqppcR (SEQ ID NO:46). Non-specific integration of the cassette gives no PCR products while true recombinants give a 1.25-kb PCR product. The sequence of the short wild-type GI promoter was confirmed by sequencing the 1.25-kb PCR product with the seqppcR primer (SEQ ID NO:46).

Measurement of Enzymatic Activity

The PEP carboxylase activities in MG1655 and in MG1655 (short wild-type GI-ppc) were measured on ultracentrifuged cell-free extract using the following assay and are indicated in Table 6. The activity of PPC under control of the short wild-type GI promoter was over three times higher than under control of the natural promoter.

The decrease at 340 nm (due to consumption of NADH) was measured in a mixture containing: 0.11 M Tris buffer (pH 8.5), NADH (0.22 mM), Magnesium sulfate (11.1 mM), Sodium bicarbonate (11.1 mM), Acetyl-CoA (0.25 mM), MalateDH (Sigma), 50 μL of 6 U cell extracts and 0.03 Phosphoenolpyruvate (1.11 mM). The following formula was used to determine activity:

$$\text{Units/mg} = \frac{\Delta A340/\min \text{ (test)} - \Delta A340/\min \text{ (blank)}}{6.22 \times \text{mg protein/mL reaction mixture}}$$

TABLE 6

Activity of PPC from natural and GI1.6 promoters

| Strain | Activity (U/mg) |
|---|---|
| MG1655 | 0.05 |
| MG1655 (1.6GI ppc) | 0.164 |

Example 6

Construction of an Expression Plasmid for Use in Transformation of *Escherichia Coli* with Genes from the *Klebsiella Pneumoniae* dha Regulon Construction of the Expression Vector pTacIQ:

The *E. coli* expression vector pTacIQ was prepared by inserting the lacI$^Q$ gene (Farabaugh, *Nature*, 274(5673):765-769 (1978)) and tac promoter (Amann et al., *Gene* 25:167-178 (1983)) into the EcoRI site of pBR322 (Sutcliffe, *Cold Spring Harb. Symp. Quant. Biol.* 43:77-90 (1979)). A multiple cloning site and terminator sequence (SEQ ID NO:47) replaced the pBR322 sequence from EcoRI to SphI.

Subcloning the Glycerol Dehydratase Genes (dhaB1, 2, 3, X):

The open reading frame for the dhaB3 gene was amplified from pHK28-26 (SEQ ID NO:48) by PCR using primers (SEQ ID NOs:49-50) incorporating an EcoRI site at the 5' end and a XbaI site at the 3' end. The product was subcloned into pLitmus29 (New England Biolabs) to generate the plasmid pDHAB3 containing dhaB3.

The region (containing the entire coding region for dhaB1, dhaB2, dhaB3, and dhaBX of the dhaB operon from pHK28-26) was cloned into pBluescriptIIKS+ (Stratagene, La Jolla, Calif.) using the restriction enzymes KpnI and EcoRI to create the plasmid pM7.

The dhaBX gene was removed by digesting plasmid pM7 with ApaI and XbaI, purifying the 5.9-kb fragment and ligating it with the 325-bp ApaI-XbaI fragment from plasmid pDHAB3 to create pM11 (containing dhaB1, dhaB2, and dhaB3).

The open reading frame for the dhaB1 gene was amplified from pHK28-26 by PCR using primers (SEQ ID NOs:51-52) incorporating a HindIII site and a consensus ribosome-binding site (RBS) at the 5' end and a XbaI site at the 3' end. The product was subcloned into pLitmus28 (New England Biolabs) to generate the plasmid pDT1 containing dhaB1.

A NotI-XbaI fragment from pM11 (containing part of the dhaB1 gene, the dhaB2 gene, and the dhaB3 gene) was inserted into pDT1 to create the dhaB expression plasmid, pDT2. The HindIII-XbaI fragment (containing the dhaB(1,2, 3) genes from pDT2) was inserted into pTacIQ to create pDT3.

Subcloning the 1.3-Propanediol Dehydrogenase Gene (dhaT):

The KpnI-SacI fragment of pHK28-26 (containing the 1,3-propanediol dehydrogenase (dhaT) gene) was subcloned into pBluescriptII KS+ creating plasmid pAH1. The dhat gene was amplified by PCR using pAH1 as template DNA and the synthetic primers (SEQ ID NOs:53-54) which incorporated an XbaI site at the 5' end and a BamHI site at the 3' end. The product was subcloned into pCR-Script (Stratagene) at the SrfI site to generate the plasmids pAH4 and pAH5 containing dhaT. The plasmid pAH4 contains the dhat gene in the correct orientation for expression from the lac promoter in pCR-Script and pAH5 contains dhaT gene in the opposite orientation. The XbaI-BamHI fragment from pAH4 (containing the dhaT gene) was inserted into pTacIQ to generate plasmid pAH8. The HindII-BamHI fragment from pAH8 (containing the RBS and dhat gene) was inserted into pBluescriptIIKS+ to create pAH11.

Construction of an Expression Cassette for dhaT and dhaB (1.2.3):

An expression cassette for dhaT and dhaB(1,2,3) was assembled from the individual dhaB(1,2,3) and dhaT subclones described previously using standard molecular biology methods. A SpeI-SacI fragment (containing the dhaB(1, 2,3) genes from pDT3) was inserted into pAH11 at the SpeI-SacI sites to create pAH24. A SalI-XbaI linker created from SEQ ID NOs:55-56 was inserted into pAH5 that was digested with the restriction enzymes SalI-XbaI to create pDT16. The linker destroys the XbaI site. The 1-kb SalI-MluI fragment from pDT16 was then inserted into pAH24 replacing the existing SalI-MluI fragment to create pDT18. pDT21 was constructed by inserting the SalI-NotI fragment from pDT18 and the NotI-XbaI fragment from pM7 into pCL1920 (GenBank AX085428). The glucose isomerase promoter sequence from *Streptomyces lividans* (SEQ ID NO:1) was cloned by PCR and inserted into EcoRI-HindIII sites of pLitmus28 to construct pDT5. pCL1925 was constructed by inserting the EcoRI-PvuII fragment of pDT5 (containing the GI promoter) into the EcoRI-PvuII site of pCL1920 (GenBank AX085428).

Construction of Expression Vector for Glycerol Dehydratase under the Control of the *Streptomyces* Glucose Isomerase Promoter:

The HindIII restriction fragment (containing dhaT) was deleted from pDT24 to generate pRN105. The pDT24 plasmid was constructed by cloning the HindIII-MluI fragment of pDT21 and the MluI-XbaI fragment of pDT21 into the HindIII-XbaI sites of pCL1925. A PCR product (comprising the 3' region of dhaX, from a unique HpaI restriction site to the end of dhaX, and incorporating the HpaI restriction site at the 5' end and an XbaI restriction site at the 3' end) was generated from pRN105 template and used to replace the existing HpaI/XbaI restriction fragment in pRN105, generating pMP37. A PCR product (comprising the 5' region of dhaB1, from a unique HindIII restriction site just upstream of the start codon to a unique NotI restriction site within dhaB1, and incorporating the HindIII restriction site at the 5' end and the NotI restriction site at the 3' end) was generated from pDT29 template and used to replace the small HindIII/NotI restriction fragment in pRN105, generating pRJ25. The pDT29 had been constructed by inserting the SacI-EcoRI fragment of pHK28-26 into SacI-EcoRI sites of pCL1925. The small HpaI/XbaI restriction fragment (containing the 5' region of dhaX from pMP37) was ligated to the large XbaI/HpaI restriction fragment from pRJ25 to generate pMP38, in which the *Streptomyces lividans* glucose isomerase promoter (SEQ ID NO:1) drives expression of the *K. pneumoniae* dhaB1-3,X operon using the native ribosome-binding site.

Example 7

Construction of SYCO Plasmids for Production of 1,3-Propanediol

To produce 1,3-propanediol from glucose in an *E. coli* host, several operons from different sources can be expressed. These include genes coding for a glycerol-3-phosphate dehydrogenase, glycerol-3-phosphate phosphatase, and glycerol dehydratase activity. These genes may come from sources such as the dha operon from *Klebsiella pnuemoniae* (containing dhaR, dhaT, dhaX, and dhaB1-3), and the orf operon also from *Klebsiella pnuemoniae* (containing orfYXW), and an operon containing DAR1 and GPP2 from *Saccharomyces*. In order to maintain strain stability in fermentation it is preferable to maintain as few plasmids as possible in the *E. coli* host. To this end a series of plasmids were constructed to enable cloning of at least three different operons on a single plasmid. Three transcriptional terminators were used to flank unique cloning sites in order to prevent read-through of the RNA polymerase. These transcriptional terminators included the tonB terminator, thr attenuator and aspA terminator. The tonB terminator is a bi-directional rho-independent terminator located between the *E. coli* tonB gene and an opposing gene (Postle, K. and Good, R. F., *Cell*, 41:577-585 (1985)). The thr attenuator facilitates transcriptional termination of the *E. coli* threonine operon (Lynn et al., *J. Mol. Biol.*, 183:529-541 (1985)). The aspA terminator facilitates transcriptional termination of the *E. coli* aspartase operon (Takagi et al., *Nucleic Acid Research*. 13(6):2063-2072 (1985)).

Construction of pRJ50 Comprising Three Transcriptional Terminators Flanked by Unique Cloning Sites:

A synthetic DNA fragment (comprising the tonB, thr, and aspA transcriptional terminators (SEQ ID NO:57) and several restriction sites) was assembled using PCR-mediated overlap extension (Horton et al., *BioTechniques*, 8:528-535, (1990)). Two 100 base oligonucleotides (SEQ ID NOs:58-59) that complement each other for a span of 25 base pairs at the 3' ends were annealed to generate a 175-base DNA fragment (SEQ ID NO:60). Two additional oligonucleotide primers (SEQ ID NOs:61-62) were used to further amplify the 175-base fragment, which is flanked by EcoRI and KpnI restriction sites. The 175-base pair PCR product was digested with EcoRI and KpnI and subcloned into EcoRI/KpnI digested plasmid pCL1925 to generate pRJ50 (SEQ ID NO:79).

Construction of an Expression Cassette for dhaR, orfY, orfX, orfW and dhaB(1.2.3,X):

A derivative of plasmid pDT29 was constructed in which all except the first five and the last five codons (plus stop codon) of the gene dhaT were deleted by a technique known as PCR-mediated overlap extension. Using pDT29 as the template, two primary PCR products were generated using the following primers:

```
SEQ ID NO:63 = 5'GAC GCA ACA GTA TTC CGT CGC3';

SEQ ID NO:64 = 5'ATG AGC TAT CGT ATG TTC CGC CAG
               GCA TTC TGA GTG TTA ACG3';

SEQ ID NO:65 = 5'GCC TGG CGG AAC ATA CGA TAG CTC
               ATA ATA TAC3';

SEQ ID NO:66 = 5'CGG GGC GCT GGG CCA GTA CTG3'.
```

SEQ ID NO:65 was paired with SEQ ID NO:66 to generate a product of 931 bps and encompassing nucleic acid including 5' dhaB1 (to unique ScaI site), all of orfY, and the first five codons of dhaT. SEQ ID NO:63 was paired with SEQ ID NO:64 to generate a product of 1348 bps and encompassing nucleic acid including the last five codons (plus stop codon) of dhaT, all of orfX, all of orfW, and 5' dhaR (to unique SapI site). The 15 bases at the 5' end of SEQ ID NO:64 constitute a tail that is the inverse complement of a 15-base portion of SEQ ID NO:65. Similarly, the 11 bases at the 5' end of SEQ ID NO:65 constitute a tail that is the inverse complement of an 11-base portion of SEQ ID NO:64. Thus, the two primary PCR products were joined together after annealing (via 26-bp tail overlap) and extending by PCR, to generate a third nucleic acid product of 2253 bps. This third PCR product was digested with SapI and ScaI and ligated into pDT29 which was also digested with SapI and ScaI, to generate the plasmid pKP32, which is identical to pDT29, except for the large, in-frame deletion within dhaT.

Construction of Plasmids for Expression of orfWXY and dhaB1-3 Containing Different GI Promoter Variants:

The orf operon from pKP32 was PCR-amplified (SEQ ID NOs:80-81) with HindIII at the 5' end and AvrtII at the 3' end, and subcloned between HindIII and AvrII in pLitmus28 (New England Biolabs) to generate pKP38. The EcoRI/HindIII restriction fragment (containing the GI mutant promoter P1.6 (SEQ ID NO:9) from pMP38/1.6) was subcloned between EcoRI and HindIII in pKP38 to generate pKP39. The AvrII/XbaI restriction fragment (containing the dhaB expression cassette from pMP38/1.6) was subcloned between AvrII and XbaI in pLitmus28 (New England Biolabs) to generate pMP39. The AvrII/XbaI. restriction fragment (containing the dhaB expression cassette from pMP39) was subcloned into the AvrII site of pRJ50 to generate pSYCO11. The AvrII restriction fragment (containing the orf expression cassette from pKP39) was subcloned into the NheI site of pSYCO11 to generate pSYCO12. The plasmids pSYCO11 and pSYCO12 are identical except that pSYCO11 does not contain the orf operon.

The EcoRI/HindIII restriction fragment (containing the GI mutant promoter P1.5 (SEQ ID NO:10) from pMP38/1.5) was subcloned between EcoRI and HindIII in pKP38 to generate pKP40. The AvrII restriction fragment (containing the orf operon driven by P1.5 from pKP40) was subcloned into the NheI site of pSYCO11 to generate pSYCO13. The AvrII/NotI restriction fragment (containing the P1.6 and 5' end of dhaB1in pSYCO13) was replaced with the corresponding AvrII/NotI restriction fragment from pMP38/1.5 to generate pSYCO19.

Construction of pSYCO101, pSYCO103, pSYCO106 and pSYCO109 Vectors with Three Operons each Isolated by Transcriptional Terminators:

A double-stranded nucleic acid linker (SEQ ID NO:67) was subcloned between the XbaI and SmaI restriction sites in pCL1920 (GenBank AX085428) to generate pCR-pCL1920. The glycerol pathway expression cassette in pAH48 comprising the trc promoter which was derived from pTrc99A (Amersham Pharmacia Biotech, Piscataway, N.J.), the coding sequences for DAR1 and GPP2, of *S. cerevisiae*, and the terminator rrnBT1T2 (from pTrc99A) was PCR- amplified (SEQ ID NOs:68-69) and subcloned into the SrfI restriction site of pCR-pCL1920 to generate pAH105 (SEQ ID NO:70).

The PvuII(2)/PvuII(4) restriction fragment (containing the DAR1/GPP2 expression cassette from pAH105) was subcloned into the Bst1107I site of pSYCO12 to generate pSYCO101 (SEQ ID NO:71). The DAR1/GPP2 operon is in the opposite orientation relative to the orf operon and the dhaB operon. The NheI restriction fragment (containing the DAR1/GPP2 expression cassette from pAH105) was subcloned into the XbaI site of pSYCO19 to generate pSYCO103 (SEQ ID NO:72).

The plasmid pSYCO103 comprises (a) a set of two exogenous genes obtained from *Saccharomyces cerevisiae* (DAR1 (a gene encoding glycerol-3-phosphate dehydrogenase) and GPP2 (a gene encoding glycerol-3-phosphatase)); (b) a set of three exogenous genes obtained from *Klebsiella pneumoniae* (dhaB1(a gene encoding the "α" subunit of glycerol dehydratase), dhaB2 (a gene encoding the "β" subunit of glycerol dehydratase), and dhaB3 (a gene encoding the "γ" subunit of glycerol dehydratase)); and (c) a set of two exogenous genes obtained from *Klebsiella pneumoniae* (dhaBX (a gene encoding the "α" subunit of dehydratase reactivation factor) and orfX (a gene encoding the "β" subunit of dehydratase reactivation factor)). In pSYCO103 the DAR1/GPP2 operon is in the same orientation relative to the orf operon and the dhaB operon.

The NheI restriction fragment (containing the DAR1/GPP2 expression cassette from pAH105) was subcloned into the XbaI site of pSYCO12 to generate pSYCO106 (SEQ ID NO:73). The DAR1/GPP2 operon is in the same orientation relative to the orfoperon and the dhaB operon. The PmlI/NotI restriction fragment in pSYCO106 was removed and replaced with the overlapping StuI/NotI restriction fragment from pSYCO106, resulting in a 141 base pairs deletion near the 3' end of orfW to generate pSYCO109 (SEQ ID NO:74).

Example 8

A Novel Nucleotide Sequence with Ten Rare Restriction Enzyme Sites Useful for Cloning A novel nucleotide sequence was designed to encode ten rare restriction endonuclease sites useful for cloning of additional genes, operons, or cassettes and as sites for transferring cassettes from this plasmid to another. The plasmid pSCYCO106deltaS was constructed by restricting pSYCO106 with SpeI, filling in the ends with Klenow and religating. The pSYCO106deltaS was digested with EcoRI to isolate the vector backbone and then recircularized by ligation to form pSpREPds. Oligonucleotides (SEQ ID NOs:75-76) were annealed at 60° C. and digested with KpnI/StuI. The multiple cloning fragment (SEQ ID NO:77) contains recognition sites for the following enzymes: NheI, RsrII, SacI, AgeI, SnaBI, AscI, PacI, NsiI, MluI, and SapI. The fragments were gel-purified and cloned to pSpREPds to form pSpREPmcs. The pSpREPmcs was linearized with EcoRI and the EcoRI fragments (containing the pathway genes from pSYCO106deltaS and pSYCO109) were ligated to pSpREPmcs to form pSYCO106mcs (SEQ ID NO:78) and pSYCO109mcs (SEQ ID NO: 30), respectively.

Example 9

Production of 1.3-Propanediol Using *E. Coli* Strain RJ8N/PSYCO101

The plasmid pSYCO101 (SEQ ID NO:71) was used to transform electrocompetent *E coli* RJ8n cells, resulting in the *E. coli* strain, RJ8n/pSYCO101.

RJ8n/pSYCO101 was pre-cultured for seeding a fermenter in 2YT medium (10 g/L yeast extract, 16 g/L tryptone, and 10 g/L NaCl) containing 50 mg/L spectinomycin. Cultures were started from frozen stocks (10% glycerol as cryoprotectant) in 500 mL of medium in a 2-L Erlenmeyer flask, grown at 35° C. in a shaker at 250 rpm until an $OD_{550}$ of approximately 1.0 was reached and used to seed the fermenter.

The following components were sterilized together in the fermenter vessel: 45 g $KH_2PO_4$, 12 g citric acid monohydrate, 12 g $MgSO_4.7H_2O$, 30 g yeast extract, 1.8 g ferric ammonium citrate, 5 mL Mazu DF204 as antifoam, 1.2 g $CaCl_2.2H_2O$, 7.2 mL sulfuric acid and 60 mL of a trace element solution. After sterilization, the pH was raised to 6.8 with 20-28% $NH_4OH$ and the following components were added: 0.30 g spectinomycin, and glucose (from a 67 weight % feed). The solution of trace elements contained (g/L): citric acid. $H_2O$ (4.0), $MnSO_4.H_2O$ (3.0), NaCl (1.0), $FeSO_4.7H_2O$ (0.10), $CoCl_2.6H_2O$ (0.10), $ZnSO_4.7H_2O$ (0.10), $CuSO_4.5H_2O$ (0.010), $H_3BO_3$ (0.010), and $Na_2MoO_4.2H_2O$ (0.010). After inoculation, the volume was 6.0 L and the glucose concentration was 10 g/L.

A 15-L stirred tank fermenter was prepared with the, medium described above. The temperature was controlled at 34° C. and aqueous ammonia (20-28 weight %) was used to control pH at 6.8. Dissolved oxygen (DO) control was set at 10% and back pressure was controlled at 0.5 bar. Except for minor excursions, glucose was maintained at between 10 g/L and 25 g/L with a 67% (wt) feed. An addition of 10 mg vitamin $B_{12}$ was made at 10 h elapsed fermentation time and a co-feed (2.64 mg/h of a 0.0167 mg/mL solution) begun one hour later. A titer of 99 g/L 1,3-propanediol was obtained after 64 h.

What is claimed is:

1. A pSYCO109mcs plasmid consisting of SEQ ID NO:30.

\* \* \* \* \*